United States Patent
Gualandi et al.

(10) Patent No.: US 11,629,199 B2
(45) Date of Patent: Apr. 18, 2023

(54) ANTIBODIES TO TUMOUR ANTIGENS

(71) Applicant: Philogen S.P.A., Siena (IT)

(72) Inventors: Laura Gualandi, Otelfingen (CH); Sarah Wulhfard, Otelfingen (CH); Francesca Pretto, Otelfingen (CH); Catherine Pemberton-Ross, Otelfingen (CH); Alessandra Villa, Otelfingen (CH); Roberto De Luca, Otelfingen (CH)

(73) Assignee: PHILOGEN S.P.A.

( * ) Notice: Subject to any disclaimer, the term of this patent is extended or adjusted under 35 U.S.C. 154(b) by 273 days.

(21) Appl. No.: 16/955,608

(22) PCT Filed: Dec. 19, 2018

(86) PCT No.: PCT/EP2018/086001
§ 371 (c)(1),
(2) Date: Jun. 18, 2020

(87) PCT Pub. No.: WO2019/122025
PCT Pub. Date: Jun. 27, 2019

(65) Prior Publication Data
US 2021/0054095 A1 Feb. 25, 2021

(30) Foreign Application Priority Data
Dec. 19, 2017 (EP) .................................. 17208671

(51) Int. Cl.
*C07K 16/30* (2006.01)
*C07K 14/525* (2006.01)
*C07K 14/55* (2006.01)
*A61K 39/00* (2006.01)

(52) U.S. Cl.
CPC ............ *C07K 16/30* (2013.01); *C07K 14/525* (2013.01); *C07K 14/55* (2013.01); *A61K 2039/505* (2013.01); *C07K 2317/34* (2013.01); *C07K 2317/56* (2013.01); *C07K 2317/565* (2013.01); *C07K 2317/567* (2013.01); *C07K 2317/622* (2013.01); *C07K 2317/92* (2013.01); *C07K 2319/33* (2013.01)

(58) Field of Classification Search
CPC ...... C07K 16/30; C07K 14/525; C07K 14/55; C07K 2317/34; C07K 2317/56; C07K 2317/565; C07K 2317/567; C07K 2317/622; C07K 2317/92; C07K 2319/33; A61K 2039/505
See application file for complete search history.

(56) References Cited

FOREIGN PATENT DOCUMENTS

| WO | 2003/048328 A3 | 6/2003 | |
|----|----------------|--------|---|
| WO | 2018/087172 A1 | 5/2018 | |
| WO | WO-2018087172 A1 * | 5/2018 | .......... A61K 38/191 |

OTHER PUBLICATIONS

Cazzamalli et al. Chemically Defined Antibody- and Small Molecule-Drug Conjugates for in Vivo Tumor Targeting Applications: A Comparative Analysis. J. Am. Chem. Soc. 2018, 140, 1617-1621. (Year: 2018).*
Cazzamalli et al. Chemically Defined Antibody- and Small Molecule-Drug Conjugates for in Vivo Tumor Targeting Applications: A Comparative Analysis. J. Am. Chem. Soc. 2018, 140, 1617-1621. Supplemental Information (Year: 2018).*
Cazzamalli et al., Chemically Defined Antibody- and Small Molecule-Drug Conjugates for in Vivo Tumor Targeting Applications: A Comparative Analysis, J. Am. Chem. Soc. (2018), 140 (5), 1617-1621.
Supplementary Information to Cazzamalli et al. J. Am. Chem. Soc. (2018), 140 (5), 1617-1621.
De-Kuan Chang et al.: "Human anti-CAIX antibodies mediate immune cell inhibition of renal cell carcinoma in vitro and in a humanized mouse model in vivo", Molecular Cancer, vol. 14, No. 1, Jun. 11, 2015, 119.
De Luca, R., "Dual Cytokine-Antibody Fusion Proteins: A Novel Class of Anti-Cancer Biopharmaceuticals." ETH Zurich.
Margarita T Murri-Plesko et al.: "Antibody inhibiting enzymatic activity of tumour-associated carbonic anhydrase isoform IX", European Journal of Pharmacology, vol. 657, No. 1, 2011, p. 173-783.
Adrianne H. Brouwers: "Radioimmunotargeting of Renal Cell Cancer using Monoclonal Antibody cG250", 2012.
Agnes Shuk-Yee Lo et al.: "Regression of established renal cell carcinoma in nude mice using lentivirus-transduced human T cells expressing a human anti-CAIX chimeric antigen receptor", Molecular Therapy—Oncolytics, vol. 1, Dec. 10, 2014.
J K J Ahlskog et al.: "Human monoclonal antibodies targeting carbonic anhydrase IX for the molecular imaging of hypoxic regions in solid tumours", British Journal of Cancer, vol. 101, No. 4, Jul. 21, 2009, p. 645-657.
McDonald et al., Recent Developments in Targeting Carbonic Anhydrase IX for Cancer Therapeutics, 2012, Oncotarget, 3(1): 84-97.
Xu et al., Unique Biological Properties of Catalytic Domain Directed Human Anti-CAIX Antibodies Discovered through Phage-Display Technology (2010), vol. 5, Issue 3.

* cited by examiner

*Primary Examiner* — Amy E Juedes
*Assistant Examiner* — Brian Hartnett
(74) *Attorney, Agent, or Firm* — Kathleen D. Rigaut; Howson & Howson LLP

(57) ABSTRACT

The present application relates to specific binding members that bind carbonic anhydrase IX (CAIX). In particular, the present application relates to the treatment, diagnosis and detection of tumours, e.g. solid tumours, using specific binding members that bind CAIX. The specific binding member may be conjugated to a biocidal or cytotoxic molecule, or to a detectable label.

14 Claims, 15 Drawing Sheets
Specification includes a Sequence Listing.

Figure 1A

EVQLLESGGGLVQPGGSLRLSCAASGFTFSSYAMSWVRQAPGKGLEWVSAIDGSGGSTYYADSVKGRF
TISRDNSKNTLYLQMNSLRAEDTAVYYCVKGPPVFDYWGQGTLVTVSS (SEQ ID NO: 7)

Figure 1B

GGGGSGGGGSGGGG (SEQ ID NO:9)

Figure 1C

SSELTQDPAVSVALGQTVRITCQGDSLRSYYASWYQQKPGQAPVLVIYGKNNRPSGIPDRFSGSSSGN
TASLTITGAQAEDEADYYCNSSKWSWDPVVFGGGTKLTVLG (SEQ ID NO: 8)

A

B

A

B

ANTIBODIES TO TUMOUR ANTIGENS

CROSS-REFERENCE TO RELATED APPLICATIONS

The present application is a § 371 of International Patent Application No. PCT/EP2018/086001, filed Dec. 19, 2018, which claims priority from EP Application No. 17208671.2, filed Dec. 19, 2017. The entire disclosure of each of the aforesaid applications is incorporated by reference in the present application.

Incorporation-by-Reference of Material Submitted in Electronic Form

Incorporated herein by reference in its entirety is the Sequence Listing submitted via EFS-Web as a text file named SEQ_LIST.txt, created May 28, 2020 and having a size of 41,130 bytes.

The present invention relates to specific binding members that bind carbonic anhydrase IX (CAIX). In particular, the present invention relates to the treatment, diagnosis and detection of tumours, e.g. solid tumours, using specific binding members that bind CAIX. The specific binding member may be conjugated to a biocidal or cytotoxic molecule, or to a detectable label.

BACKGROUND TO THE INVENTION

Carbonic anhydrases are a large family of zinc metalloenzymes whose major enzymatic function is to catalyse the reversible hydration of carbon dioxide ($CO_2$) to bicarbonate ($HCO_3^-$) and protons ($H^+$) ($CO_2 + H_2O \leftrightarrow HCO_3^- + H^+$). Carbonic anhydrases are important regulators in a variety of biological processes, including respiration, calcification, acid-base regulation, bone resorption, and biosynthetic processes. Sixteen distinct metalloenzymes in this family have been identified to date. In the context of tumours, two isoforms, carbonic anhydrase IX (CAIX) and carbonic anhydrase XII (CAXII) have been shown to associated with cancer progression, metastasis and impaired therapeutic response (McDonald et al., 2012, Oncotarget, 3(1): 84-97).

CAIX is a dimeric transmembrane protein. The extracellular portion of CAIX is separated from a short intracellular tail by a single pass transmembrane domain. CAIX contains a proteoglycan (PG)-like domain immediately adjacent to its catalytic domain (McDonald et al., 2012, Oncotarget, 3(1): 84-97). The sequence of human CAIX is known (mRNA sequence: GenBank ID BC014950, GI 15928967; amino acid sequence: GenBank ID AAH14950, GI 15928968). A CAIX homologue in mice has also been identified (mRNA sequence: GenBank ID BC120544, GI 111307266; amino acid sequence: GenBank ID AAI20545, GI 111307267).

Expression of CAIX in tumour cells is strongly induced during tumour hypoxia. Tumour hypoxia occurs when a tumour outgrows its blood supply during tumour growth, leaving portions of the tumor with regions where the oxygen concentration is significantly lower than in healthy tissues. Tumour hypoxia is a crucial factor in tumour physiology as it impacts on tumour biology, including genetic instability, angiogenesis, invasiveness, survival and metabolism. Metabolic changes induced by hypoxia can promote activities associated with aggressive tumour cell behaviour, such as survival, invasion and metastasis (McDonald et al., 2012, Oncotarget, 3(1): 84-97).

The reduced supply of oxygen in tumour hypoxia limits the capacity of tumour cells for oxidative phosphorylation as a means of generating energy resulting in a switch to glycolysis. The switch to glycolysis in turn results in increased production of and export of acidic metabolites to the extracellular space leading to a reduction in the extracellular pH. This extracellular acidification leads to disruption of the intracellular pH, giving a selective advantage to tumour cells that can survive under these conditions. CAIX plays an important part in the pH regulatory system of tumour cells needed to maintain a moderately alkaline intracellular pH while also creating an acidic extracellular environment (McDonald et al., 2012, Oncotarget, 3(1): 84-97).

CAIX is an attractive target for anti-cancer agents as it is overexpressed in many solid tumours but shows limited expression in normal tissues. Consequently, interference with CAIX is expected to have few, if any, significant consequences. In addition to the selective expression of CAIX in solid tumours, it has been demonstrated that there is a relationship between CAIX expression poor patient prognosis in many cancers. Cancers which have been shown to express CAIX include lung cancer, colon cancer, breast cancer, cervical cancer, bladder cancer, rectal cancer, ovarian cancer, brain cancer, head and neck cancer, oral cavity cancer and renal cancer. In addition, expression of CAIX has been shown to correlate with metastatic disease (McDonald et al., 2012, Oncotarget, 3(1): 84-97).

As a result of the selective expression of CAIX in tumours and its association with poor prognosis, detection of CAIX can be used not only for the diagnosis and detection of tumours but also as a marker for cancer prognosis. CAIX expression by tumour cells can be determined using immunohistochemical staining of tissue sections or by tissue microarray analysis, for example (McDonald et al., 2012, Oncotarget, 3(1): 84-97).

A number of CAIX inhibitors are known in the art, including monoclonal antibodies and small molecule inhibitors, and several of these are being investigated for cancer therapy applications. Known anti-CAIX antibodies include M75, G250, cG250 (a chimeric version of G250), A3 and CC7 (McDonald et al., 2012, Oncotarget, 3(1): 84-97; Ahlskog et al., British Journal of Cancer, 2009, 101:645-657). Antibodies specific for CAIX may interfere directly with CAIX activity, for example by targeting the catalytic domain of the enzyme or can be used to deliver therapeutic agents to the tumour cells. Antibody-based targeting of therapeutic agents to tumour cells is a promising strategy for cancer treatment, as it allows the controlled delivery the therapeutic agents directly to the site of the tumour. Targeted delivery may increase efficacy, reduce the dose of therapeutic agent needed to effect treatment, reduce exposure of normal tissues to the therapeutic agent, as well as damage resulting therefrom.

Although a number of CAIX inhibitors, including monoclonal antibodies specific for CAIX, have been identified and several are currently being investigated in clinical trials, no anti-CAIX-based therapies are currently available for the treatment of cancer patients. There thus remains a need in the art to develop further anti-cancer therapies, as well as diagnostic agents, which target CAIX.

STATEMENTS OF INVENTION

The present inventors have isolated an anti-CAIX antibody, XE114, which has a high affinity for CAIX and is expected to perform well in the treatment, diagnosis, detection and imaging of cancers expressing CAIX. The XE114 antibody binds to the extracellular domain of CAIX. The sequence of the XE114 antibody is shown in FIG. 1. XE114 has been shown to bind to a different epitope on CAIX than the known A3 anti-CAIX antibody.

Thus, in a first aspect, the present invention relates to a specific binding member, e.g. an antibody molecule or fragment thereof, comprising a VH domain comprising a framework and a set of complementarity determining regions HCDR1, HCDR2 and HCDR3, and a VL domain comprising a framework and a set of complementarity determining regions LCDR1, LCDR2 and LCDR3, wherein:

HCDR1 has the amino acid sequence set forth in SEQ ID NO: 1, or the amino acid sequence set forth in SEQ ID NO: 1 with five or fewer, four or fewer, three or fewer, two or fewer, or one amino acid substitutions, deletions or insertions, HCDR2 has the amino acid sequence set forth in SEQ ID NO: 2, or the amino acid sequence set forth in SEQ ID NO: 2 with five or fewer, four or fewer, three or fewer, two or fewer, or one amino acid substitutions, deletions or insertions, HCDR3 has the amino acid sequence set forth in SEQ ID NO: 3, or the amino acid sequence set forth in SEQ ID NO: 3 with five or fewer, four or fewer, three or fewer, two or fewer, or one amino acid substitutions, deletions or insertions, LCDR1 has the amino acid sequence set forth in SEQ ID NO: 4, or the amino acid sequence set forth in SEQ ID NO: 4 with five or fewer, four or fewer, three or fewer, two or fewer, or one amino acid substitutions, deletions or insertions, LCDR2 has the amino acid sequence set forth in SEQ ID NO: 5, or the amino acid sequence set forth in SEQ ID NO: 5 with five or fewer, four or fewer, three or fewer, two or fewer, or one amino acid substitutions, deletions or insertions, and LCDR3 has the amino acid sequence set forth in SEQ ID NO: 6, or the amino acid sequence set forth in SEQ ID NO: 6 with five or fewer, four or fewer, three or fewer, two or fewer, or one amino acid substitutions, deletions or insertions.

Asparagine (N)-linked glycosylation is an important post-translational modification that results in the covalent attachment of oligosaccharides onto asparagine residues in a protein sequence. The acceptor substance of N-glycosylation is an asparagine within the consensus sequence N-X-S/T, where X can be any amino acid except proline (Schwarz and Aebi, 2011 Curr Opin Struct Biol. 2011 21(5):576-82). As the LCDR3 of the XE114 antibody starts with an "NSS . . . " motif, the LCDR3 comprises a glycosylation site. In order to remove said glycosylation site, the amino acid at position 1 of the LCDR3 may be modified by substitution with another amino acid. For example, the amino acid at position 1 of the LCDR3 may be substituted with Glutamine (Q) or Alanine (A). Alternatively, in order to remove said glycosylation site, the amino acid at position 3 of the LCDR3 may be modified by substitution with another amino acid. For example, the serine (S) at position 3 of the LCDR3 may be substituted with an Alanine (A). In a preferred embodiment, the asparagine (N) at position 1 of the LCDR3 is substituted with glutamine (Q). Thus, in a preferred embodiment, the LCDR3 has the amino acid sequence set forth in SEQ ID NO: 19, or the amino acid sequence set forth in SEQ ID NO: 19 with five or fewer, four or fewer, three or fewer, two or fewer, or one amino acid substitutions, deletions or insertions.

In a preferred embodiment, the present invention therefore relates to a specific binding member, e.g. an antibody molecule or fragment thereof, comprising a VH domain comprising a framework and a set of complementarity determining regions HCDR1, HCDR2 and HCDR3, and a VL domain comprising a framework and a set of complementarity determining regions LCDR1, LCDR2 and LCDR3, wherein:

HCDR1 has the amino acid sequence set forth in SEQ ID NO: 1, or the amino acid sequence set forth in SEQ ID NO: 1 with five or fewer, four or fewer, three or fewer, two or fewer, or one amino acid substitutions, deletions or insertions, HCDR2 has the amino acid sequence set forth in SEQ ID NO: 2, or the amino acid sequence set forth in SEQ ID NO: 2 with five or fewer, four or fewer, three or fewer, two or fewer, or one amino acid substitutions, deletions or insertions, HCDR3 has the amino acid sequence set forth in SEQ ID NO: 3, or the amino acid sequence set forth in SEQ ID NO: 3 with five or fewer, four or fewer, three or fewer, two or fewer, or one amino acid substitutions, deletions or insertions, LCDR1 has the amino acid sequence set forth in SEQ ID NO: 4, or the amino acid sequence set forth in SEQ ID NO: 4 with five or fewer, four or fewer, three or fewer, two or fewer, or one amino acid substitutions, deletions or insertions, LCDR2 has the amino acid sequence set forth in SEQ ID NO: 5, or the amino acid sequence set forth in SEQ ID NO: 5 with five or fewer, four or fewer, three or fewer, two or fewer, or one amino acid substitutions, deletions or insertions, and LCDR3 has the amino acid sequence set forth in SEQ ID NO: 19, or the amino acid sequence set forth in SEQ ID NO: 19 with five or fewer, four or fewer, three or fewer, two or fewer, or one amino acid substitutions, deletions or insertions.

The invention also relates to a specific binding member, e.g. an antibody molecule, comprising a VH domain and a VL domain, wherein the VH domain has the amino acid sequence set forth in SEQ ID NO: 7 or a sequence having at least 90% sequence identity, e.g. at least 95%, 96%, 97%, 98% or 99% sequence identity, to SEQ ID NO: 7 and/or, wherein the VL domain has the amino acid sequence set forth in SEQ ID NO: 8 or a sequence having at least 90% sequence identity, e.g. at least 95%, 96%, 97%, 98% or 99% sequence identity, to SEQ ID NO: 8.

In a preferred embodiment, the invention relates to a specific binding member, e.g. an antibody molecule, comprising a VH domain and a VL domain, wherein the VH domain has the amino acid sequence set forth in SEQ ID NO: 7 or a sequence having at least 90% sequence identity, e.g. at least 95%, 96%, 97%, 98% or 99% sequence identity, to SEQ ID NO: 7 and/or, wherein the VL domain has the amino acid sequence set forth in SEQ ID NO: 20 or a sequence having at least 90% sequence identity, e.g. at least 95%, 96%, 97%, 98% or 99% sequence identity, to SEQ ID NO: 20.

Amino acid similarity and identity are generally defined with reference to the algorithm GAP (GCG Wisconsin Package™, Accelrys, San Diego Calif.). GAP uses the Needleman & Wunsch algorithm to align two complete sequences that maximizes the number of matches and minimizes the number of gaps. Generally, the default parameters are used, with a gap creation penalty=12 and gap extension penalty=4. Use of GAP may be preferred but other algorithms may be used, e.g. BLAST or TBLASTN(which use the method of Altschul et al. (1990) J. Mol. Biol. 215:

405-410), FASTA (which uses the method of Pearson and Lipman (1988) PNAS USA 85: 2444-2448), or the Smith-Waterman algorithm (Smith and Waterman (1981) J. Mol Biol. 147: 195-197), generally employing default parameters.

In a second aspect, the present invention relates to a specific binding member, e.g. an antibody molecule, that binds carbonic anhydrase IX (CAIX), wherein the specific binding member binds the same, or substantially the same, epitope on CAIX as the epitope bound by a binding member comprising a VH domain comprising a framework and a set of complementarity determining regions HCDR1, HCDR2 and HCDR3, and a VL domain comprising a framework and a set of complementarity determining regions LCDR1, LCDR2 and LCDR3, wherein:

HCDR1 has the amino acid sequence set forth in SEQ ID NO: 1,
HCDR2 has the amino acid sequence set forth in SEQ ID NO: 2,
HCDR3 has the amino acid sequence set forth in SEQ ID NO: 3,
LCDR1 has the amino acid sequence set forth in SEQ ID NO: 4,
LCDR2 has the amino acid sequence set forth in SEQ ID NO: 5, and
LCDR3 has the amino acid sequence set forth in SEQ ID NO: 6.

In a preferred embodiment, the specific binding member, e.g. an antibody molecule, that binds carbonic anhydrase IX (CAIX), is a specific binding member binds the same, or substantially the same, epitope on CAIX as the epitope bound by a binding member comprising a VH domain comprising a framework and a set of complementarity determining regions HCDR1, HCDR2 and HCDR3, and a VL domain comprising a framework and a set of complementarity determining regions LCDR1, LCDR2 and LCDR3, wherein:

HCDR1 has the amino acid sequence set forth in SEQ ID NO: 1,
HCDR2 has the amino acid sequence set forth in SEQ ID NO: 2,
HCDR3 has the amino acid sequence set forth in SEQ ID NO: 3,
LCDR1 has the amino acid sequence set forth in SEQ ID NO: 4,
LCDR2 has the amino acid sequence set forth in SEQ ID NO: 5, and
LCDR3 has the amino acid sequence set forth in SEQ ID NO: 19.

An epitope may be linear or conformational.

Methods of epitope mapping are known in the art and include surface plasmon resonance, such as Biacore, as described elsewhere herein, x-ray co-crystallography which allows the interaction between the antigen and antibody to be directly visualized, peptide-binding scanning, such as PepScan, in which a library of oligo-peptide sequences from overlapping and non-overlapping segments of a target protein is employed and tested for their ability to bind the antibody of interest, and site-directed mutagenesis in which systematic mutations of amino acids are introduced into a protein sequence followed by measurement of antibody binding in order to identify amino acids that comprise the epitope (such as alanine-scanning). These and other methods are well-known in the art (Ladner, Mapping the Epitopes of Antibodies, Biotechnology and Genetic Engineering Reviews, Vol. 24, 1-30, 2007).

For example, in a peptide-binding scan, such as the kind provided by PepScan Systems, short overlapping peptides derived from the antigen are systematically screened for binding to a binding member. The peptides may be covalently coupled to a support surface to form an array of peptides. Peptides may be in a linear or constrained conformation. A constrained conformation may be produced using peptides having a terminal Cys residue at each end of the peptide sequence. The Cys residues can be covalently coupled directly or indirectly to a support surface such that the peptide is held in a looped conformation. Thus, peptides used in the method may have Cys residues added to each end of a peptide sequence corresponding to a fragment of the antigen. Double looped peptides may also be used, in which a Cys residue is additionally located at or near the middle of the peptide sequence. The Cys residues can be covalently coupled directly or indirectly to a support surface such that the peptides form a double-looped conformation, with one loop on each side of the central Cys residue. Peptides can be synthetically generated, and Cys residues can therefore be engineered at desired locations, despite not occurring naturally in the CAIX protein sequence. Optionally, linear and constrained peptides may both be screened in a peptide-binding assay. A peptide-binding scan may involve identifying (e.g. using ELISA) a set of peptides to which the binding member binds, wherein the peptides have amino acid sequences corresponding to fragments of SEQ ID NO: 17 (e.g. peptides of about 5, 10 or 15 contiguous residues of SEQ ID NO: 17, and aligning the peptides in order to determine a footprint of residues bound by the binding member, where the footprint comprises residues common to overlapping peptides.

The invention also relates to a specific binding member, e.g. an antibody molecule, that inhibits binding to CAIX of a binding member comprising a VH domain comprising a framework and a set of complementarity determining regions HCDR1, HCDR2 and HCDR3, and a VL domain comprising a framework and a set of complementarity determining regions LCDR1, LCDR2 and LCDR3, wherein:

HCDR1 has the amino acid sequence of SEQ ID NO: 1,
HCDR2 has the amino acid sequence of SEQ ID NO: 2,
HCDR3 has the amino acid sequence of SEQ ID NO: 3,
LCDR1 has the amino acid sequence of SEQ ID NO: 4,
LCDR2 has the amino acid sequence of SEQ ID NO: 5, and
LCDR3 has the amino acid sequence of SEQ ID NO: 6.

In a preferred embodiment, the invention relates to a specific binding member, e.g. an antibody molecule, that inhibits binding to CAIX of a binding member comprising a VH domain comprising a framework and a set of complementarity determining regions HCDR1, HCDR2 and HCDR3, and a VL domain comprising a framework and a set of complementarity determining regions LCDR1, LCDR2 and LCDR3, wherein:

HCDR1 has the amino acid sequence of SEQ ID NO: 1,
HCDR2 has the amino acid sequence of SEQ ID NO: 2,
HCDR3 has the amino acid sequence of SEQ ID NO: 3,
LCDR1 has the amino acid sequence of SEQ ID NO: 4,
LCDR2 has the amino acid sequence of SEQ ID NO: 5, and
LCDR3 has the amino acid sequence of SEQ ID NO: 19.

Methods for determining whether a first antibody is capable of inhibiting binding of a second antibody to a target antigen, for example because the antibodies bind to overlapping epitopes, are known in the art and include cross-blocking assays, such as competitive enzyme-linked immunosorbent assays (ELISA). These assays are well-known in the art (Ladner, Biotechnology and Genetic Engineering Reviews, Vol. 24, 1-30, 2007).

For example, in order to identify a specific binding member, e.g. an antibody molecule, that inhibits binding to CAIX of a specific binding member, e.g. antibody molecule, of the present invention through a competitive ELISA, the antibody of the present invention may be immobilized in wells of a multi-well plate. The CAIX antigen may then added to the wells, followed by washing to remove any unbound antigen. A second anti-CAIX antibody labelled with a detectable label may then added to the wells, followed by washing to remove any unbound antibody. Binding of the second anti-CAIX antibody to the CAIX antigen may then be detected through detection of the detectable label. If the second anti-CAIX antibody molecule is unable to bind the CAIX antigen, this demonstrates that the second anti-CAIX antibody molecule is capable of inhibiting binding of the antibody molecule of the invention to CAIX.

The present invention further provides a specific binding member of the invention, for use in a method of treatment. Also provided is a method of treating a patient, wherein the method comprises administering to the patient a therapeutically effective amount of a specific binding member according to the invention. Further provided is the use of a specific binding member or antibody molecule according to the invention for use in the manufacture of a medicament. A patient, as referred to herein, is preferably a human patient.

In another aspect, the invention relates to a specific binding member of the invention for use in a method of treating of cancer. The invention also provides the use of a specific binding member of the invention for the preparation of a medicament for treating cancer. The invention also provides a method of treating cancer in a patient, the method comprising administering to the patient a therapeutically effective amount of a medicament comprising a specific binding member of the invention. Preferably, the specific binding member is an antibody molecule.

In further aspect, the invention relates to a specific binding member of the invention for use in the delivery to sites of cancer in a patient of a molecule conjugated to the specific binding member. The invention also provides a method of delivering a molecule to sites of cancer in a patient, the method comprising administering a specific binding member of the invention to the patient, wherein the molecule is conjugated to the binding member. Preferably, the specific binding member is an antibody molecule.

In a yet further aspect, the invention relates to a specific binding member of the invention for use in a method of imaging, detection, or diagnosis of cancer. The invention also provides the use of a specific binding member of the invention for the preparation of a diagnostic product for imaging, diagnosing, or detecting cancer. The invention further provides a method of imaging, detecting, or diagnosing cancer expressing CAIX in a human or animal comprising the steps of:

(i) administering to the human or animal a specific binding member of the invention;
(ii) determining the presence or absence of the specific binding member in the human or animal body;

wherein the detection of the specific binding member in the human or animal body indicates the presence of a cancer expressing CAIX. The specific binding member is preferably an antibody molecule.

The cancer may be selected from the group consisting of: lung cancer, colon cancer, breast cancer, cervical cancer, bladder cancer, rectal cancer, ovarian cancer, brain cancer, head and neck cancer, oral cavity cancer and kidney cancer.

Preferably, the cancer is lung cancer, colon cancer, breast cancer, cervical cancer, bladder cancer, rectal cancer, ovarian cancer, brain cancer, head and neck cancer, oral cavity cancer and kidney cancer, wherein the cancer expresses, e.g. overexpresses, or has been determined to express, CAIX.

The specific binding member, e.g. antibody molecule, of the invention may be conjugated to a detectable label, a radioisotope, e.g. a therapeutic radioisotope, a cytotoxic drug, or to a molecule that has biocidal or cytotoxic activity. The specific binding member may be conjugated to the radioisotope, cytotoxic drug, or molecule that has biocidal or cytotoxic activity via a cleavable linker. In the context of cancer treatment, the specific binding member of the invention may be conjugated to a radioisotope, e.g. a therapeutic radioisotope, or molecule that has biocidal or cytotoxic activity, e.g. a cytotoxic drug. In the context of cancer imaging, detection, or diagnosis, the specific binding member of the invention may be conjugated a detectable label. The detectable label may be a radioisotope, e.g. a non-therapeutic radioisotope.

In a preferred embodiment, the specific binding member is conjugated to interleukin 2 (IL2) and a tumour necrosis factor, such as tumour necrosis factor alpha (TNFα). The format and construction of such conjugates is described in WO2016/180715. In a more preferred embodiment, the TNF is a mutant TNF, such as a mutant TNFα which has reduced activity. The use of a reduced activity tumour necrosis factor (TNF) mutant has been shown to improve the tolerability of a dual immunocytokine that comprises TNF and IL2, as well as a specific binding member, without affecting efficacy. The format and construction of such conjugates is described in WO2018/087172. The conjugates may be used, for example, in the treatment of cancer.

The specific binding member conjugated to IL2 and TNF may be in the form of an scFv or a diabody, but most preferably is in the form of an scFv.

The toxicity of a conjugate comprising a TNF mutant may be reduced compared to the corresponding conjugate comprising wild-type TNF. Reduced toxicity may include improved tolerability in a patient, for example a reduction in one or more adverse symptoms associated with administration of the conjugate(s) to the patient. Adverse symptoms reduced by the toxicity may include weight loss, nausea, vomiting, fever, chills, flushing, urticaria, rash, pulmonary toxicity, dyspnea, hypotension, anaphylaxis, serum sickness, increased creatinine, headache.

Furthermore, the reduced toxicity of the TNF mutant in the conjugate increases the synergistic effect of the IL2 moiety, which can be administered at a higher dose due to the lower activity of the TNF mutant. The potency matched cytokines in the conjugate may therefore be useful in therapeutic applications.

An aspect of the invention therefore provides a conjugate as described above for use in a method of treating cancer by targeting IL2 and a TNF mutant, preferably a TNFα mutant, to the tumour in vivo, as well as a conjugate described herein for use in a method of delivering IL2 and a TNF mutant, preferably a TNFα mutant, to the tumour in a patient.

Another aspect of the invention provides a method of treating cancer by targeting IL2 and a TNF mutant, preferably a TNFα mutant, to the tumour in a patient, the method comprising administering a therapeutically effective amount of a conjugate as described above to the patient, as well as a method of delivering IL2 and a TNF mutant, preferably a TNFα mutant, to the tumour in a patient comprising administering to the patient a conjugate as describe above.

In addition, another aspect of the invention provides the use of a conjugate as described above for the preparation of a medicament for the treatment of cancer. The use of a conjugate as described above for the preparation of a medicament for delivery of IL2 and a TNF mutant, preferably a TNFα mutant, to the neovasculature of a tumour is similarly contemplated.

A specific binding member of the invention may be an antibody molecule which binds CAIX, e.g. the extracellular domain of CAIX, wherein the antibody comprises one or more complementarity determining regions (CDRs) of the XE114 antibody described herein. These sequences are provided below (see SEQ ID NOs: 1-6, or preferably, SEQ ID NOs: 1-5 and SEQ ID NO: 19). The CDR sequences of the XE114 antibody with the glycosylation motif in the VL domain are also shown in FIG. 1.

A specific binding member of the invention may comprise one or more CDRs as described herein, e.g. a CDR3, and optionally also a CDR1 and CDR2 to form a set of CDRs.

Preferably, a specific binding member of the invention comprises a set of heavy chain and/or light chain CDRs of antibody XE114 described herein with ten or fewer, e.g. one, two, three, four, or five, amino acid substitutions within the disclosed set of heavy chain and/or light chain CDRs.

Substitutions may potentially be made at any residue within the set of CDRs, and may be within CDR1, CDR2 and/or CDR3.

A specific binding member of the invention may comprise an antibody molecule, e.g. a human antibody molecule. The specific binding member normally comprises an antibody VH and/or VL domain. VH domains of specific binding members are also provided for use in the invention. Within each of the VH and VL domains are complementarity determining regions, ("CDRs"), and framework regions, ("FRs"). A VH domain comprises a set of HCDRs, and a VL domain comprises a set of LCDRs. An antibody molecule may comprise an antibody VH domain comprising a VH CDR1, CDR2 and CDR3 and a framework. It may alternatively or also comprise an antibody VL domain comprising a VL CDR1, CDR2 and CDR3 and a framework. All VH and VL sequences, CDR sequences, sets of CDRs and sets of HCDRs and sets of LCDRs disclosed herein represent embodiments of a specific binding member for use in the invention. As described herein, a "set of CDRs" comprises CDR1, CDR2 and CDR3. Thus, a set of HCDRs refers to HCDR1, HCDR2 and HCDR3, and a set of LCDRs refers to LCDR1, LCDR2 and LCDR3. Unless otherwise stated, a "set of CDRs" includes HCDRs and LCDRs.

A specific binding member of the invention may comprise an antibody VH domain comprising complementarity determining regions HCDR1, HCDR2 and HCDR3 and a framework, wherein HCDR1 is SEQ ID NO: 1, and wherein optionally HCDR2 is SEQ ID NO: 2, and/or HCDR3 is SEQ ID NO: 3.

Typically, a VH domain is paired with a VL domain to provide an antibody antigen-binding site, although as discussed further below, a VH or VL domain alone may be used to bind antigen. Thus, a specific binding member of the invention may further comprise an antibody VL domain comprising complementarity determining regions LCDR1, LCDR2 and LCDR3 and a framework, wherein LCDR1 is SEQ ID NO: 4, and wherein optionally LCDR2 is SEQ ID NO: 5 and/or LCDR3 is SEQ ID NO: 6.

Preferably, the specific binding member of the invention further comprises an antibody VL domain comprising complementarity determining regions LCDR1, LCDR2 and LCDR3 and a framework, wherein LCDR1 is SEQ ID NO: 4, and wherein optionally LCDR2 is SEQ ID NO: 5 and/or LCDR3 is SEQ ID NO: 19.

A specific binding member of the invention may comprise an antibody molecule which binds to CAIX, wherein the antibody molecule comprises a VH domain and a VL domain, wherein the VH domain comprises a framework and a set of complementarity determining regions HCDR1, HCDR2 and HCDR3 and wherein the VL domain comprises complementarity determining regions LCDR1, LCDR2 and LCDR3 and a framework, and wherein
  HCDR1 has amino acid sequence SEQ ID NO: 1;
  HCDR2 has amino acid sequence SEQ ID NO: 2;
  HCDR3 has amino acid sequence SEQ ID NO: 3;
  LCDR1 has amino acid sequence SEQ ID NO: 4;
  LCDR2 has amino acid sequence SEQ ID NO: 5; and
  LCDR3 has amino acid sequence SEQ ID NO: 6.

Preferably, the specific binding member of the invention comprises an antibody molecule which binds to CAIX, wherein the antibody molecule comprises a VH domain and a VL domain, wherein the VH domain comprises a framework and a set of complementarity determining regions HCDR1, HCDR2 and HCDR3 and wherein the VL domain comprises complementarity determining regions LCDR1, LCDR2 and LCDR3 and a framework, and wherein
  HCDR1 has amino acid sequence SEQ ID NO: 1;
  HCDR2 has amino acid sequence SEQ ID NO: 2;
  HCDR3 has amino acid sequence SEQ ID NO: 3;
  LCDR1 has amino acid sequence SEQ ID NO: 4;
  LCDR2 has amino acid sequence SEQ ID NO: 5; and
  LCDR3 has amino acid sequence SEQ ID NO: 19.

One or more CDRs or a set of CDRs of an antibody may be grafted into a framework (e.g. human framework) to provide an antibody molecule for use in the invention. Framework regions may comprise human germline gene segment sequences. Thus, the framework may be germlined, whereby one or more residues within the framework are changed to match the residues at the equivalent position in the most similar human germline framework. A specific binding member of the invention may be an isolated antibody molecule having a VH domain comprising a set of HCDRs in a human germline framework, preferably DP47 (Tomlinson et al., (1992) J. Mol. Biol., 227:776-798). Normally the specific binding member also has a VL domain comprising a set of LCDRs, e.g. in a human germline framework, preferably DPL16 (Williams et al., (1996) J Mol Biol:264, 220-232).

A specific binding member of the invention preferably is or comprises a single chain Fv (scFv), comprising a VH domain and a VL domain joined via a peptide linker. More preferably, the specific binding member of the invention is an scFv. The VH domain and VL domain may have the amino acid sequence shown in SEQ ID NO: 7 and SEQ ID NO: 8, respectively, but preferably have the amino acid sequence shown in SEQ ID NO: 7 and SEQ ID NO: 20, respectively. The skilled person may select an appropriate length and sequence of linker, e.g. at least 10 amino acids in length, up to about 15, up to about 20 or up to about 25 amino acids in length. The linker may have the amino acid sequence of SEQ ID NO: 9. The specific binding member of the present invention in scFv format may comprise or consist of the sequence shown in SEQ ID NO: 10, but preferably comprises or consists of the sequence shown in SEQ ID NO: 35.

A single chain Fv (scFv) may be comprised within a mini-immunoglobulin or small immunoprotein (SIP), e.g. as described in (Li et al., (1997), Protein Engineering, 10:

731-736). A SIP may comprise an scFv molecule fused to the CH4 domain of the human IgE secretory isoform IgE-S2 ($\varepsilon_{S2}$-CH4; Batista et al., (1996), J. Exp. Med., 184: 2197-205) forming an homo-dimeric mini-immunoglobulin antibody molecule.

A specific binding member of the invention may be or comprise a diabody (DB), comprising a VH domain and a VL domain joined via a peptide linker. Diabodies are described in WO94/13804 and Holliger et al. (1993a), Proc. Natl. Acad. Sci. USA 90 6444-6448. The VH domain and VL domain may have the amino acid sequence shown in SEQ ID NO: 7 and SEQ ID NO: 8, respectively, but preferably have the amino acid sequence shown in SEQ ID NO: 7 and SEQ ID NO: 20, respectively. The skilled person may select an appropriate length and sequence of linker. E.g. the linker may be 10 amino acids in length or less, 9 amino acids in length or less, 8 amino acids in length or less, 7 amino acids in length or less, 6 amino acids in length or less, or 5 or amino acids in length or less. The linker may be at least 5 amino acids in length. For example, the linker may have the sequence set forth in SEQ ID NO: 18.

Alternatively, the specific binding member of the invention may be an immunoglobulin G (IgG) molecule, preferably a human IgG molecule, such as IgG1, IgG2, IgG3 and IgG4, most preferably human IgG1.

In this case, the specific binding member of the invention may comprise a heavy chain and a light chain having the amino acid sequence shown in SEQ ID NO: 21 and SEQ ID NO: 22, respectively, but preferably comprises a heavy chain and a light chain having the amino acid sequence shown in SEQ ID NO: 21 and SEQ ID NO: 23, respectively.

The present invention also provides a nucleic acid encoding a specific binding member, or conjugate, of the invention, as well as a vector comprising such a nucleic acid.

A recombinant host cell comprising a nucleic acid or the vector of the invention is also provided. Such a recombinant host cell may be used to produce a specific binding member, or conjugate, of the invention. Thus, also provided is a method of producing a specific binding member of the invention, the method comprising culturing the recombinant host cell under conditions for production of the specific binding member. The method may further comprise a step of isolating and/or purifying the specific binding member.

The specific binding members of the present invention are expected to find application in therapeutic applications, in particular therapeutic applications in humans, such as cancer treatment as described above. Thus, also provided is a pharmaceutical composition comprising a specific binding member of the present invention and a pharmaceutically acceptable excipient.

Thus, the present invention provides:

[1] A specific binding member that binds carbonic anhydrase IX (CAIX), wherein:
(i) the specific binding member binds the same, or substantially the same, epitope on CAIX as the epitope bound by a binding member comprising a VH domain comprising a framework and a set of complementarity determining regions HCDR1, HCDR2 and HCDR3, and a VL domain comprising a framework and a set of complementarity determining regions LCDR1, LCDR2 and LCDR3, wherein:
HCDR1 has the amino acid sequence of SEQ ID NO: 1,
HCDR2 has the amino acid sequence of SEQ ID NO: 2,
HCDR3 has the amino acid sequence of SEQ ID NO: 3,
LCDR1 has the amino acid sequence of SEQ ID NO: 4,
LCDR2 has the amino acid sequence of SEQ ID NO: 5, and
LCDR3 has the amino acid sequence of SEQ ID NO: 19;
or
(ii) the specific binding member inhibits binding to CAIX of a binding member comprising a VH domain comprising a framework and a set of complementarity determining regions HCDR1, HCDR2 and HCDR3, and a VL domain comprising a framework and a set of complementarity determining regions LCDR1, LCDR2 and LCDR3, wherein:
HCDR1 has the amino acid sequence of SEQ ID NO: 1,
HCDR2 has the amino acid sequence of SEQ ID NO: 2,
HCDR3 has the amino acid sequence of SEQ ID NO: 3,
LCDR1 has the amino acid sequence of SEQ ID NO: 4,
LCDR2 has the amino acid sequence of SEQ ID NO: 5, and
LCDR3 has the amino acid sequence of SEQ ID NO: 19;
(iii) the specific binding member comprises a VH domain comprising a framework and a set of complementarity determining regions HCDR1, HCDR2 and HCDR3, and a VL domain comprising a framework and a set of complementarity determining regions LCDR1, LCDR2 and LCDR3, wherein:
HCDR1 has the amino acid sequence of SEQ ID NO: 1, or the amino acid sequence of SEQ ID NO: 1 with five or fewer amino acid substitutions, deletions or insertions,
HCDR2 has the amino acid sequence of SEQ ID NO: 2, or the amino acid sequence of SEQ ID NO: 2 with five or fewer amino acid substitutions, deletions or insertions,
HCDR3 has the amino acid sequence of SEQ ID NO: 3, or the amino acid sequence of SEQ ID NO: 3 with five or fewer amino acid substitutions, deletions or insertions,
LCDR1 has the amino acid sequence of SEQ ID NO: 4, or the amino acid sequence of SEQ ID NO: 4 with five or fewer amino acid substitutions, deletions or insertions,
LCDR2 has the amino acid sequence of SEQ ID NO: 5, or the amino acid sequence of SEQ ID NO: 5 with five or fewer amino acid substitutions, deletions or insertions, and
LCDR3 has the amino acid sequence of SEQ ID NO: 19, or the amino acid sequence of SEQ ID NO: 19 with five or fewer amino acid substitutions, deletions or insertions; or
(iv) the specific binding member comprises a VH domain and a VL domain, wherein the VH domain has the amino acid sequence of SEQ ID NO: 7 or a sequence having at least 90% sequence identity to SEQ ID NO: 7 and/or, wherein the VL domain has the amino acid sequence of SEQ ID NO: 20 or a sequence having at least 90% sequence identity to SEQ ID NO: 20.

[2] A specific binding member that binds carbonic anhydrase IX (CAIX), wherein:
(i) the specific binding member binds the same, or substantially the same, epitope on CAIX as the epitope bound by a binding member comprising a VH domain comprising a framework and a set of complementarity determining regions HCDR1, HCDR2 and HCDR3, and a VL domain comprising a framework and a set of complementarity determining regions LCDR1, LCDR2 and LCDR3, wherein:
HCDR1 has the amino acid sequence of SEQ ID NO: 1,
HCDR2 has the amino acid sequence of SEQ ID NO: 2,
HCDR3 has the amino acid sequence of SEQ ID NO: 3,
LCDR1 has the amino acid sequence of SEQ ID NO: 4,
LCDR2 has the amino acid sequence of SEQ ID NO: 5, and
LCDR3 has the amino acid sequence of SEQ ID NO: 6;
or (ii) the specific binding member inhibits binding to CAIX of a binding member comprising a VH domain comprising a framework and a set of complementarity determining regions HCDR1, HCDR2 and HCDR3, and a VL domain comprising a framework and a set of complementarity determining regions LCDR1, LCDR2 and LCDR3, wherein:
HCDR1 has the amino acid sequence of SEQ ID NO: 1,
HCDR2 has the amino acid sequence of SEQ ID NO: 2,
HCDR3 has the amino acid sequence of SEQ ID NO: 3,
LCDR1 has the amino acid sequence of SEQ ID NO: 4,
LCDR2 has the amino acid sequence of SEQ ID NO: 5, and
LCDR3 has the amino acid sequence of SEQ ID NO: 6;
(iii) the specific binding member comprises a VH domain comprising a framework and a set of complementarity determining regions HCDR1, HCDR2 and HCDR3, and a VL domain comprising a framework and a set of complementarity determining regions LCDR1, LCDR2 and LCDR3, wherein:
HCDR1 has the amino acid sequence of SEQ ID NO: 1, or the amino acid sequence of SEQ ID NO: 1 with five or fewer amino acid substitutions, deletions or insertions,
HCDR2 has the amino acid sequence of SEQ ID NO: 2, or the amino acid sequence of SEQ ID NO: 2 with five or fewer amino acid substitutions, deletions or insertions,
HCDR3 has the amino acid sequence of SEQ ID NO: 3, or the amino acid sequence of SEQ ID NO: 3 with five or fewer amino acid substitutions, deletions or insertions,
LCDR1 has the amino acid sequence of SEQ ID NO: 4, or the amino acid sequence of SEQ ID NO: 4 with five or fewer amino acid substitutions, deletions or insertions,
LCDR2 has the amino acid sequence of SEQ ID NO: 5, or the amino acid sequence of SEQ ID NO: 5 with five or fewer amino acid substitutions, deletions or insertions, and
LCDR3 has the amino acid sequence of SEQ ID NO: 6, or the amino acid sequence of SEQ ID NO: 6 with five or fewer amino acid substitutions, deletions or insertions; or
(iv) the specific binding member comprises a VH domain and a VL domain, wherein the VH domain has the amino acid sequence of SEQ ID NO: 7 or a sequence having at least 90% sequence identity to SEQ ID NO: 7 and/or, wherein the VL domain has the amino acid sequence of SEQ ID NO: 8 or a sequence having at least 90% sequence identity to SEQ ID NO: 8.

[3] The specific binding member according to [1] or [2], wherein the specific binding member binds to the extracellular domain CAIX.

[4] The specific binding member according to [3], wherein the extracellular domain of CAIX has the sequence of SEQ ID NO: 16.

[5] The specific binding member according to any one of [1] to [4], wherein the VH domain framework and/or the VL domain framework is a human germline framework.

[6] The specific binding member according to [1] or any one of [3] to [5], wherein the HCDR1 has the amino acid sequence of SEQ ID NO: 1, the HCDR2 has the amino acid sequence of SEQ ID NO: 2, the HCDR3 has the amino acid sequence of SEQ ID NO: 3, the LCDR1 has the amino acid sequence of SEQ ID NO: 4, the LCDR2 has the amino acid sequence of SEQ ID NO: 5, and the LCDR3 has the amino acid sequence of SEQ ID NO: 19.

[7] The specific binding member according to any one of [2] to [5], wherein the HCDR1 has the amino acid sequence of SEQ ID NO: 1, the HCDR2 has the amino acid sequence of SEQ ID NO: 2, the HCDR3 has the amino acid sequence of SEQ ID NO: 3, the LCDR1 has the amino acid sequence of SEQ ID NO: 4, the LCDR2 has the amino acid sequence of SEQ ID NO: 5, and the LCDR3 has the amino acid sequence of SEQ ID NO: 6.

[8] The specific binding member according to any one of [1] or any one of [3] to [6], wherein the VH domain has the amino acid sequence of SEQ ID NO: 7 and/or the VL domain has the amino acid sequence of SEQ ID NO: 20.

[9] The specific binding member according to any one of [2] to [5] or [7], wherein the VH domain has the amino acid sequence of SEQ ID NO: 7 and/or the VL domain has the amino acid sequence of SEQ ID NO: 8.

[10] The specific binding member according to any one of [1] to [9], wherein the specific binding member is an antibody molecule.

[11] The specific binding member according to any one of [1] to [10], wherein the binding member is or comprises a single chain Fv (scFv), or is an immunoglobulin G (IgG).

[12] The specific binding member according to [11], wherein the binding member is a small immunoprotein (SIP), or a diabody.

[13] The specific binding member according to any one of [1] to [12], wherein the binding member is conjugated to a detectable label.

[14] The specific binding member according to any one of [1] to [12], wherein the binding member is conjugated to a biocidal molecule, a cytotoxic molecule, or a radioisotope, optionally via a cleavable linker.

[15] The specific binding member according to any one of [1] to [12], wherein the binding member is conjugated to interleukin-2 (IL2), and a tumour necrosis factor (TNF) mutant, wherein the TNF mutant has reduced activity relative to the wild type TNF.

[16] A specific binding member according to any one of [1] to [12], [14] or [15] for use in a method of treating of cancer.

[17] A specific binding member according to any one of [1] to [13] for use in a method of imaging, detection, or diagnosis of cancer.

[18] A specific binding member according to any one of [1] to [12] for use in the delivery to sites of cancer in a patient of a molecule conjugated to the specific binding member.

[19] A specific binding member for use according to [18], wherein the molecule is a detectable label.

[20] A specific binding member for use according to [18], wherein the molecule is a biocidal molecule, a cytotoxic molecule, or a radioisotope.

[21] A specific binding member for use according to any one of [16] to [20], wherein the cancer is renal cell carcinoma.

[22] A specific binding member for use according to any one of [16] to [21], wherein the cancer expresses, or has been determined to express, CAIX.

[23] The use of a specific binding member according to any one of [1] to [12], [14] or [15] for the preparation of a medicament for treating cancer.

[24] The use of a specific binding member according to any one of [1] to [13] for the preparation of a diagnostic product for imaging, diagnosing, or detecting cancer.

[25] The use of any one of [23] to [24], wherein the cancer is renal cell carcinoma.

[26] The use of any one of [23] to [25], wherein the cancer expresses, or has been determined to express, CAIX.

[27] A method of treating cancer in a patient, the method comprising administering to the patient a therapeutically effective amount of a medicament comprising a specific binding member according to any one of [1] to [12], [14] or [15].

[28] A method of imaging, detecting, or diagnosing cancer expressing CAIX in a human or animal comprising the steps of:
  (i) administering to the human or animal a specific binding member according to any one of [1] to [13];
  (ii) determining the presence or absence of the specific binding member in the human or animal body;
  wherein the detection of the specific binding member in the human or animal body indicates the presence of a cancer expressing CAIX.

[29] A method of delivering a molecule to sites of cancer in a patient, the method comprising administering a specific binding member according to any one of [1] to [12] to the patient, wherein the molecule is conjugated to the binding member.

[30] The method according to [29], wherein the molecule is a detectable label.

[31] The method according to [29], wherein the molecule is a biocidal molecule, a cytotoxic molecule, or a radioisotope.

[32] The method according to any one of [27] to [31], wherein the cancer is renal cell carcinoma.

[33] The method according to any one of [27] to [32], wherein the cancer expresses, or has been determined to express, CAIX.

[34] A nucleic acid encoding a specific binding member according to any one of [1] to [12].

[35] A vector comprising the nucleic acid of [34].

[36] A recombinant host cell comprising the nucleic acid of [34], or the vector of [35].

[37] A method of producing a specific binding member according to any one of [1] to [12], comprising culturing the recombinant host cell of [36] under conditions for production of the specific binding 35 member or antibody molecule.

[38] The method of [37] further comprising isolating and/or purifying the specific binding member.

[39] A pharmaceutical composition comprising a specific binding member or antibody molecule according to any one of [1] to [15] and a pharmaceutically acceptable excipient.

These and other aspects of the invention are described in further detail below.

BRIEF DESCRIPTION OF THE FIGURES

FIG. 1A shows the sequence of the XE114 anti-CAIX antibody heavy chain variable domain (VH) (SEQ ID NO: 7). The amino acid sequence of the heavy chain CDR1 (SEQ ID NO: 1) of the anti-CAIX XE114 antibody is underlined. The amino acid sequence of the heavy chain CDR2 (SEQ ID NO: 2) of the anti-CAIX XE114 antibody is shown in italics and underlined. The amino acid sequence of the heavy chain CDR3 (SEQ ID NO: 3) of anti-CAIX XE114 antibody is shown in bold and underlined. FIG. 1B shows the amino acid sequence of the anti-CAIX XE114 antibody linker sequence between the VH and VL domains (SEQ ID NO: 9). FIG. 1C shows the amino acid sequences of the anti-CAIX XE114 antibody light chain variable domain (VL) with the glycosylation motif (SEQ ID NO: 8). The amino acid sequence of the light chain CDR1 (SEQ ID NO: 4) of the anti-CAIX XE114 antibody is underlined. The amino acid sequence of the light chain CDR2 (SEQ ID NO: 5) of the anti-CAIX XE114 antibody is shown in italics and underlined. The amino acid sequence of the light chain CDR3 (SEQ ID NO: 6) of the anti-CAIX XE114 antibody is shown in bold and underlined.

FIG. 3 demonstrates that antibody XE114 binds to an epitope on CAIX distinct from the epitope bound by anti-CAIX antibody A3.

FIG. 4 demonstrates that the XE114 antibody specifically and strongly stained the SKRC52 tumor tissue, while no staining of the tumour tissue was observed with the control antibody.

FIG. 5 demonstrates that the XE114 antibody specifically accumulated at the tumor site, while no such accumulation was seen with the control antibody.

FIG. 6 demonstrates that the XE114 antibody strongly stained the stomach tissue, which is in line with reported pattern of expression of CAIX.

FIG. 8 demonstrates that the XE114 antibody was selectively taken up into the SKRC52 tumors and displayed an optimal tumor to organs and tumor to blood ratio.

Figure 11:
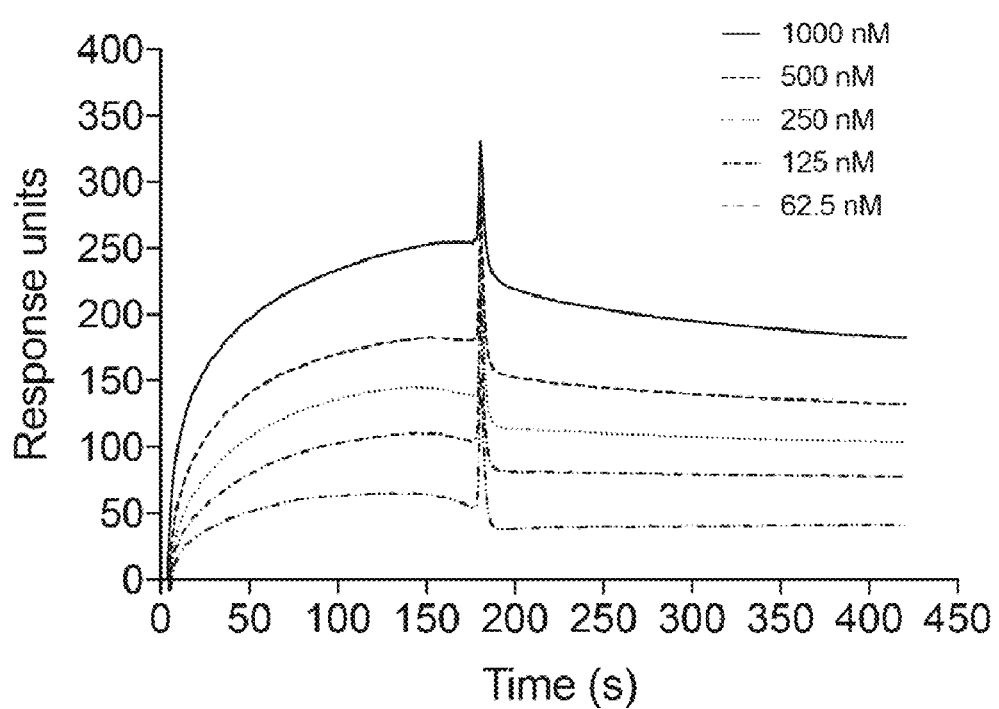

FIG. 11 shows the results of a Biacore analysis to measure the affinity of the hIL2-XE114-hTNF$^{mut}$ conjugate (without the glycosylation motif) for the extracellular domain of CAIX.

Figure 12:
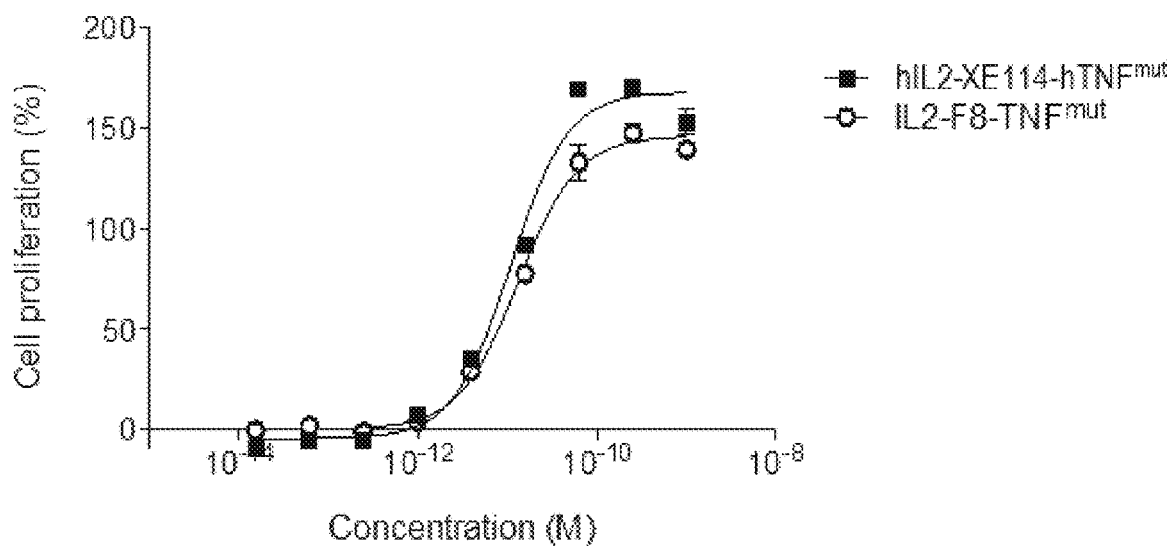
Figure 12:
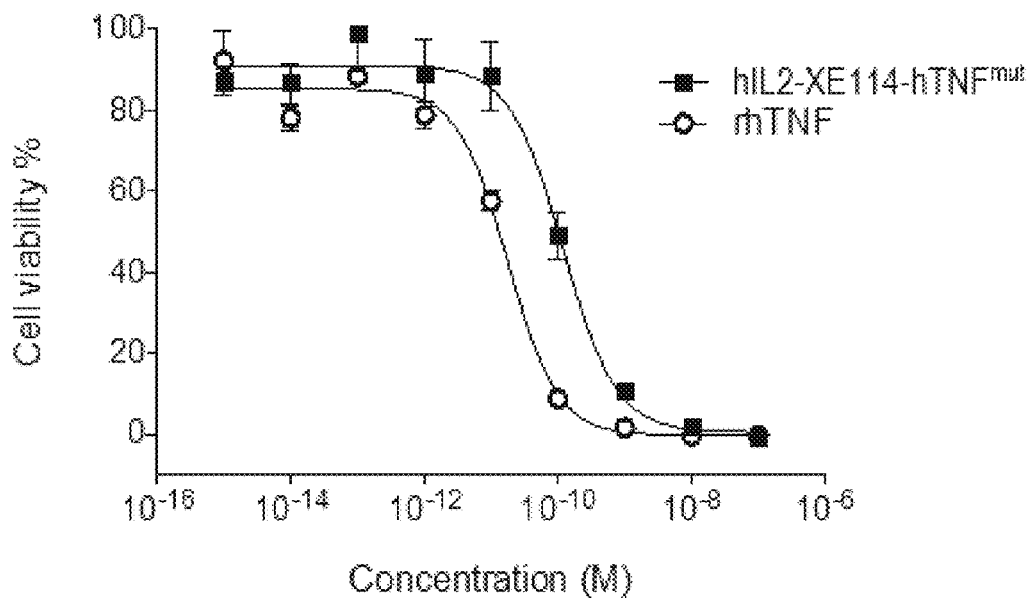

FIG. 12 shows the results of hIL2-XE114-hTNF$^{mut}$ (without the glycosylation motif) when tested in (A) an IL2 bioactivity assay, based on the proliferation of CTLL-2 cells and (B) a TNF bioactivity assay, based on the killing of L-M fibroblast cells.

Figure 13:
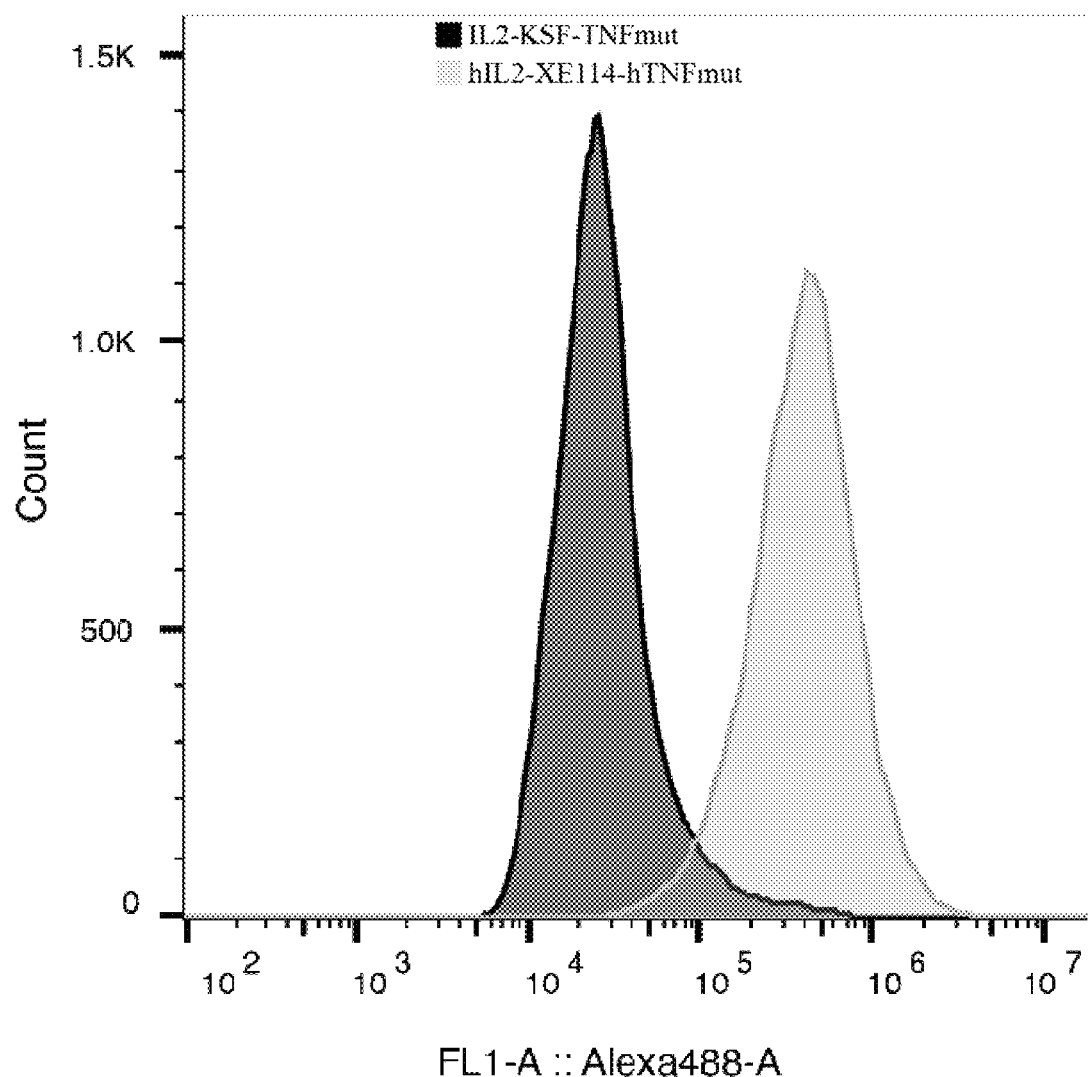

FIG. 13 shows the flow cytometric evaluation of CAIX expression on SKRC52 cells, stained with hIL2-XE114-hTNF$^{mut}$ (without the glycosylation motif) and IL2-KSF-TNF$^{mut}$ (negative control) conjugates and detected with a rat anti-IL2 followed by staining with anti-rat AlexaFluor488.

Figure 14:
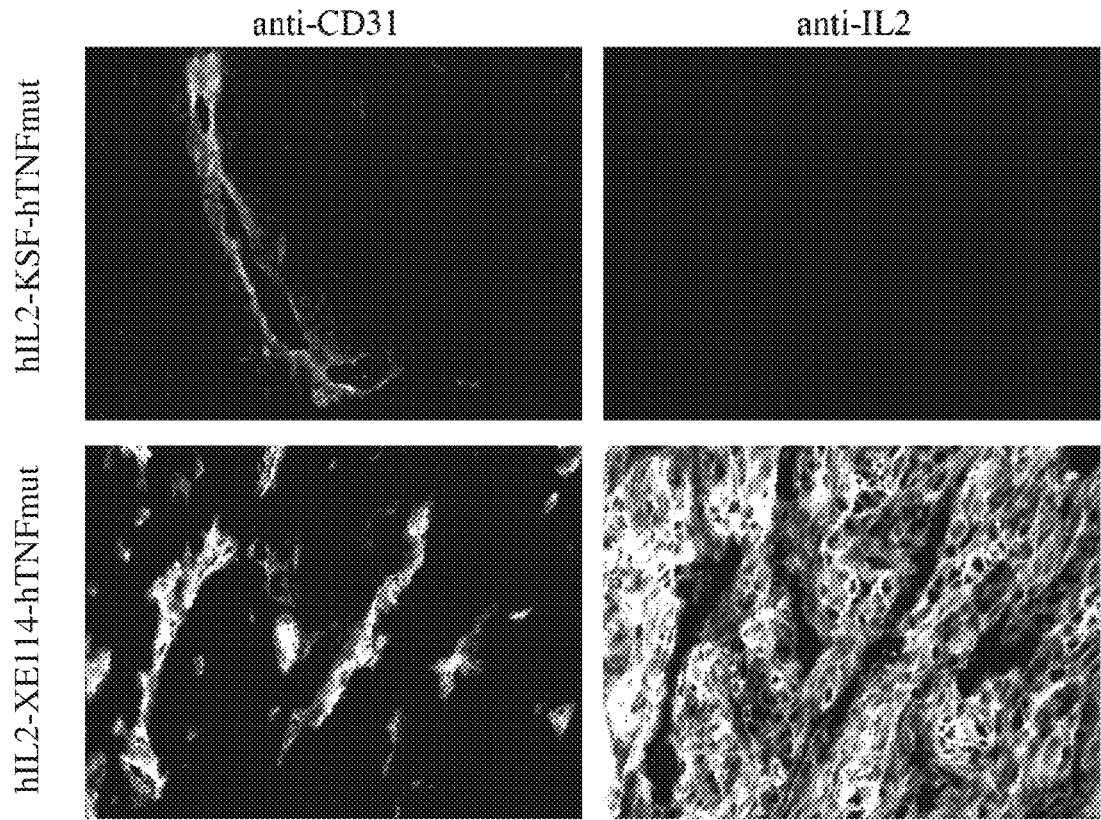

FIG. 14 shows the Microscopic fluorescence analysis of CAIX expression on SKRC52 tumor section stained with hIL2-XE114-hTNF$^{mut}$ (without the glycosylation motif) and IL2-KSF-TNF$^{mut}$ (negative control) conjugates and detected with a rat anti-IL2 antibody and followed by staining with anti-rat AlexaFluor488 antibody. The vasculature was stained with a goat anti-CD31 antibody and revealed with an anti-goat AlexaFluor594 antibody (20× magnification).

Figure 15:
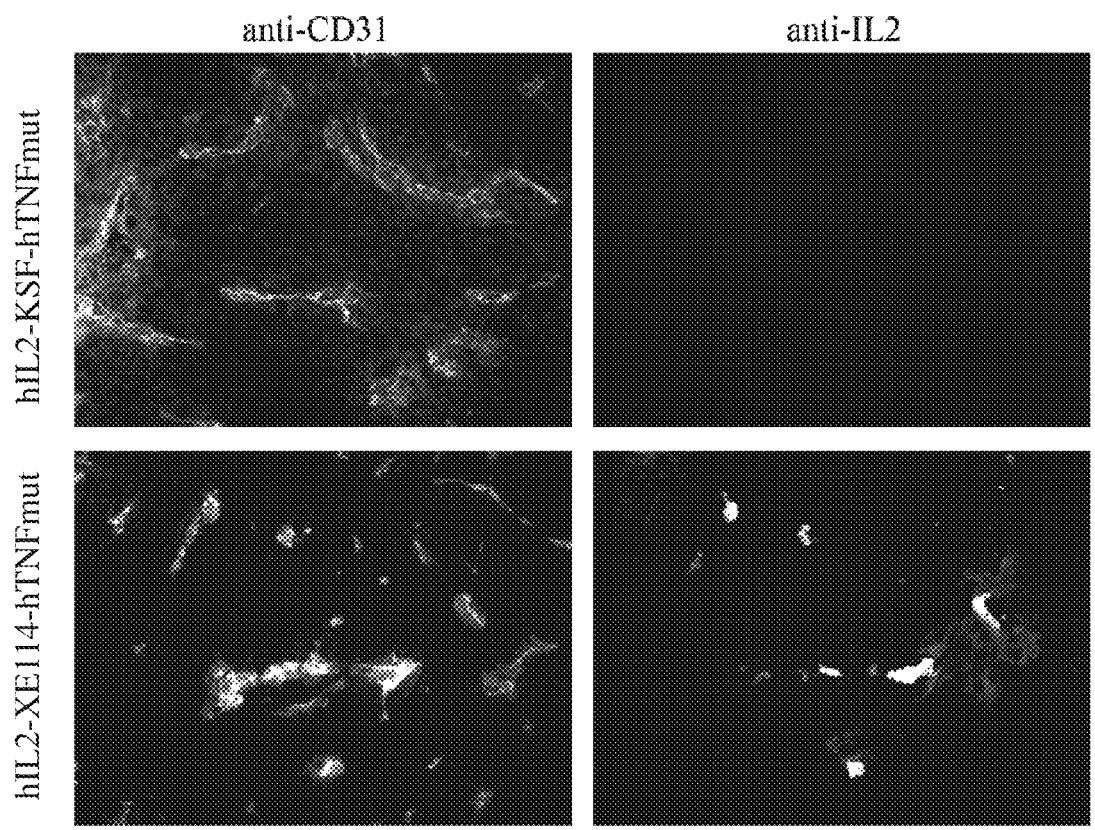

FIG. 15 shows the ex vivo immunofluorescence analysis of the targeting properties of hIL2-XE114-hTNFm" (without the glycosylation motif) and IL2-KSF-TNF$^{mut}$ (negative control) conjugates 24 hours after their injection in mice bearing SKRC52 lesions. Cryosections were stained with anti-human IL2 (Alexa Fluor 488) and anti-CD31 (Alexa Fluor 594) (20× magnification).

DETAILED DESCRIPTION

Carbonic Anhydrase IX

CAIX is a dimeric transmembrane protein expressed by tumour cells in response to hypoxia and is involved in maintaining the intracellular pH in the presence of an acidic extracellular environment. CAIX is expressed by many solid tumours and is associated with poor prognosis, as well as having been shown to correlate with metastasis. CAIX comprises an extracellular portion which is separated from a short intracellular tail by a single pass transmembrane domain.

The term "carbonic anhydrase IX" or "CAIX" (CA-IX), as used herein, may refer to human carbonic anhydrase IX and homologues thereof in non-human mammals, such as mouse. Preferably, the term CAIX, as used herein, refers to human CAIX and fragments thereof, such as the extracellular domain of CAIX. Human CAIX may have the sequence set forth in SEQ ID NO: 17. The extracellular domain of human CAIX may have the sequence set forth in SEQ ID NO: 16.

Cancer

This describes a malignant transformation of normal tissue involving unregulated cell growth. The term "cancer" as used herein may refer to lung cancer, colon cancer, breast cancer, cervical cancer, bladder cancer, rectal cancer, ovarian cancer, brain cancer, head and neck cancer, oral cavity cancer or kidney cancer. The kidney cancer may be renal cell carcinoma (RCC). The breast cancer may be basal like or triple negative breast cancer which has shown to have particularly high expression of CAIX (McDonald et al., 2012, Oncotarget, 3(1): 84-97). Triple negative breast cancer refers to breast cancer which does not express the genes for estrogen receptor, progesterone receptor or Her2/neu. The lung cancer may be squamous cell carcinoma, as it has been shown that there is a higher percentage of CAIX positive tumours among the squamous cell phenotype (McDonald et al., 2012, Oncotarget, 3(1): 84-97). Most preferably, the cancer is renal cell carcinoma (RCC). The cancer may express, e.g. may have been determined to express, CAIX.

A tumour, as referred to herein, may be a tumour which is a result of one of the cancers referred to above, most preferably renal cell carcinoma (RCC). The tumour may be a solid tumour. A solid tumour is a tumour which does not usually contain cysts or liquid areas. The term "tumour" may refer to a primary tumour and/or to a metastasis. As for the cancer, the tumour may express, e.g. may have been determined to express, CAIX.

Specific Binding Member

This describes one member of a pair of molecules that bind specifically to one another. The members of a specific binding pair may be naturally derived or wholly or partially synthetically produced. One member of the pair of molecules has an area on its surface, or a cavity, which binds to and is therefore complementary to a particular spatial and polar organization of the other member of the pair of molecules. Examples of types of binding pairs are antigen-antibody, biotin-avidin, hormone-hormone receptor, receptor-ligand, enzyme-substrate. The present invention is concerned with antigen-antibody type reactions.

A specific binding member normally comprises a molecule having an antigen-binding site. For example, a specific binding member may be an antibody molecule or a non-antibody protein that comprises an antigen-binding site. A specific binding member, as referred to herein, is preferably an antibody molecule.

An antigen binding site may be provided by means of arrangement of complementarity determining regions (CDRs) on non-antibody protein scaffolds such as fibronectin or cytochrome B etc. (Haan & Maggos, (2004), BioCentury, 12(5): A1-A6; Koide et al., (1998), Journal of Molecular Biology, 284: 1141-1151; Nygren et al., (1997), Current Opinion in Structural Biology, 7: 463-469), or by randomising or mutating amino acid residues of a loop within a protein scaffold to confer binding specificity for a desired target. Scaffolds for engineering novel binding sites in proteins have been reviewed in detail by Nygren et al. (1997) (Current Opinion in Structural Biology, 7: 463-469). Protein scaffolds for antibody mimics are disclosed in WO00/034784, in which the inventors describe proteins (antibody mimics) that include a fibronectin type III domain having at least one randomised loop. A suitable scaffold into which to graft one or more CDRs, e.g. a set of HCDRs, may be provided by any domain member of the immunoglobulin gene superfamily. The scaffold may be a human or non-human protein. An advantage of a non-antibody protein scaffold is that it may provide an antigen-binding site in a scaffold molecule that is smaller and/or easier to manufacture than at least some antibody molecules. Small size of a binding member may confer useful physiological properties such as an ability to enter cells, penetrate deep into tissues or reach targets within other structures, or to bind within protein cavities of the target antigen. Use of antigen binding sites in non-antibody protein scaffolds is reviewed in Wess, 2004, In: BioCentury, The Bernstein Report on BioBusiness, 12(42), A1-A7. Typical are proteins having a stable backbone and one or more variable loops, in which the amino acid sequence of the loop or loops is specifically or randomly mutated to create an antigen-binding site that binds the target antigen. Such proteins include the IgG-binding domains of protein A from *S. aureus*, transferrin, tetranectin, fibronectin (e.g. 10th fibronectin type III domain) and lipocalins. Other approaches include synthetic "Microbodies" (Selecore GmbH), which are based on cyclotides—small proteins having intra-molecular disulphide bonds.

In addition to antibody sequences and/or an antigen-binding site, a specific binding member for use in the present invention may comprise other amino acids, e.g. forming a peptide or polypeptide, such as a folded domain, or to impart to the molecule another functional characteristic in addition to ability to bind antigen. Binding members of the invention may carry a detectable label, or a molecule that exerts biocidal or cytotoxic activity (e.g. via a peptidyl bond or linker).

For example, a binding member may comprise a catalytic site (e.g. in an enzyme domain) as well as an antigen binding site, wherein the antigen binding site binds to the antigen and thus targets the catalytic site to the antigen. The catalytic site may inhibit biological function of the antigen, e.g. by cleavage.

Although, as noted, CDRs can be carried by non-antibody scaffolds, the structure for carrying a CDR or a set of CDRs will generally be an antibody heavy or light chain sequence or substantial portion thereof in which the CDR or set of CDRs is located at a location corresponding to the CDR or set of CDRs of naturally occurring VH and VL antibody variable domains encoded by rearranged immunoglobulin genes. The structures and locations of immunoglobulin variable domains may be determined by reference to Kabat et al. (1987) (Sequences of Proteins of Immunological Interest. $4^{th}$ Edition. US Department of Health and Human Services.), and updates thereof, now available on the Internet (at immuno.bme.nwu.edu or find "Kabat" using any search engine).

By CDR region or CDR, it is intended to indicate the hypervariable regions of the heavy and light chains of the immunoglobulin as defined, among others, by Kabat et al. (1987) Sequences of Proteins of Immunological Interest, $4^{th}$ Edition, US Department of Health and Human Services (Kabat et al., (1991a), Sequences of Proteins of Immunological Interest, $5^{th}$ Edition, US Department of Health and Human Services, Public Service, NIH, Washington, and later editions).

An antibody typically contains 3 heavy chain CDRs and 3 light chain CDRs. The term CDR or CDRs is used here in order to indicate, according to the case, one of these regions or several, or even the whole, of these regions which contain the majority of the amino acid residues responsible for the binding by affinity of the antibody for the antigen or the epitope which it recognizes.

Among the six short CDR sequences, the third CDR of the heavy chain (HCDR3) has a greater size variability (greater diversity essentially due to the mechanisms of arrangement of the genes which give rise to it). It can be as short as 2 amino acids although the longest size known is 26. Functionally, HCDR3 plays a role in part in the determination of the specificity of the antibody (Segal et al., (1974), PNAS, 71:4298-4302; Amit et al., (1986), Science, 233:747-753; Chothia et al., (1987), J. Mol. Biol., 196:901-917; Chothia et al., (1989), Nature, 342:877-883; Caton et al., (1990), J. Immunol., 144:1965-1968; Sharon et al., (1990a), PNAS, 87:4814-4817; Sharon et al., (1990b), J. Immunol., 144: 4863-4869; Kabat et al., (1991b), J. Immunol., 147:1709-1719).

Antibody Molecule

This describes an immunoglobulin whether natural or partly or wholly synthetically produced. The term also relates to any polypeptide or protein comprising an antibody antigen-binding site. It must be understood here that the invention does not relate to the antibodies in natural form, that is to say they are not in their natural environment but that they have been able to be isolated or obtained by purification from natural sources, or else obtained by genetic recombination, or by chemical synthesis, and that they can then contain unnatural amino acids as will be described later. Antibody fragments that comprise an antibody antigen-binding site include, but are not limited to, antibody molecules such as Fab, Fab', Fab'-SH, scFv, Fv, dAb, Fd; and diabodies.

It is possible to take monoclonal and other antibodies and use techniques of recombinant DNA technology to produce other antibodies or chimeric molecules that bind the target antigen. Such techniques may involve introducing DNA encoding the immunoglobulin variable region, or the CDRs, of an antibody to the constant regions, or constant regions plus framework regions, of a different immunoglobulin. See, for instance, EP-A-184187, GB 2188638A or EP-A-239400, and a large body of subsequent literature. A hybridoma or other cell producing an antibody may be subject to genetic mutation or other changes, which may or may not alter the binding specificity of antibodies produced.

As antibodies can be modified in a number of ways, the term "antibody molecule" should be construed as covering any binding member or substance having an antibody antigen-binding site with the required specificity and/or binding to antigen. Thus, this term covers antibody fragments and derivatives, including any polypeptide comprising an antibody antigen-binding site, whether natural or wholly or partially synthetic. Chimeric molecules comprising an antibody antigen-binding site, or equivalent, fused to another polypeptide (e.g. derived from another species or belonging to another antibody class or subclass) are therefore included. Cloning and expression of chimeric antibodies are described in EP-A-0120694 and EP-A-0125023, and a large body of subsequent literature.

Further techniques available in the art of antibody engineering have made it possible to isolate human and humanised antibodies. For example, human hybridomas can be made as described by Kontermann & Dubel (2001), S, Antibody Engineering, Springer-Verlag New York, LLC; ISBN: 3540413545. Phage display, another established technique for generating binding members has been described in detail in many publications such as WO92/01047 (discussed further below) and US patents U.S. Pat. Nos. 5,969,108, 5,565,332, 5,733,743, 5,858,657, 5,871,907, 5,872,215, 5,885,793, 5,962,255, 6,140,471, 6,172,197, 6,225,447, 6,291,650, 6,492,160, 6,521,404 and Kontermann & Dubel (2001), S, Antibody Engineering, Springer-Verlag New York, LLC; ISBN: 3540413545. Transgenic mice in which the mouse antibody genes are inactivated and functionally replaced with human antibody genes while leaving intact other components of the mouse immune system, can be used for isolating human antibodies (Mendez et al., (1997), Nature Genet, 15(2): 146-156).

Synthetic antibody molecules may be created by expression from genes generated by means of oligonucleotides synthesized and assembled within suitable expression vectors, for example as described by Knappik et al. (2000) J. Mol. Biol. 296, 57-86 or Krebs et al. (2001) Journal of Immunological Methods, 254 67-84.

It has been shown that fragments of a whole antibody can perform the function of binding antigens. Examples of binding fragments are (i) the Fab fragment consisting of VL, VH, CL and CH1 domains; (ii) the Fd fragment consisting of the VH and CH1 domains; (iii) the Fv fragment consisting of the VL and VH domains of a single antibody; (iv) the dAb fragment (Ward et al. (1989) Nature 341, 544-546; McCafferty et al., (1990) Nature, 348, 552-554; Holt et al. (2003) Trends in Biotechnology 21, 484-490), which consists of a VH or a VL domain; (v) isolated CDR regions; (vi) F(ab')2 fragments, a bivalent fragment comprising two linked Fab fragments (vii) single chain Fv molecules (scFv), wherein a VH domain and a VL domain are linked by a peptide linker which allows the two domains to associate to form an antigen binding site (Bird et al. (1988) Science, 242, 423-426; Huston et al. (1988) PNAS USA, 85, 5879-5883); (viii) bispecific single chain Fv dimers (PCT/US92/09965) and (ix) "diabodies", multivalent or multispecific fragments constructed by gene fusion (WO94/13804; Holliger et al. (1993a), Proc. Natl. Acad. Sci. USA 90 6444-6448). Fv, scFv or diabody molecules may be stabilized by the incorporation of disulphide bridges linking the VH and VL domains (Reiter et al. (1996), Nature Biotech, 14, 1239-1245). Minibodies comprising a scFv joined to a CH3 domain may also be made (Hu et al. (1996), Cancer Res., 56(13):3055-61). Other examples of binding fragments are Fab', which differs from Fab fragments by the addition of a few residues at the carboxyl terminus of the heavy chain CH1 domain, including one or more cysteines from the antibody hinge region, and Fab'-SH, which is a Fab' fragment in which the cysteine residue(s) of the constant domains bear a free thiol group.

Antibody fragments of the invention can be obtained starting from any of the antibody molecules described herein, e.g. antibody molecules comprising VH and/or VL domains or CDRs of any of antibodies described herein, by methods such as digestion by enzymes, such as pepsin or papain and/or by cleavage of the disulfide bridges by chemical reduction. In another manner, antibody fragments of the present invention may be obtained by techniques of genetic recombination likewise well known to the person skilled in the art or else by peptide synthesis by means of, for example, automatic peptide synthesizers such as those supplied by the company Applied Biosystems, etc., or by nucleic acid synthesis and expression.

Functional antibody fragments according to the present invention include any functional fragment whose half-life is increased by a chemical modification, especially by PEGylation, or by incorporation in a liposome.

A dAb (domain antibody) is a small monomeric antigen-binding fragment of an antibody, namely the variable region of an antibody heavy or light chain (Holt et al. (2003) Trends in Biotechnology 21, 484-490). VH dAbs occur naturally in camelids (e.g. camel, llama) and may be produced by immunizing a camelid with a target antigen, isolating antigen-specific B cells and directly cloning dAb genes from individual B cells. dAbs are also producible in cell culture. Their small size, good solubility and temperature stability makes them particularly physiologically useful and suitable for selection and affinity maturation. A binding member of the present invention may be a dAb comprising a VH or VL domain substantially as set out herein, or a VH or VL domain comprising a set of CDRs substantially as set out herein.

As used herein, the phrase "substantially as set out" refers to the characteristic(s) of the relevant CDRs of the VH or VL domain of binding members described herein will be either identical or highly similar to the specified regions of which the sequence is set out herein. As described herein, the phrase "highly similar" with respect to specified region(s) of one or more variable domains, it is contemplated that from 1 to about 5, e.g. from 1 to 4, including 1 to 3, or 1 or 2, or 3 or 4, amino acid substitutions, deletions or insertions may be made in the CDRs and/or VH or VL domain.

Bispecific or bifunctional antibodies form a second generation of monoclonal antibodies in which two different variable regions are combined in the same molecule (Holliger and Bohlen 1999 Cancer and metastasis rev. 18: 411-419). Their use has been demonstrated both in the diagnostic field and in the therapy field from their capacity to recruit new effector functions or to target several molecules on the surface of tumor cells. Where bispecific antibodies are to be used, these may be conventional bispecific antibodies, which can be manufactured in a variety of ways (Holliger et al. (1993b), Current Opinion Biotechnol 4, 446-449), e.g. prepared chemically or from hybrid hybridomas, or may be any of the bispecific antibody fragments mentioned above. These antibodies can be obtained by chemical methods (Glennie et al., (1987) J. Immunol. 139, 2367-2375; Repp et al., (1995) J. Hemat. 377-382) or somatic methods (Staerz U. D. and Bevan M. J. (1986) PNAS 83; Suresh et al. (1986) Method. Enzymol. 121: 210-228) but likewise by genetic engineering techniques which allow the heterodimerization to be forced and thus facilitate the process of purification of the antibody sought (Merchand et al., 1998 Nature Biotech. 16:677-681). Examples of bispecific antibodies include those of the BiTE' technology in which the binding domains of two antibodies with different specificity can be used and directly linked via short flexible peptides. This combines two antibodies on a short single polypeptide chain. Diabodies and scFv can be constructed without an Fc region, using only variable domains, potentially reducing the effects of anti-idiotypic reaction.

Bispecific antibodies can be constructed as entire IgG, as bispecific Fab'2, as Fab'PEG, as diabodies or else as bispecific scFv. Further, two bispecific antibodies can be linked using routine methods known in the art to form tetravalent antibodies.

Bispecific diabodies, as opposed to bispecific whole antibodies, may also be particularly useful because they can be readily constructed and expressed in E. coli. Diabodies (and many other polypeptides such as antibody fragments) of appropriate binding specificities can be readily selected using phage display (WO94/13804) from libraries. If one arm of the diabody is to be kept constant, for instance, with a specificity directed against a target antigen, then a library can be made where the other arm is varied and an antibody of appropriate specificity selected. Bispecific whole antibodies may be made by alternative engineering methods as described in Ridgeway et al. (1996), Protein Eng., 9, 616-621.

Various methods are available in the art for obtaining antibodies against a target antigen. The antibodies may be monoclonal antibodies, especially of human, murine, chimeric or humanized origin, which can be obtained according to the standard methods well known to the person skilled in the art.

In general, for the preparation of monoclonal antibodies or their functional fragments, especially of murine origin, it is possible to refer to techniques which are described in particular in the manual "Antibodies" (Harlow and Lane, Antibodies: A Laboratory Manual, Cold Spring Harbor Laboratory, Cold Spring Harbor N.Y., pp. 726, 1988) or to the technique of preparation from hybridomas described by Kohler and Milstein, 1975, Nature, 256:495-497.

Monoclonal antibodies can be obtained, for example, from an animal cell immunized against CAIX, or one of its fragments containing the epitope recognized by said monoclonal antibodies. Suitable fragments include the CAIX extracellular domain, which may comprise or consist of amino acids 120-397 of CAIX, or a peptide fragment of CAIX. CAIX, or one of its fragments, can be produced according to the usual working methods, by genetic recombination starting with a nucleic acid sequence contained in the cDNA sequence coding for CAIX, or fragment thereof, or by peptide synthesis starting from a sequence of amino acids comprised in the peptide sequence of CAIX and/or fragment thereof.

Monoclonal antibodies can, for example, be purified on an affinity column on which CAIX, the CAIX extracellular domain of CAIX (which may comprise or consist of amino acids 120-397 of CAIX), or another fragment of CAIX containing the epitope recognized by said monoclonal antibodies, has previously been immobilized. Monoclonal antibodies can be purified by chromatography on protein A and/or G, followed or not followed by ion-exchange chromatography aimed at eliminating the residual protein contaminants as well as the DNA and the LPS, in itself, followed or not followed by exclusion chromatography on Sepharose gel in order to eliminate the potential aggregates due to the presence of dimers or of other multimers. The whole of these techniques may be used simultaneously or successively.

Antigen-Binding Site

This describes the part of a molecule that binds to and is complementary to all or part of the target antigen. In an antibody molecule it is referred to as the antibody antigen-binding site, and comprises the part of the antibody that binds to and is complementary to all or part of the target antigen. Where an antigen is large, an antibody may only bind to a particular part of the antigen, which part is termed an epitope. An antibody antigen-binding site may be provided by one or more antibody variable domains. An antibody antigen-binding site may comprise an antibody light chain variable region (VL) and an antibody heavy chain variable region (VH).

Isolated

This refers to the state in which specific binding members, e.g. antibody molecules, of the invention or nucleic acid encoding such specific binding members, will generally be in accordance with the present invention. Thus, specific binding members, VH and/or VL domains of the present invention may be provided isolated and/or purified, e.g. from their natural environment, in substantially pure or homogeneous form, or, in the case of nucleic acid, free or substantially free of nucleic acid or genes of origin other than the sequence encoding a polypeptide with the required function. Isolated members and isolated nucleic acid will be free or substantially free of material with which they are naturally associated such as other polypeptides or nucleic acids with which they are found in their natural environment, or the environment in which they are prepared (e.g. cell culture) when such preparation is by recombinant DNA technology practised in vitro or in vivo. Specific binding members and nucleic acid may be formulated with diluents or adjuvants and still for practical purposes be isolated—for example the members will normally be mixed with gelatin or other carriers if used to coat microtitre plates for use in immunoassays, or will be mixed with pharmaceutically acceptable carriers or diluents when used in diagnosis or therapy. Specific binding members may be glycosylated, either naturally or by systems of heterologous eukaryotic cells (e.g. CHO or NS0 (ECACC 85110503) cells, or they may be (for example if produced by expression in a prokaryotic cell) unglycosylated.

Heterogeneous preparations comprising antibody molecules may also be used in the invention. For example, such preparations may be mixtures of antibodies with full-length heavy chains and heavy chains lacking the C-terminal lysine, with various degrees of glycosylation and/or with derivatized amino acids, such as cyclization of an N-terminal glutamic acid to form a pyroglutamic acid residue.

One or more specific binding members for CAIX may be obtained by bringing into contact a library of specific binding members according to the invention and the antigen or a fragment thereof, e.g. the full-length CAIX antigen, a fragment of CAIX comprising or consisting of the CAIX extracellular domain (which may comprise of consist of amino acids 120-397 of CAIX), or another fragment (e.g. a peptide fragment) of CAIX, and selecting one or more specific binding members of the library able to bind the antigen.

An antibody library may be screened using Iterative Colony Filter Screening (ICFS) according to Giovannoni et al., Nucleic Acids Research (2001), 29:5 e27. In ICFS, bacteria containing the DNA encoding several binding specificities are grown in a liquid medium and, once the stage of exponential growth has been reached, some billions of them are distributed onto a growth support consisting of a suitably pre-treated membrane filter which is incubated until completely confluent bacterial colonies appear. A second trap substrate consists of another membrane filter, pre-humidified and covered with the desired antigen.

The trap membrane filter is then placed onto a plate containing a suitable culture medium and covered with the growth filter with the surface covered with bacterial colonies pointing upwards. The sandwich thus obtained is incubated at room temperature for about 16 h. It is thus possible to obtain the expression of the genes encoding antibody fragments scFv having a spreading action, so that those fragments binding specifically with the antigen which is present on the trap membrane are trapped. The trap membrane is then treated to point out bound antibody fragments scFv with colorimetric techniques commonly used to this purpose.

The position of the coloured spots on the trap filter allows one to go back to the corresponding bacterial colonies which are present on the growth membrane and produced the antibody fragments trapped. Such colonies are gathered and grown and the bacteria-a few millions of them are distributed onto a new culture membrane repeating the procedures described above. Analogous cycles are then carried out until the positive signals on the trap membrane correspond to single positive colonies, each of which represents a potential source of monoclonal antibody fragments directed against the antigen used in the selection. ICFS is described in e.g. WO0246455.

A library may also be displayed on particles or molecular complexes, e.g. replicable genetic packages such bacteriophage (e.g. T7) particles, or other in vitro display systems, each particle or molecular complex containing nucleic acid encoding the antibody VH variable domain displayed on it, and optionally also a displayed VL domain if present. Phage display is described in WO92/01047 and e.g. US patents U.S. Pat. Nos. 5,969,108, 5,565,332, 5,733,743, 5,858,657, 5,871,907, U.S. Pat. Nos. 5,872,215, 5,885,793, 5,962,255, 6,140,471, 6,172,197, 6,225,447, 6,291,650, 6,492,160 and 6,521,404.

Following selection of binding members able to bind the antigen and displayed on bacteriophage or other library particles or molecular complexes, nucleic acid may be taken from a bacteriophage or other particle or molecular complex displaying a said selected binding member. Such nucleic acid may be used in subsequent production of a binding member or an antibody VH or VL variable domain by expression from nucleic acid with the sequence of nucleic acid taken from a bacteriophage or other particle or molecular complex displaying a said selected binding member.

An antibody VH variable domain with the amino acid sequence of an antibody VH variable domain of a said selected binding member may be provided in isolated form, as may a binding member comprising such a VH domain.

Ability to bind CAIX may be further tested, e.g. ability to compete with the XE114 anti-CAIX antibody for binding to CAIX or a fragment thereof, such as a fragment comprising or consisting of the CAIX extracellular domain (which may comprise of consist of amino acids 120-397 of CAIX), or another fragment (e.g. a peptide fragment) of CAIX.

A specific binding member of the invention may bind CAIX, e.g. the extracellular domain of CAIX (which may comprise of consist of amino acids 120-397 of CAIX), specifically. A specific binding member of the present invention may bind CAIX, with the same affinity as the XE114 anti-CAIX antibody, e.g. in scFv format, or with an affinity that is higher. A specific binding member of the invention may bind CAIX, with a $K_D$ of 25 nM or an affinity that is higher. Preferably, a specific binding member of the invention binds CAIX, with a $K_D$ of 20 nM or an affinity that is higher. More preferably, a specific binding member of the invention binds CAIX, with a $K_D$ of 15 nM, 10 nM, 5 nM, or 4 nM, or an affinity that is higher, preferably with a $K_D$ of 3 nM or an affinity that is higher. The affinity of a specific binding member for CAIX may be measured using surface plasmon resonance (SPR), such as Biacore using the experimental set up described in the present examples, wherein the concentration of the specific binding member may e.g. be 660 nM.

A specific binding member of the present invention may have the same dissociation rate constant ($k_{off}$) when bound to CAIX, as the XE114 anti-CAIX antibody, e.g. in scFv format, or a $k_{off}$ that is slower. A slower $k_{off}$ is indicated by a lower $k_{off}$ value, and means that the specific binding member dissociates more slowly from its congnate antigen, here CAIX. A specific binding member of the invention may bind CAIX with a $k_{off}$ of $5 \times 10^{-4}$ s$^{-1}$ or a $k_{off}$ that is slower.

The present inventors have shown that the dissociation constant ($k_{off}$) of the anti-CAIX antibody without the glycosylation motif in scFv format is $3.05 \times 10^{-4}$ s$^{-1}$. Thus, in a preferred embodiment the $k_{off}$ of the anti-CAIX antibody in scFv format may be $4 \times 10^{-4}$ s$^{-1}$ or $3.5 \times 10^{-4}$ s$^{-1}$ or a $k_{off}$ that is slower. For example, the $k_{off}$ of the anti-CAIX antibody in scFv format may be about $3 \times 10^{-4}$ s$^{-1}$.

Cazzamalli et al. (J. Am. Chem. Soc. (2018), 140 (5), 1617-1621) report that the $k_{off}$ of the anti-CAIX antibody without the glycosylation motif in IgG1 format is $2.2 \times 10^{-4}$ s$^{-1}$. Thus, in a preferred embodiment the $k_{off}$ of the anti-CAIX antibody in IgG1 format may be $4 \times 10^{-5}$ s$^{-1}$, $3 \times 10^{-5}$ s$^{-1}$, or $2.5 \times 10^{-4}$ s$^{-1}$ or a $k_{off}$ that is slower. For example, the $k_{off}$ of the anti-CAIX antibody in IgG1 format may be about $2.2 \times 10^{-4}$ s$^{-1}$.

The low $k_{off}$ values of the specific binding members of the invention in scFv and IgG1 format are advantageous as they mean that these specific binding members dissociate more slowly from CAIX, i.e. remain bound to CAIX for longer than specific binding members with higher $k_{off}$ values. Slow dissociation is expected to be advantageous in detection of CAIX-expressing cancers, such as in methods of diagnosis or prognosis of cancer, as well as in methods comprising the delivery of therapeutic agents to sites of cancer in a patient, where conjugates comprising a specific binding member of the invention and a cytotoxic molecule, for example, are expected to remain bound to CAIX expressed on the tumour cells for longer and thus have a longer time window in which to exert their therapeutic effect.

The affinity or $k_{off}$ of a specific binding member for CAIX may be measured with the specific binding member in scFv format or with any other monomeric antibody fragment, such as Fab. Alternatively, it may be also measured with the specific binding member in IgG format or with any other dimeric antibody format, such as scFv-Fc. Methods for measuring $k_{off}$ are known in the art and include SPR, such as Biacore analysis.

A specific binding member of the present invention may bind to the same epitope, or substantially the same epitope, on CAIX as anti-CAIX antibody XE114. Methods for determining whether two specific binding members bind the same, or substantially the same, epitope are known in the art and include X-ray co-crystallography.

A specific binding member of the invention may not show any significant binding to molecules other than CAIX. In particular, the specific binding member may not show any significant binding to molecules other than the CAIX extracellular domain. The specific binding member may not show any significant binding to carbonic anhydrases other than CAIX. In particular, the specific binding member may not show any significant binding carbonic anhydrase XII (CAXII), which is also upregulated under hypoxic conditions.

Variants of antibody molecules disclosed herein may be produced and used in the present invention. The techniques required to make substitutions, deletions or insertions within amino acid sequences of CDRs, antibody VH or VL domains, in particular the framework regions of the VH and VL domains, and binding members generally are available in the art. Variant sequences may be made, with substitutions, deletions or insertions that may or may not be predicted to have a minimal or beneficial effect on activity, and tested for ability to CAIX, and/or for any other desired property.

Variable domain amino acid sequence variants of any of the VH and VL domains whose sequences are specifically disclosed herein may be employed in accordance with the present invention, as discussed. Particular variants may include one or more amino acid sequence alterations (addition, deletion, substitution and/or insertion of an amino acid residue), may be less than about 20 alterations, less than about 15 alterations, less than about 10 alterations or less than about 5 alterations, may be 5, 4, 3, 2 or 1. Alterations may be made in one or more framework regions and/or one or more CDRs. The alterations normally do not result in loss of function, so a specific binding member comprising a thus-altered amino acid sequence may retain an ability to bind CAIX. For example, it may retain the same quantitative binding as a specific binding member in which the alteration is not made, e.g. as measured in an assay described herein. The specific binding member comprising a thus-altered amino acid sequence may have an improved ability to bind CAIX. For example, a specific binding member that binds CAIX, as referred to herein, may comprise the VH domain shown in SEQ ID NO: 7 and the VL domain shown in SEQ ID NO: 8 with 10 or fewer, for example, 5, 4, 3, 2 or 1 amino acid alterations, e.g. substitutions, within the framework region of the VH and/or VL domain. Such a specific binding member may bind CAIX with the same or substantially the same, affinity as a specific binding member comprising the VH domain shown in SEQ ID NO: 7 and the VL domain shown in SEQ ID NO: 8 or may bind CAIX with a higher affinity than a specific binding member comprising the VH domain shown in SEQ ID NO: 7 and the VL domain shown in SEQ ID NO: 8. Preferably, a specific binding member that binds CAIX, as referred to herein, comprises the VH domain shown in SEQ ID NO: 7 and the VL domain shown in SEQ ID NO: 20 with 10 or fewer, for example, 5, 4, 3, 2 or 1 amino acid alterations, e.g. substitutions, within the framework region of the VH and/or VL domain. Such a specific binding member may bind CAIX with the same or substantially the same, affinity as a specific binding member comprising the VH domain shown in SEQ ID NO: 7 and the VL domain shown in SEQ ID NO: 20 or may bind CAIX with a higher affinity than a specific binding member comprising the VH domain shown in SEQ ID NO: 7 and the VL domain shown in SEQ ID NO: 20.

Novel VH or VL regions carrying CDR-derived sequences of the invention may be generated using random mutagenesis of one or more selected VH and/or VL genes to generate mutations within the entire variable domain. In some embodiments one or two amino acid substitutions, deletions or insertions are made within an entire variable domain or set of CDRs. Another method that may be used is to direct mutagenesis to CDR regions of VH or VL genes.

As noted above, a CDR amino acid sequence substantially as set out herein may be carried as a CDR in a human antibody variable domain or a substantial portion thereof. The HCDR3 sequences substantially as set out herein represent embodiments of the present invention and for example each of these may be carried as a HCDR3 in a human heavy chain variable domain or a substantial portion thereof.

Variable domains employed in the invention may be obtained or derived from any germ-line or rearranged human variable domain, or may be a synthetic variable domain based on consensus or actual sequences of known human variable domains. A variable domain can be derived from a non-human antibody. A CDR sequence of the invention (e.g. CDR3) may be introduced into a repertoire of variable domains lacking a CDR (e.g. CDR3), using recombinant DNA technology. For example, Marks et al. (1992) describe methods of producing repertoires of antibody variable domains in which consensus primers directed at or adjacent to the 5' end of the variable domain area are used in conjunction with consensus primers to the third framework region of human VH genes to provide a repertoire of VH variable domains lacking a CDR3. Marks et al. further describe how this repertoire may be combined with a CDR3 of a particular antibody. Using analogous techniques, the CDR3-derived sequences of the present invention may be shuffled with repertoires of VH or VL domains lacking a CDR3, and the shuffled complete VH or VL domains combined with a cognate VL or VH domain to provide binding members for use in the invention. The repertoire may then be displayed in a suitable host system such as the phage display system of WO92/01047, or any of a subsequent large body of literature, including Kay, Winter & McCafferty (1996), so that suitable binding members may be selected. A repertoire may consist of from anything from $10^4$ individual members upwards, for example at least $10^5$, at least $10^6$, at least $10^7$, at least $10^8$, at least $10^9$ or at least $10^{10}$ members. A suitable repertoire may be as described by Silacci et al., (2005) Proteomics, 5: 2340-2350 or as in WO10/028791.

Similarly, one or more, or all three CDRs may be grafted into a repertoire of VH or VL domains that are then screened for a binding member or binding members for CAIX, in particular the extracellular domain of CAIX (which may comprise of consist of amino acids 120-397 of CAIX).

One or more of the HCDR1, HCDR2 and HCDR3 of anti-CAIX antibody XE114 or the set of HCDRs of anti-CAIX antibody XE114 may be employed, and/or one or more of the LCDR1, LCDR2 and LCDR3 of the anti-CAIX antibody XE114 or the set of LCDRs of the anti-CAIX antibody XE114 may be employed.

Similarly, other VH and VL domains, sets of CDRs and sets of HCDRs and/or sets of LCDRs disclosed herein may be employed.

A substantial portion of an immunoglobulin variable domain may comprise at least the three CDR regions, together with their intervening framework regions. The portion may also include at least about 50% of either or both of the first and fourth framework regions, the 50% being the C-terminal 50% of the first framework region and the N-terminal 50% of the fourth framework region. Additional residues at the N-terminal or C-terminal end of the substantial part of the variable domain may be those not normally associated with naturally occurring variable domain regions. For example, construction of specific binding members of the present invention made by recombinant DNA techniques may result in the introduction of N- or C-terminal residues encoded by linkers introduced to facilitate cloning or other manipulation steps. Other manipulation steps include the introduction of linkers to join variable domains disclosed elsewhere herein to further protein sequences including antibody constant regions, other variable domains (for example in the production of diabodies) or detectable/functional labels as discussed in more detail elsewhere herein.

Although specific binding members may comprise a pair of VH and VL domains, single binding domains based on either VH or VL domain sequences may also be used in the invention. It is known that single immunoglobulin domains, especially VH domains, are capable of binding target antigens in a specific manner. For example, see the discussion of dAbs above.

In the case of either of the single binding domains, these domains may be used to screen for complementary domains capable of forming a two-domain binding member able to CAIX. This may be achieved by phage display screening methods using the so-called hierarchical dual combinatorial approach as disclosed in WO92/01047, in which an individual colony containing either an H or L chain clone is used to infect a complete library of clones encoding the other chain (L or H) and the resulting two-chain binding member is selected in accordance with phage display techniques such as those described in that reference. This technique is also disclosed in Marks 1992.

Specific binding members for use in the present invention may further comprise antibody constant regions or parts thereof, e.g. human antibody constant regions or parts thereof. For example, a VL domain may be attached at its C-terminal end to antibody light chain constant domains including human Cκ or Cλ chains, e.g. Cλ.

Similarly, a specific binding member based on a VH domain may be attached at its C-terminal end to all or part (e.g. a CH1 domain) of an immunoglobulin heavy chain derived from any antibody isotype, e.g. IgG, IgA, IgE and IgM and any of the isotype sub-classes, particularly IgG1 and IgG4. Any synthetic or other constant region variant that has these properties and stabilizes variable regions is also useful in embodiments of the present invention.

Specific binding members of the invention may be labelled with a detectable or functional label. A label can be any molecule that produces or can be induced to produce a signal, including but not limited to fluorescers, radiolabels, enzymes, chemiluminescers or photosensitizers. Thus, binding may be detected and/or measured by detecting fluorescence or luminescence, radioactivity, enzyme activity or light absorbance. Detectable labels may be attached to antibodies of the invention using conventional chemistry known in the art.

There are numerous methods by which the label can produce a signal detectable by external means, for example, by visual examination, electromagnetic radiation, heat, and chemical reagents. The label can also be bound to another specific binding member that binds the antibody for use in the invention, or to a support.

Labelled specific binding members, e.g. whole antibodies or antibody fragments (e.g. scFv) labelled with a detectable label, may be used diagnostically in vivo, ex vivo or in vitro, and/or therapeutically.

For example, radiolabelled binding members (e.g. binding members conjugated to a radioisotope) may be used in radiodiagnosis and radiotherapy. Radioisotopes which may be conjugated to a binding member of the invention include isotopes such as $^{94m}$Tc, $^{99m}$Tc, $^{186}$Re, $^{188}$Re, $^{203}$P, $^{67}$Ga, $^{68}$Ga, $^{47}$Sc, $^{111}$In, $^{97}$Ru, $^{62}$Cu, $^{64}$Cu, $^{86}$Y, $^{88}$Y, $^{90}$Y, $^{121}$Sn, $^{161}$Tb, $^{153}$Sm, $^{166}$Ho, $^{105}$Rh, $^{177}$Lu, $^{123}$I, $^{124}$I, $^{125}$I, $^{131}$I, $^{18}$F, $^{211}$At and $^{225}$Ac Preferably, positron emitters, such as $^{18}$F and $^{124}$I, or gamma emitters, such as $^{99m}$Tc, $^{111}$In and $^{123}$I, are used for diagnostic applications (e.g. for PET), while beta-emitters, such as $^{131}$I, $^{90}$Y and $^{177}$Lu, are preferably used for therapeutic applications. Alpha-emitters, such as $^{211}$At and $^{225}$Ac may also be used for therapy. In one example, the specific binding member may be conjugated to $^{177}$Lu or $^{90}$Y.

For example, a specific binding member of the invention labelled with a detectable label may be used to image, detect, diagnose or monitor cancer in a human or animal. A specific binding member of the present invention may be used for the manufacture of a diagnostic product for use in imaging, detecting or diagnosing cancer.

Further aspects of the present invention employ a conjugate, e.g. a fusion, between a specific binding member of the invention and a molecule that exerts a biocidal or cytotoxic effect on target cells, e.g. cancer cells expressing CAIX. Such conjugates may be used therapeutically for the treatment of cancer as referred to herein.

As discussed further below, the specific binding member of the invention is preferably an antibody molecule or comprises an antibody antigen-binding site. Conveniently, the specific binding member may be a single-chain polypeptide, such as a single-chain antibody. This allows for convenient production of a fusion protein comprising single-chain antibody and, for example, a biocidal or cytotoxic molecule. An antibody antigen-binding site may be provided by means of association of an antibody VH domain and an antibody VL domain in separate polypeptides, e.g. in a complete antibody or in an antibody fragment such as Fab or diabody. Where the specific binding member is a two-chain or multi-chain molecule (e.g. Fab or whole antibody, respectively), a biocidal or cytotoxic molecule may be conjugated as a fusion polypeptide with one or more polypeptide chains in the specific binding member.

The specific binding member may be conjugated with the biocidal or cytotoxic molecule means of a peptide bond, i.e. within a fusion polypeptide comprising said molecule and the specific binding member or a polypeptide chain component thereof (see e.g. Trachsel et al.). Other means for conjugation include chemical conjugation, especially cross-linking using a bifunctional reagent (e.g. employing DOUBLE-REAGENTS™ Cross-linking Reagents Selection Guide, Pierce).

The specific binding member of the invention may be conjugated to IL2 and TNF, such as TNFα, preferably a mutant of TNF. The specific binding member is preferably an scFv or a diabody, most preferably an scFv, as described herein.

IL2 is Preferably Human IL2.

The IL2 may comprise or consist of the IL2 sequence shown in SEQ ID NO: 24. Typically, IL2 has at least 70%, more preferably one of at least 75%, 80%, 85%, 90%, 95%, 96%, 97%, 98%, 99% or 100%, sequence identity to the IL2 sequence shown in SEQ ID NO: 24. IL2 in conjugates of the invention retains a biological activity of human IL2, e.g. the ability to inhibit cell proliferation.

TNF is preferably human TNF. Where the tumour necrosis factor is TNFα, the TNFα is preferably human TNFα.

The TNF mutant is a mutant of TNF which retains biological function of human TNF, e.g. the ability to inhibit cell proliferation but has a reduced activity.

The TNF mutant may comprise one or more mutations which reduce activity relative to the wild-type TNF which lacks the one or more mutations i.e. the TNF mutant is less potent than wild-type TNF. For example, the TNF mutant may comprise a mutation at the position corresponding to position 32 in TNF sequence shown in SEQ ID NO: 24. In some embodiments, the R at said position may be substituted for a different amino acid, preferably an amino acid other than G, for example a non-polar amino acid, preferably A, F, or V, most preferably A.

Human TNFα consists of a 35 amino acid cytoplasmic domain, a 20 amino acid transmembrane domain and a 177 amino acid extracellular domain. The 177 amino acid extracellular domain is cleaved to produce a 157 amino acid soluble form, which is biologically active, and which forms a non-covalently linked trimer in solution. In the context of the conjugates of the present invention, the human TNFα is a mutant of TNFα which is preferably the soluble form of the extracellular domain of human TNFα, or the extracellular domain of human TNFα. Typically, the mutant TNFα has at least 70%, more preferably one of at least 75%, at least 80%, at least 85%, at least 90%, at least 95%, at least 96%, at least 97%, at least 98%, at least 99% or 100%, sequence identity to the amino acid sequence shown in in SEQ ID NO: 24 with one or more mutations which reduce activity, for example a mutation at the position corresponding to position 32 in the TNF sequence shown in SEQ ID NO: 24.

Preferably, the specific binding member is connected to the IL2 and the TNF mutant, preferably TNFα mutant, through linkers, for example peptide linkers. Alternatively, the specific binding member and IL2 and/or a mutant of tumour necrosis factor, may be connected directly, e.g. through a chemical bond. Where the specific binding member is linked to IL2 and a mutant of tumour necrosis factor by means of one or more peptide linkers, the conjugate may be a fusion protein. By "fusion protein" is meant a polypeptide that is a translation product resulting from the fusion of two or more genes or nucleic acid coding sequences into one open reading frame (ORF).

The chemical bond may be, for example, a covalent or ionic bond. Examples of covalent bonds include peptide bonds (amide bonds) and disulphide bonds. The antibody molecule and IL2 and/or TNF mutant, preferably TNFα mutant, may be covalently linked, for example by peptide bonds (amide bonds). Thus, the specific binding member, in particular a scFv portion of an antibody molecule, and IL2 and/or the TNF mutant, preferably TNFα mutant, may be produced as a fusion protein.

Where the specific binding member is a two-chain or multi-chain molecule (e.g. a diabody), IL2 and/or the TNF mutant may be conjugated as a fusion protein with one or more polypeptide chains in the specific binding member.

The peptide linker connecting the antibody molecule and IL2 and/or the TNF mutant, may be a flexible peptide linker. Suitable examples of peptide linker sequences are known in the art. The linker may be 10-20 amino acids, preferably 10-15 amino acids in length. Most preferably, the linker is 11-15 amino acids in length. The linker may have the sequence shown in SEQ ID NO: 24.

Where the antibody molecule is, or comprises, an scFv, the IL2 may be linked to the N-terminus of the VH domain of the scFv via a peptide linker and the mutant of TNF may be linked to the C-terminus of the VL domain of the scFv via a peptide linker. Alternatively, where the antibody molecule is, or comprises, an scFv, the mutant of TNF may be linked to the N-terminus of the VH domain of the scFv via a peptide linker and the IL2 may be linked to the C-terminus of the VL domain of the scFv via a peptide linker. As a further alternative, the IL2 and TNF mutant, preferably TNFα mutant, may therefore be linked to the C-terminus of the VL domain of the antibody, e.g. in scFv format, via a peptide linker. As a yet further alternative the IL2 and TNF mutant, preferably TNFα mutant, may be linked to the N-terminus of the VH domain of the antibody, e.g. in scFv format, via a peptide linker. In the latter two conjugates, the IL2 and TNF may be in any order and/or may optionally be linked to one another via a peptide linker. Suitable peptide linkers are described herein.

The conjugates of the invention may comprise or consist of the sequence shown in SEQ ID NO: 24 or may be a variant thereof. A variant may have at least 70%, more preferably at least 75%, at least 80%, at least 85%, at least 90%, at least 95%, at least 96%, at least 97%, at least 98%, or at least 99% sequence identity to the reference sequence e.g. the amino acid sequence shown in SEQ ID NO: 24.

Without being limited by any theoretical explanation, a conjugate described herein comprising a TNF mutant may form a homotrimer in solution. Such a trimeric conjugate would comprise three molecules of active IL2 to one molecule of active TNF with reduced activity (in trimeric structure). This may be advantageous as IL2-based immunocytokines are typically used in the clinic at higher doses compared to TNFα-based immunocytokines. For example, the recommended dose of L19-IL2 was found to be 4 mg in patients with cancer [Johannsen et al. (2010) *Eur. J. Cancer*], while the recommended dose of L19-TNFα is in the 1-1.5 mg dose range [Spitaleri et al. (2012) *J. Clin. Oncol. Cancer Res.*]. Furthermore, higher doses of the conjugates described herein may be used as the mutant of TNF has a reduced activity, compared to a conjugate comprising a wild type TNF and IL2. Thus, the conjugates described herein may have advantageous properties with respect to administration regimens.

Also provided is an isolated nucleic acid encoding a specific binding member, or conjugate, of the present invention. Nucleic acid may include DNA and/or RNA. A nucleic acid may code for a CDR or set of CDRs or VH domain or VL domain or antibody antigen-binding site or antibody molecule, e.g. scFv or IgG, e.g. IgG1, as defined above. The nucleotide sequences may encode the VH and/or VL domains disclosed herein.

Further described herein are constructs in the form of plasmids, vectors, transcription or expression cassettes which comprise at least one polynucleotide as described above.

A recombinant host cell that comprises one or more constructs as above are also provided. A nucleic acid encoding any CDR or set of CDRs or VH domain or VL domain or antibody antigen-binding site or antibody molecule, e.g. scFv or IgG1 or IgG4 as provided, is described, as is a method of production of the encoded product, which method comprises expression from encoding nucleic acid. Expression may conveniently be achieved by culturing under appropriate conditions recombinant host cells containing the nucleic acid. Following production by expression a VH or VL domain, or specific binding member may be isolated and/or purified using any suitable technique, then used as appropriate.

A nucleic acid may comprise DNA or RNA and may be wholly or partially synthetic. Reference to a nucleotide sequence as set out herein encompasses a DNA molecule with the specified sequence, and encompasses a RNA molecule with the specified sequence in which U is substituted for T, unless context requires otherwise.

A method of production of an antibody VH variable domain, the method including causing expression from encoding nucleic acid is also described. Such a method may comprise culturing host cells under conditions for production of said antibody VH variable domain.

A method of production may comprise a step of isolation and/or purification of the product. A method of production may comprise formulating the product into a composition including at least one additional component, such as a pharmaceutically acceptable excipient.

Systems for cloning and expression of a polypeptide in a variety of different host cells are well known. Suitable host cells include bacteria, mammalian cells, plant cells, filamentous fungi, yeast and baculovirus systems and transgenic plants and animals. The expression of antibodies and antibody fragments in prokaryotic cells is well established in the art. For a review, see for example Pluckthun (1991), Bio/Technology 9: 545-551. A common bacterial host is *E. coli*.

Expression in eukaryotic cells in culture is also available to those skilled in the art as an option for production of a specific binding member for example Chadd et al. (2001), Current Opinion in Biotechnology 12: 188-194); Andersen et al. (2002) Current Opinion in Biotechnology 13: 117; Larrick & Thomas (2001) Current Opinion in Biotechnology 12:411-418. Mammalian cell lines available in the art for expression of a heterologous polypeptide include Chinese hamster ovary (CHO) cells, HeLa cells, baby hamster kidney cells, NS0 mouse melanoma cells, YB2/0 rat myeloma cells, human embryonic kidney cells, human embryonic retina cells and many others.

Suitable vectors can be chosen or constructed, containing appropriate regulatory sequences, including promoter sequences, terminator sequences, polyadenylation sequences, enhancer sequences, marker genes and other sequences as appropriate. Vectors may be plasmids e.g. phagemid, or viral e.g. 'phage, as appropriate. For further details see, for example, Sambrook & Russell (2001) *Molecular Cloning: a Laboratory Manual:* 3rd edition, Cold Spring Harbor Laboratory Press. Many known techniques and protocols for manipulation of nucleic acid, for example in preparation of nucleic acid constructs, mutagenesis, sequencing, introduction of DNA into cells and gene expression, and analysis of proteins, are described in detail in Ausubel et al. (1999) 4$^{th}$ eds., *Short Protocols in Molecular*

*Biology: A Compendium of Methods from Current Protocols in Molecular Biology*, John Wiley & Sons.

A host cell may contain a nucleic acid as described herein. Such a host cell may be in vitro and may be in culture. Such a host cell may be in vivo. In vivo presence of the host cell may allow intracellular expression of a binding member for use in the present invention as "intrabodies" or intracellular antibodies. Intrabodies may be used for gene therapy.

A method comprising introducing a nucleic acid disclosed herein into a host cell is also described. The introduction may employ any available technique. For eukaryotic cells, suitable techniques may include calcium phosphate transfection, DEAE-Dextran, electroporation, liposome-mediated transfection and transduction using retrovirus or other virus, e.g. vaccinia or, for insect cells, baculovirus. Introducing nucleic acid in the host cell, in particular a eukaryotic cell may use a viral or a plasmid based system. The plasmid system may be maintained episomally or may be incorporated into the host cell or into an artificial chromosome. Incorporation may be either by random or targeted integration of one or more copies at single or multiple loci. For bacterial cells, suitable techniques may include calcium chloride transformation, electroporation and transfection using bacteriophage.

The introduction may be followed by causing or allowing expression from the nucleic acid, e.g. by culturing host cells under conditions for expression of the gene. The purification of the expressed product may be achieved by methods known to one of skill in the art.

The nucleic acid may be integrated into the genome (e.g. chromosome) of the host cell. Integration may be promoted by inclusion of sequences that promote recombination with the genome, in accordance with standard techniques.

A method that comprises using a construct as stated above in an expression system in order to express a specific binding member or polypeptide as above is also described.

Specific binding members of the present invention are designed to be used in methods of diagnosis or treatment in human or animal subjects, e.g. human. Specific binding members of the invention may be used in the diagnosis or treatment of cancer.

Accordingly, the invention provides methods of treatment comprising administration of a specific binding member as described, pharmaceutical compositions comprising such a specific binding member, and use of such a specific binding member in the manufacture of a medicament for administration, for example in a method of making a medicament or pharmaceutical composition comprising formulating the specific binding member with a pharmaceutically acceptable excipient. Pharmaceutically acceptable vehicles are well known and will be adapted by the person skilled in the art as a function of the nature and of the mode of administration of the active compound(s) chosen.

Specific binding members of the present invention will usually be administered in the form of a pharmaceutical composition, which may comprise at least one component in addition to the specific binding member. Thus, pharmaceutical compositions described herein, and for use in accordance with the present invention, may comprise, in addition to active ingredient, a pharmaceutically acceptable excipient, carrier, buffer, stabilizer or other materials well known to those skilled in the art. Such materials should be non-toxic and should not interfere with the efficacy of the active ingredient. The precise nature of the carrier or other material will depend on the route of administration, which may be oral, inhaled or by injection, e.g. intravenous.

Pharmaceutical compositions for oral administration such as for example nanobodies etc are also envisaged in the present invention. Such oral formulations may be in tablet, capsule, powder, liquid or semi-solid form. A tablet may comprise a solid carrier such as gelatin or an adjuvant. Liquid pharmaceutical compositions generally comprise a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included.

For intravenous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilizers, buffers, antioxidants and/or other additives may be employed, as required. Many methods for the preparation of pharmaceutical formulations are known to those skilled in the art. See e.g. Robinson ed., Sustained and Controlled Release Drug Delivery Systems, Marcel Dekker, Inc., New York, 1978.

A composition may be administered alone or in combination with other treatments, concurrently or sequentially or as a combined preparation with another therapeutic agent or agents, dependent upon the condition to be treated.

A specific binding member of the present invention may be used as part of a combination therapy in conjunction with an additional medicinal component. Combination treatments may be used to provide significant synergistic effects, particularly the combination of a specific binding member for use in the present invention with one or more other drugs. A specific binding member for use in the present invention may be administered concurrently or sequentially or as a combined preparation with another therapeutic agent or agents, for the treatment of one or more of the conditions listed herein.

For example, a specific binding member of the invention may be used in combination with an existing therapeutic agent for the treatment of cancer, in particular cancers expressing CAIX.

A specific binding member of the invention and one or more of the above additional medicinal components may be used in the manufacture of a medicament. The medicament may be for separate or combined administration to an individual, and accordingly may comprise the specific binding member and the additional component as a combined preparation or as separate preparations. Separate preparations may be used to facilitate separate and sequential or simultaneous administration, and allow administration of the components by different routes e.g. oral and parenteral administration.

In accordance with the present invention, compositions provided may be administered to mammals. Administration may be in a "therapeutically effective amount", this being sufficient to show benefit to a patient. Such benefit may be at least amelioration of at least one symptom. Thus "treatment of cancer" refers to amelioration of at least one symptom. The actual amount administered, and rate and time-course of administration, will depend on the nature and severity of what is being treated, the particular mammal being treated, the clinical condition of the individual patient, the cause of the disorder, the site of delivery of the composition, the type of specific binding member, the method of administration, the scheduling of administration and other factors known to medical practitioners. Prescription of treatment, e.g. decisions on dosage etc, is within the responsibility of general practitioners and other medical doctors, and may depend on the severity of the symptoms and/or progression of a disease being treated. Appropriate doses of antibody are well known in the art (Ledermann et al. (1991) Int. J. Cancer 47: 659-664; and Bagshawe et al. (1991)

Antibody, Immunoconjugates and Radiopharmaceuticals 4: 915-922). Specific dosages indicated herein, or in the Physician's Desk Reference (2003) as appropriate for the type of medicament being administered, may be used. A therapeutically effective amount or suitable dose of a specific binding member of the invention can be determined by comparing its in vitro activity and in vivo activity in an animal model. Methods for extrapolation of effective dosages in mice and other test animals to humans are known. The precise dose will depend upon a number of factors, including whether the antibody is for diagnosis, prevention or for treatment, the size and location of the area to be treated, the precise nature of the antibody (e.g. whole antibody, fragment or diabody), and the nature of any detectable label or other molecule attached to the antibody. A typical antibody dose will be in the range 100 μg to 1 g for systemic applications, and 1 μg to 1 mg for topical applications. An initial higher loading dose, followed by one or more lower doses, may be administered. An antibody may be a whole antibody, e.g. the IgG1 or IgG4 isotype. This is a dose for a single treatment of an adult patient, which may be proportionally adjusted for children and infants, and also adjusted for other antibody formats in proportion to molecular weight. Treatments may be repeated at daily, twice-weekly, weekly or monthly intervals, at the discretion of the physician. Treatments may be every two to four weeks for subcutaneous administration and every four to eight weeks for intravenous administration. In some embodiments of the present invention, treatment is periodic, and the period between administrations is about two weeks or more, e.g. about three weeks or more, about four weeks or more, or about once a month. In other embodiments of the invention, treatment may be given before, and/or after surgery, and may be administered or applied directly at the anatomical site of surgical treatment.

Further aspects and embodiments of the invention will be apparent to those skilled in the art given the present disclosure including the following experimental exemplification.

All documents mentioned in this specification are incorporated herein by reference in their entirety.

"and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

Unless context dictates otherwise, the descriptions and definitions of the features set out above are not limited to any particular aspect or embodiment of the invention and apply equally to all aspects and embodiments which are described.

Certain aspects and embodiments of the invention will now be illustrated by way of example and with reference to the figures described above.

EXPERIMENTAL

Example 1: Isolation of the XE114 Single Chain Fv Against CAIX

Materials and Methods
Isolation of the XE114 Single Chain Fv Against CAIX
120 pmol of biotinylated His-tagged CAIX (amino acids 120-397 of the full-length protein; SEQ ID NO: 15) were incubated with 60 μL of streptavidin-coated dynabeads for 30 minutes at room temperature with agitation. Unbound CAIX antigen was washed from the beads 3× with PBS pH 7.4. The antigen-bead complex was incubated with $10^{12}$ transforming units (t.u.) of phage antibodies in 1 mL 2% milk in PBS for 1 hr with rotation at room temperature. Unbound phage were washed from the beads using 6×1 mL PBST followed by 6×1 mL PBS. Bound phage were eluted from the beads by addition of 800 μL 100 mM TAE and incubation for 5 min. The eluted phage were immediately neutralized by the addition of 200 μL 1M Tris pH 7.4. Once eluted and neutralized, the phage were used to infect exponentially growing *E. coli* TG1 cells.

Two rounds of panning were performed against His-tagged CAIX (SEQ ID NO: 15) and the selection outputs were tested for binding to His-tagged CAIX (SEQ ID NO: 15) in an ELISA.

BIAcore Screening of Positive Clones
Clones giving a positive signal in an ELISA were screened by BIAcore to confirm which scFvs were able to bind to CAIX. Supernatant screening was performed on a Biacore 3000 instrument. 2100 response units (RU) of recombinant His-tagged CAIX (SEQ ID NO: 15) were immobilized onto a CM5 chip. 15 μL of each supernatant was allowed to flow over the coated chip at a flow rate of 10 μL/min. Positive clones were identified and sequenced.

Sequencing of scFvs Specific for CAIX
Positive clones identified by BIAcore screening, including the anti-CAIX scFv antibody XE114, were sequenced using conventional methods to identify unique scFvs.

Figure 2:
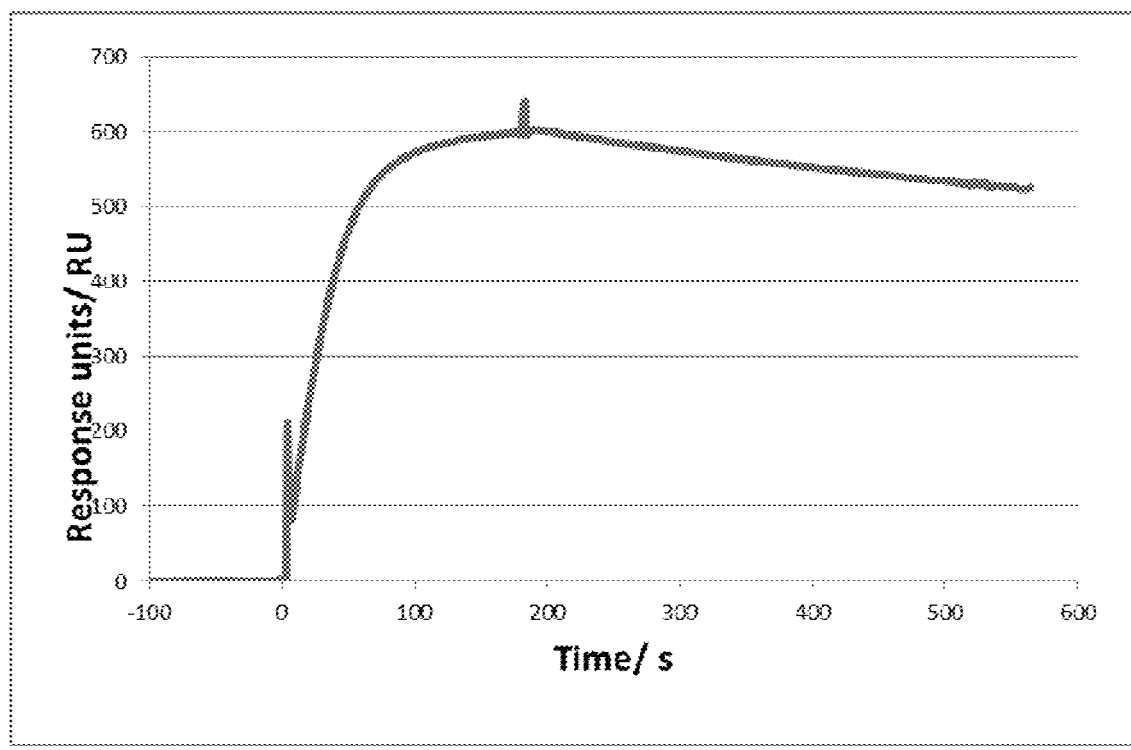
FIG. 2 shows the results of a Biacore analysis to measure the affinity of the anti-CAIX XE114 scFv antibody (with the glycosylation motif) for the extracellular domain of CAIX. Based on the results of the analysis shown in FIG. 2, the $K_d$ of the anti-CAIX XE114 antibody for the extracellular domain of CAIX when measured at a concentration of 660 nM was calculated to be 15 nM.

Affinity Measurements by BIAcore
Affinity measurements were performed on a Biacore 3000 instrument. 2100 RU recombinant His-tagged CAIX (SEQ ID NO: 15) were immobilized onto a CM5 chip. Peaks representing the monomeric fractions of the scFv were collected by size-exclusion chromatography on a Superdex 75 HR 10/30 column. The monomeric fraction was injected at a flow rate of 10 μl min$^{-1}$ over the antigen-coated chip at four different concentrations, 660 nM, 160 nM and 80 nM. All kinetic data were evaluated using the BIAevaluation 4.1 software. The results of affinity measurement of the XE114 antibody at a concentration of 660 nM are shown in FIG. 2.

Epitope Mapping by BIAcore
The epitope on CAIX bound by the scFv XE114 antibody was mapped through comparison with a second CAIX-binding scFv antibody, A3 (Ahlskog et al., British Journal of Cancer, 2009, 101:645-657) using a Biacore 3000 instrument. 2100 RU recombinant His-tagged CAIX (SEQ ID NO: 15) were immobilized onto a CM5 chip. 30 μL of the scFv A3 antibody at a concentration of 0.1 mg/mL was injected over the antigen-coated chip at a flow rate of 10 μl min$^{-1}$.

Figure 3:
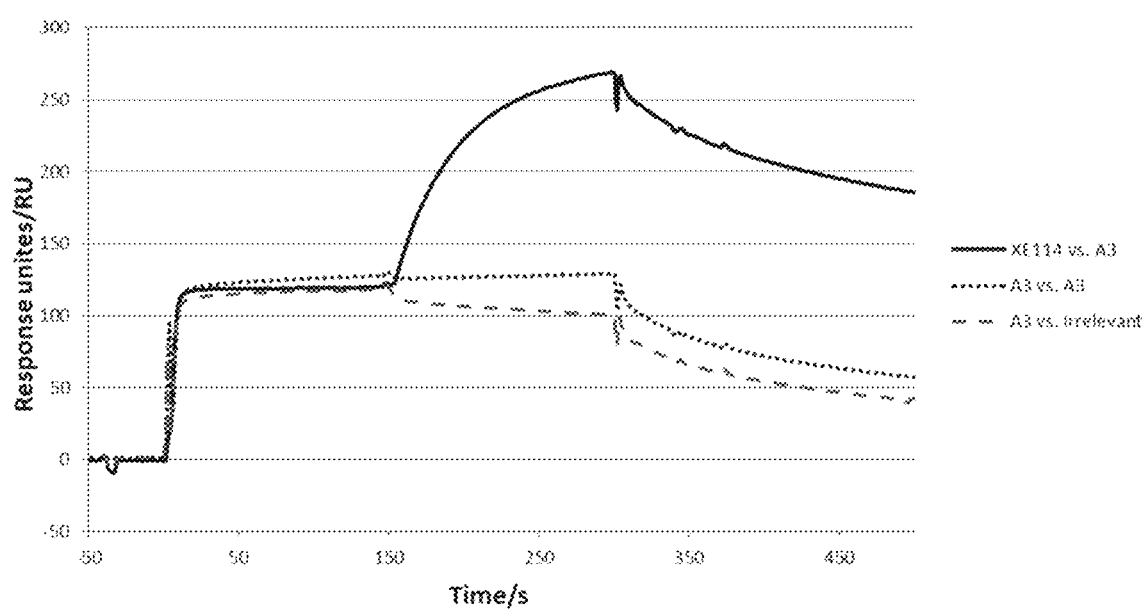
FIG. 3 shows epitope mapping of the anti-CAIX XE114 scFv antibody (with the glycosylation motif) by comparison with the anti-CAIX A3 antibody (Ahlskog et al., British Journal of Cancer, 2009, 101: 645-657).

To determine whether the scFv XE114 antibody binds to an epitope on CAIX distinct from the scFv A3 epitope, a second 30 μL injection was performed with a 1:1 mixture of the scFv A3 and the scFv XE114. The total protein concentration was 0.1 mg/mL (0.05 mg/mL A3+0.05 mg/mL XE114) and the sample was injected over the antigen coated chip at a flow rate of 10 μl min$^{-1}$. Two control reactions were performed where the second injection consisted of either 30 μL of the scFv A3 or 30 μL of a 1:1 mixture of the scFv A3 and an irrelevant scFv antibody that does not bind CAIX. The results of this experiment are shown in FIG. 3.

In Vitro Immunofluorescence Staining of SKRC52 Tumors
Frozen human renal cell carcinoma (SKRC52) tumor sections were stained as follows.

Biotin-labeled antibody XE114 in diabody (Db) format was added at a final concentration of 5 μg/ml to acetone-fixed SKRC52 tumour sections. Binding of the biotin-labelled XE114 antibody to the tumour sections was determined using AlexaFluor488-conjugated streptavidin (final dilution 1:500). As a negative control an irrelevant antibody specific for hen egg lysozyme was used.

Figure 4:
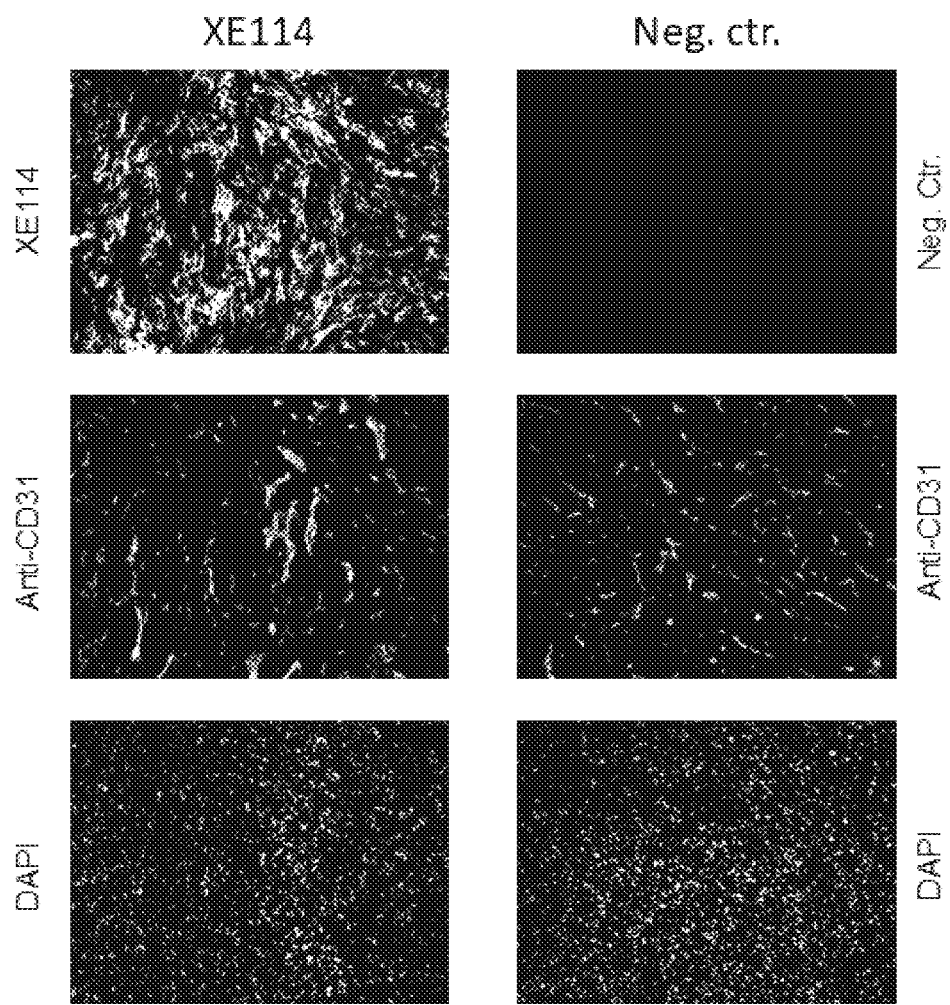
FIG. 4 shows the results of in vitro immunofluorescence staining of human renal cell carcinoma (SKRC52) tumor sections with biotin-labeled antibody XE114 (with the glycosylation motif) in diabody format, as well as an antibody specific for hen egg lysozyme as a negative control (Neg.ctr.). The results of counterstaining of the tumour blood vessels with a rat anti-murine CD31 antibody and the cell nuclei with DAPI is also shown.

Counterstaining for tumor blood vessels was performed using a rat anti-murine CD31 antibody (final dilution 1:200), followed by detection with AlexaFluor594-conjugated donkey anti-rat-IgG (final dilution 1:500). The staining of tumour cell nuclei was performed with DAPI. Tumour sections were mounted with fluorescent mounting medium and analysed using an Axioskop2 microscope with a 10× objective. The results of the in vitro immunofluorescence analyses of the SKRC52 tumor sections are shown in FIG. 4.

Ex Vivo Immunofluorescence Staining of SKRC52 Tumors

BALB/c nude mice bearing subcutaneously implanted SKRC52 human renal cell carcinoma tumours were injected with 100 µg of XE114 antibody in IgG format or an antibody specific for hen egg lysozyme as a negative control. 60 h after injection, mice were sacrificed and the tumors were collected and frozen.

The XE114 antibody was detected using a Rabbit anti-huIgG (final dilution 1:500). Antibody binding to sections of the harvested tumours was revealed with a goat anti-rabbit AlexaFluor488-conjugated antibody (final dilution 1:500).

Figure 5:
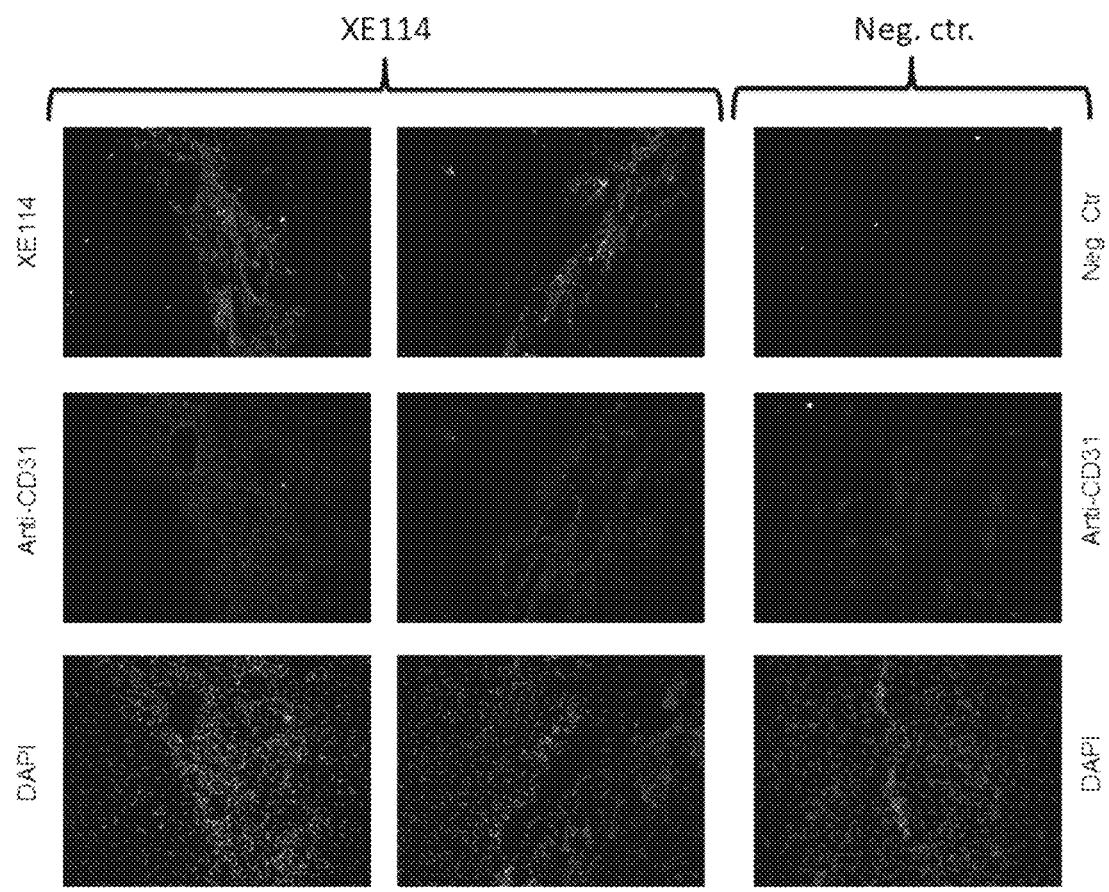
FIG. 5 shows the results of ex vivo immunofluorescence staining of SKRC52 tumor sections with the XE114 antibody (with the glycosylation motif) in IgG format, as well as an antibody specific for hen egg lysozyme as a negative control (Neg.ctr.). The results of counterstaining of the tumour blood vessels with a rat anti-murine CD31 antibody and the cell nuclei with DAPI is also shown.

Counterstaining for blood vessels was performed with a rat anti-murine CD31 antibody (final dilution 1:200), followed by detection with AlexaFluor594-conjugated donkey anti-Rat-IgG (final dilution 1:500). The staining of cell nuclei was performed with DAPI. Tumour sections were mounted with fluorescent mounting medium and analysed using an Axioskop2 microscope with a 10× objective. The results of the ex vivo immunofluorescence analyses of the SKRC52 tumor sections are shown in FIG. 5.

Immunofluorescence Staining of Human Stomach Tissue

Frozen sections of healthy human stomach tissue were stained as follows. Briefly, FITC-labeled antibody XE114 in human IgG1 (hIgG1) format was added at a final concentration of 2 µg/ml to acetone-fixed sections. Detection of the primary antibody was performed with a rabbit anti-FITC antibody (final dilution 1:1000) and binding of the primary antibody to the tissue sections was revealed with a goat anti-rabbit AlexaFluor488-conjugated antibody (final dilution 1:500).

Figure 6:
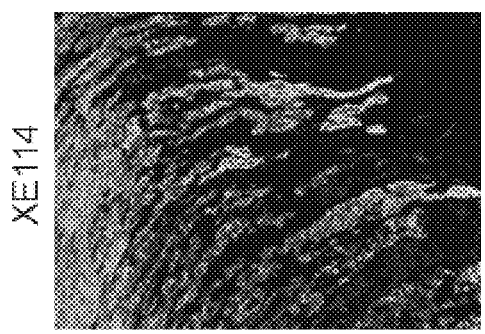
FIG. 6 shows the results of immunofluorescence staining of human stomach tissue. Frozen healthy human stomach tissue sections with the FITC-labeled antibody XE114 (with the glycosylation motif) in hIgG1 format. The results of cell nuclei with DAPI is also shown.
Figure 6:
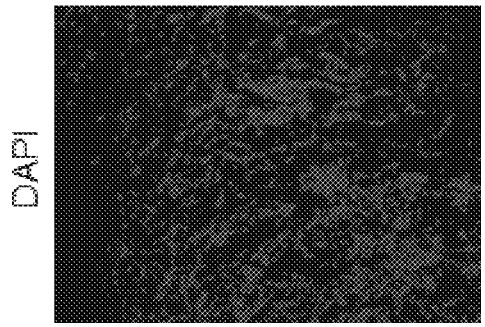

Counterstaining for cell nuclei was performed with DAPI. Tissue sections were mounted with fluorescent mounting medium and analysed using an Axioskop2 microscope with a 10× objective. The results of the immunofluorescence analyses of the human stomach tissue sections are shown in FIG. 6.

FACS Analyses of SKRC52 Cells

Figure 7:
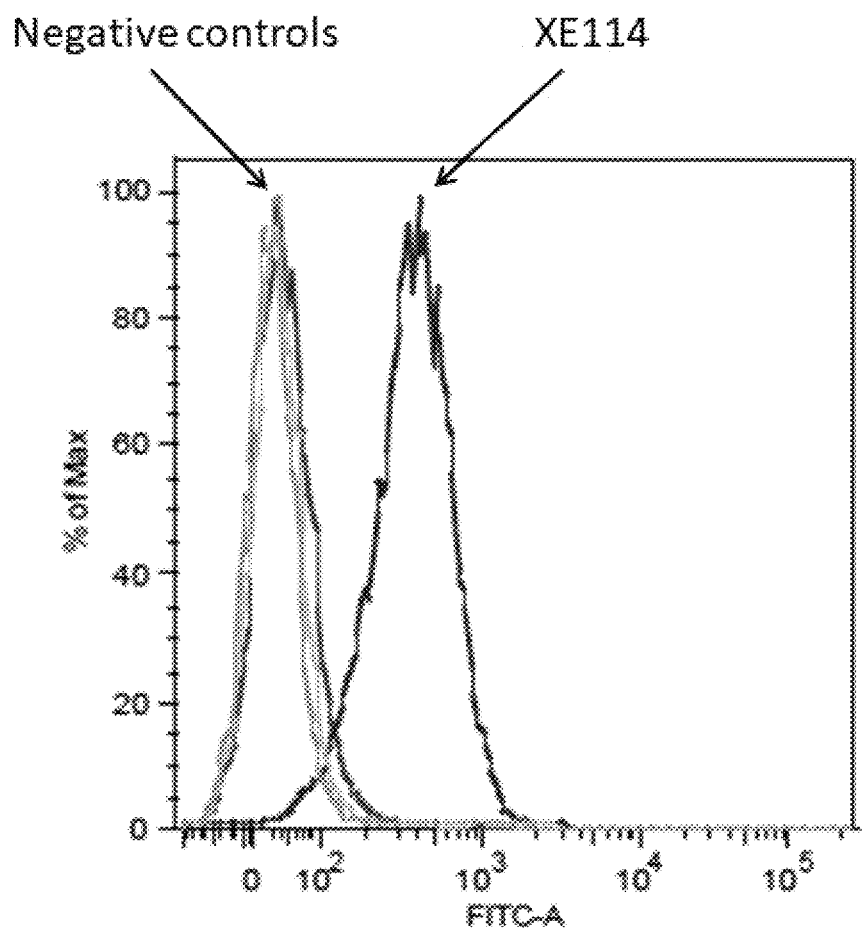
FIG. 7 shows the results of FACS analyses of SKRC52 cells, stained with the XE114 antibody (with the glycosylation motif) in diabody format or negative controls. The XE114 antibody showed a clear and selective binding to SKRC52 cells compared with the negative controls.

SKRC52 cells were harvested and concentrated in blocking solution (PBS, 1% decomplemented FBS) to 5mio cells/mL: 500 µL of this cell solution were used for each single staining. Cells were incubated with 250 µL of biotinylated XE114 in diabody (Db) format diluted to 10 µg/mL in blocking solution or with a control antibody specific for hen egg lysozyme. After washing, cells were incubated in the dark with 250 µL of AlexaFluor488-conjugated Streptavidin diluted 1:500 in blocking solution. After washings, cells were transferred into FACS tubes and analyzed with a BD FACSCanto Flow Cytometer. The results of the FACS analyses of the SKRC52 cells are shown in FIG. 7.

Biodistribution

The XE114 in diabody format was produced in CHO-S cells by transient gene expression and purified by means of Protein A—Sepharose affinity chromatography resin. Protein purity was assessed by Size Exclusion Chromatography (Superdex200, Running buffer: PBS, pH 7.40).

Figure 8:
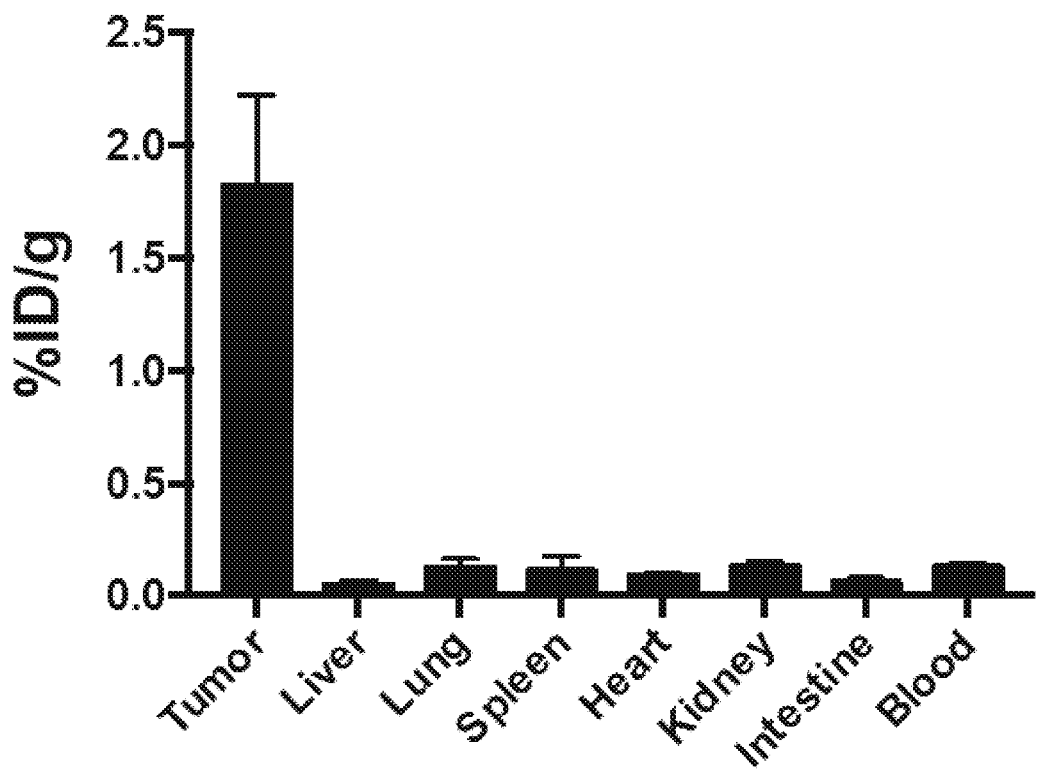
FIG. 8 shows the in vivo targeting performance of XE114 antibody (with the glycosylation motif) by biodistribution analysis in BALB/c nude mice bearing subcutaneously implanted SKRC52 human renal cell carcinoma tumours.

The in vivo targeting performance of the XE114 in diabody format was evaluated by biodistribution analysis. After radio-iodination with $^{125}$I, a total of 10 µg of radio-labelled antibody were injected into the tail vein of BALB/c nude mice bearing subcutaneously implanted SKRC52 human renal cell carcinoma tumours. Mice were sacrificed 24 h after injection. Organs were weighed and radioactivity was counted with a Packard Cobra gamma counter. The radioactive content of representative organs was recorded and expressed as a percentage of the injected dose per gram of tissue (% ID/g). The results of the analyses are shown in FIG. 8.

Results

Isolation of the XE114 Single Chain Fv Against CAIX

After two rounds of panning, 480 bacterial supernatants containing expressed scFv were screened for their ability to bind CAIX in an ELISA. 86 of the screened bacterial supernatants gave a positive signal in the ELISA and were harvested and subjected to BIAcore analysis.

BIAcore Screening of Positive Clones 60 of the screened supernatants giving the highest positive signals in the ELISA were analysed for CAIX binding by BIAcore. Single chain Fvs from 16 of the supernatants that showed binding to CAIX by BIAcore were sequenced. Eleven unique sequences were identified and these 11 scFvs were expressed and purified. From these molecules the scFv XE114 was identified as the antibody with the highest affinity for CAIX.

Sequencing of scFvs Specific for CAIX

The nucleotide sequence of the anti-CAIX scFv antibody XE114 is shown in SEQ ID NO: 14. The amino acid sequence of this antibody is shown in SEQ ID NO: 10, as well as in FIG. 1.

Affinity Measurements by BIAcore

The $K_d$ of the anti-CAIX XE114 antibody for CAIX when measured at a concentration of 660 nM was 15 nM (FIG. 2).

Epitope Mapping by BIAcore

The results of the eptiope mapping (FIG. 3) show that antibody XE114 binds to an epitope on CAIX distinct from the epitope bound by the known anti-CAIX antibody A3.

In Vitro Immunofluorescence Staining of SKRC52 Tumors

The results of the immunofluorescence experiments (FIG. 4) show that the XE114 antibody specifically and strongly stained the renal cell carcinoma (SKRC52) tumor tissue, while no staining of the tumour tissue was observed with the control antibody.

Ex Vivo Immunofluorescence Staining of SKRC52 Tumors

The XE114 antibody showed specific accumulation at tumor site, while no such accumulation was seen with the control antibody.

Immunofluorescence Staining of Human Stomach Tissue

Strong staining of the stomach tissue was observed with the XE114 antibody, which is in line with the pattern of expression reported for the cognate antigen of the antibody, CAIX.

FACS Analyses of SKRC52 Cells

The XE114 antibody showed clear and selective binding to SKRC52 cells compared with the negative controls for which no binding was observed.

Biodistribution

The XE114 antibody showed a selective uptake into the SKRC52 tumors with an optimal tumor to organs and tumor to blood ratio.

Example 2: Production and Characterisazion of the XE114 without Glycosylation Motif in Single Chain Fv and IgG Format Material & Methods Cloning, Purification and In Vitro Characterization of the XE114 Antibody without Glycosylation Motif in scFv Format Primers were designed in order to mutate the asparagine at position 88 of the VL domain of the XE114 scFv to glutamine. The gene encoding for the XE114 antibody without glycosylation motif was PCR amplified using the primers "Leader Seq DP47 Fo>" (SEQ ID No 26) and "Not STOP DPL16 Ba<" (SEQ ID No 27). The resulting PCR fragment was further amplified using the primers and "NheI leader >" (SEQ ID No 28) and "Not STOP DPL16 Ba<" (SEQ ID No 29). This PCR fragment was then digested with NheI and NotI and cloned into the pCDNA 3.1 vector.

Production Process

The XE114 antibody without glycosylation motif in scFv format was expressed using transient gene expression in CHO-S cells. For 1 mL of production $4 \times 10^6$ CHO-S cells in suspension were centrifuged and resuspended in 1 mL ProCHO4. 0.625 µg of plasmid DNAs followed by 2.5 µg polyethylene imine (PEI; 1 mg/mL solution in water at pH 7.0) per million cells were then added to the cells and gently mixed. The transfected cultures were incubated in a shaker incubator at 31° C. for 6 days. The protein was purified from the cell culture medium by protein A affinity chromatography and then dialyzed against PBS.

Protein Characterization

The XE114 antibody without glycosylation motif in scFv format was further analyzed by Size-exclusion chromatography on a Superdex 75 increase 10/300 GL column on an ÄKTA FPLC.

For ESI-MS analysis, the XE114 antibody without glycosylation motif in scFv format was diluted to about 0.1 mg/mL and LC-MS was performed on a Waters Xevo G2XS Qtof instrument (ESI-ToF-MS) coupled to a Waters Acquity UPLC H-Class System using a 2.1×50 mm Acquity BEH300 C4 1.7 µm column.

Cloning, Purification and In Vitro Characterization of the XE114 Antibody without Glycosylation Motif in IgG Format Cloning The IgG1(XE114) antibody gene was cloned in vector pMM137 using the methods described in Zuberbuhler et al., Protein Eng. Des. Sel.

(2009) 22, 169. In order to abrogate glycosylation, the asparagine at position 88 of the VL domain of the XE114 in IgG1 format was mutated to glutamine, following the strategy described in Gébleux et al. Int. J. Cancer (2017) 140, 1670.

Cell Culture

CHO-S cells transfected with the pMM137 vector encoding the IgG1(XE114) antibody without the glycosylation motif were cultured in suspension in PowerCHO-2CD medium, supplemented with Ultraglutamine-1, HT-supplement and Antibiotic-Antimycotic.

Protein Production and Purification

The XE114 antibody without glycosylation motif in IgG format was expressed in CHO-S cells by transient gene expression. Briefly, CHO cells in suspension were first counted and resuspended in fresh ProCHO medium to a final cells concentration of $4 \times 10^1$ cells/mL. 0.9 µg/million cells DNA and 2.5 µg/million cells PEI were added carefully to the cells. Cells were incubated in a shaker at 31° C.×150 rpm for 6 days. After incubation the suspension was centrifuged at 4° C.×6500 rpm for 25 minutes (SLA-3000 rotor) using Sorvall RC 5C Plus centrifuge. Supernatant was harvested and filtered using a PD-10 column and loaded onto a protein A column. The column was thereafter washed with 200 mL of Buffer A (100 mM NaCl, 0.5 mM EDTA, 0.1% Tween 20 in PBS) and then with 200 mL Buffer B (500 mM NaCl, 0.5 mM EDTA in PBS). The antibody product was eluted using 10-15 mL 0.1 M glycine at pH=3 and fractions of 1 mL were collected. The OD at an absorbance of 280 nm ($OD_{280}$) was measured and fractions containing protein ($OD_{280}$>0.1 mg/mL) were pooled and loaded on SpectraPor dialysis membrane MW 12-14000 and dialysed in PBS o/n at 4° C. After dialysis, the XE114 antibody without glycosylation motif in IgG format was characterized by SDS-PAGE, size exclusion chromatography and mass spectrometry.

Affinity Measurements

Affinity measurements were performed by surface plasmon resonance using BIAcore X100 instrument using a CAIX coated CM5 chip. The XE114 antibody without glycosylation motif in scFv format was injected as serial-dilutions, in a concentration range from 1 mM to 15.7 nM. Regeneration of the chip was performed by HCl 10 mM.

Results

Figure 9:
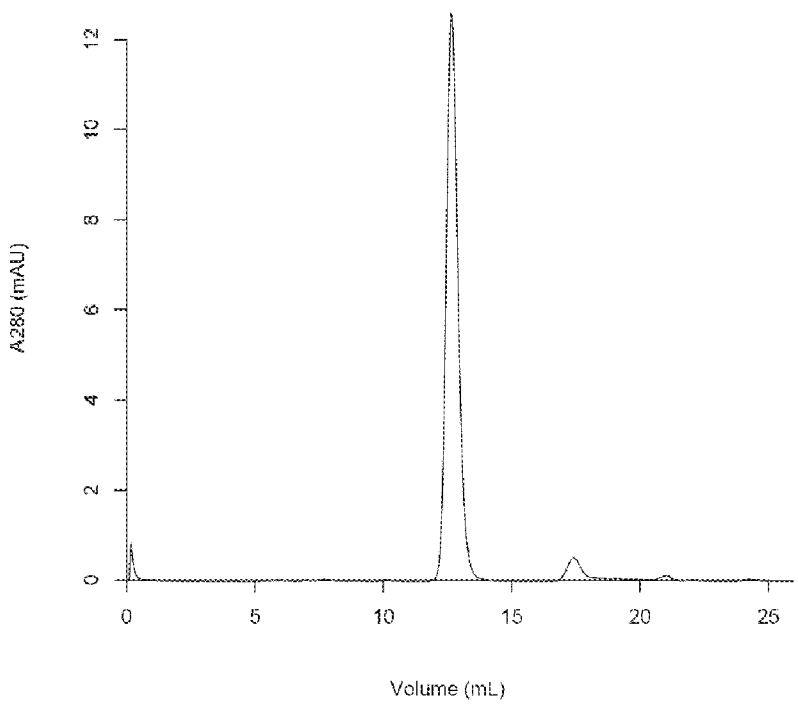
FIG. 9 shows (A) the size exclusion chromatography profile and (B) ESI-MS profile analysis of the XE114 antibody in scFv format without the glycosylation motif.
Figure 9:
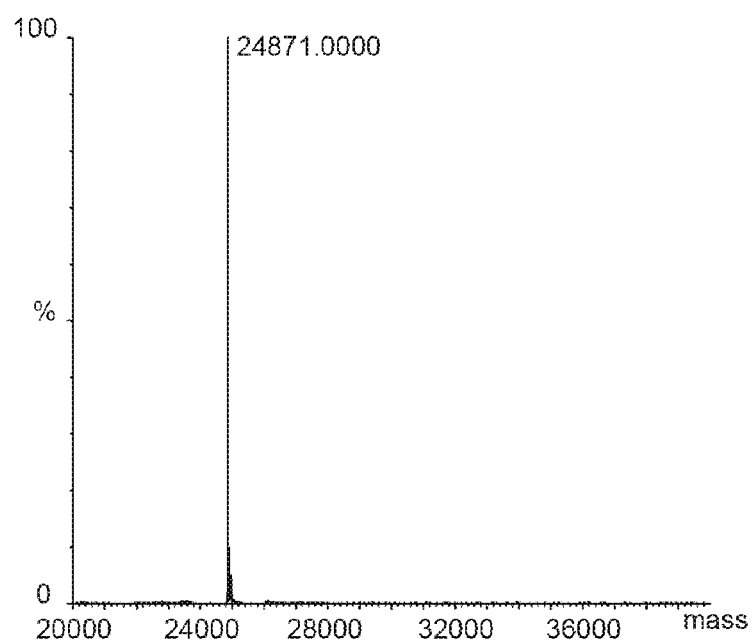

Cloning, Purification and In Vitro Characterization of the XE114 Antibody without Glycosylation Motif in scFv Format The XE114 antibody without glycosylation motif in scFv format was expressed in CHO cells and purified to homogeneity exploiting the binding properties of the VH domain of the XE114 antibody to Protein A resin as described above. The produced antibody was of an excellent quality as evidenced by the single peak observed by gel filtration which corresponds to the monomeric fraction (FIG. 9A). The MS analysis confirmed that the XE114 antibody without glycosylation motif in scFv format had the expected molecular weight under reducing (R) and non-reducing (NR) conditions (FIG. 9B).

Affinity Measurements

The BIAcore analysis confirmed that the XE114 antibody without glycosylation motif in scFv format was capable of binding to CAIX. The results are summarised in Table 1.

TABLE 1

| | Antibody Format | KD (nM) | $K_{off}(s^{-1})$ ($\times 10^{-4}$) |
|---|---|---|---|
| XE114 w/o glycosylation motif | scFv | 2.71 | 3.05 |

Example 3: Production and Characterisazion of the hIL2-XE114-hTNF$^{mut}$ Conjugate Material & Methods The XE114 antibody in scFv format without glycosylation motif was simultaneously fused to both human interleukin 2 (hIL2) and human tumor necrosis factor alpha (hTNFα). The hIL2-XE114-hTNF$^{mut}$ conjugate is a fully-human immunostimulatory product that recognizes carbonic anhydrase IX (CAIX). The IL2 is a cytokine that stimulates immune effector cells, while TNF is a strong pro-inflammatory cytokine. Considering that TNF is ten times more potent than IL2, to match the biological activity of the two cytokines a single point mutation in the TNF moiety was introduced.

Cloning of hIL2-XE114-hTNF$^{mut}$ conjugate

Primers were designed in order to mutate the asparagine at position 88 of the VL domain of the XE114 antibody in scFv format to glutamine to remove the glycosylation motif. In addition, primers were designed in order to mutate the arginine at position 32 of the TNF domain to alanine. The gene coding for the XE114 antibody in scFv format without glycosylation motif was PCR amplified using the primers "Link-F8VH>" (SEQ ID NO: 30) and "VL-link(15aa)-lamda ba" (SEQ ID NO: 31). The gene encoding for human IL2 was PCR amplified using the primers "NheI leader >" (SEQ ID NO: 28) and "hIL2-Li12aa<" (SEQ ID NO: 32). The gene coding for the mutant human TNF was PCR amplified using the primers "link-hsTNF>" (SEQ ID NO: 33) and "NotISTOP-hsTNF<" (SEQ ID NO: 34). These three fragments were then assembled by PCR, digested with NheI and NotI and cloned into the pCDNA 3.1 vector. The hIL2-XE114-hTNF$^{mut}$ conjugate has the amino acid sequence set forth in SEQ ID NO 24.

Cloning of IL2-KSF-TNF$^{mut}$ Conjugate

An IL2-KSF-TNF$^{mut}$ conjugate was prepared to act as a negative control for the hIL2-XE114-hTNF$^{mut}$ conjugate.

Primers were designed in order to mutate the arginine at position 32 of the TNF domain to alanine. The gene coding for the KSF antibody in scFv format was PCR amplified using the primers "Link-F8VH>" (SEQ ID NO: 30) and "VL-link(15aa)-lamda ba" (SEQ ID NO: 31). The gene coding for human IL2 was PCR amplified using the primers "NheI leader >" (SEQ ID NO: 28) and "hIL2-Li12aa<" (SEQ ID NO: 32). The gene coding for the human mutant TNF described above was PCR amplified using the primers "link-hsTNF>" (SEQ ID NO: 33) and "NotISTOP-hsTNF<" (SEQ ID NO: 34). These three fragments were then assembled by PCR, digested with NheI and NotI and cloned into the pCDNA 3.1 vector.

Production of hIL2-XE114-hTNF$^{mut}$ and IL2-KSF-TNF$^{mut}$ Conjugates

The hIL2-XE114-hTNF$^{mut}$ and IL2-KSF-TNF$^{mut}$ conjugates were expressed using transient gene expression in CHO-S cells. For 1 mL of production 4×10$^6$ CHO-S cells in suspension were centrifuged and resuspended in 1 mL ProCH04. 0.625 µg of plasmid DNAs followed by 2.5 µg polyethylene imine (PEI; 1 mg/mL solution in water at pH 7.0) per million cells were then added to the cells and gently mixed. The transfected cultures were incubated in a shaker incubator at 31° C. for 6 days. The conjugates were purified from the cell culture medium by protein A affinity chromatography and then dialyzed against PBS. The result of the production of hIL2-XE114-hINF$^{mut}$ is summarized in Table 2.

TABLE 2

| TGE volume | Elution buffer | Quenching buffer | Dialysis buffer | Yield after dialysis |
|---|---|---|---|---|
| 0.5 L | Glycine 0.1M pH 3.0 | Sodium Acetate 1M pH 5.0 | PBS pH 7.4 | 10.3 mg/L |

Protein Characterization

SDS-PAGE was performed with 10% gels under reducing and non-reducing conditions. The hIL2-XE114-hTNF$^{mut}$ conjugate was further analyzed by Size-exclusion chromatography on a Superdex 200 increase 10/300 GL column on an ÄKTA FPLC.

Affinity Measurements

Affinity measurements were performed by surface plasmon resonance using BIAcore X100 instrument using a CAIX coated SA chip. Samples were injected as serial-dilutions, in a concentration range from 1 mM to 62.5 nM. Regeneration of the chip was performed by HCl 10 mM.

Biological Activities

The biological activity of TNF was determined by incubation with mouse LM fibroblasts, in the presence of 2 µg/mL actinomycin D. In 96-well plates, the cells were incubated in medium supplemented with actinomycin D and varying concentrations of recombinant human TNF or hIL2-XE114-hTNF$^{mut}$. After 24 h at 37° C., cell viability was determined with Cell Titer Aqueous One Solution. Results were expressed as the percentage of cell viability compared to cells treated with actinomycin D only.

The biological activity of IL2 was determined by its ability to stimulate the proliferation of CTLL-2 cells. Cells were seeded in 96-well plates in the culture medium supplemented with varying concentrations of the fusion proteins. After incubation at 37° C. for 48 hours, cell proliferation was determined with Cell Titer Aqueous One Solution.

Flow Cytometry

Antigen expression on SKRC52 cells was confirmed by flow cytometry. Cells were centrifuged and washed in cold FACS buffer (0.5% BSA, 2 mM EDTA in PBS) and stained with hIL2-XE114-hTNF$^{mut}$ conjugate (final concentration 10 µg/mL) and detected with rat anti-IL2 followed by staining with anti-rat AlexaFluor488. IL2-KSF-TNF$^{mut}$ (specific for an irrelevant antigen) was used as a negative control.

Immunofluorescence Studies

CAIX expression was confirmed on ice-cold acetone fixed 8-µm cryostat sections of SKRC52 stained with hIL2-XE114-hTNF$^{mut}$ conjugate (final concentration 5 µg/mL) and detected with rat anti-IL2 and anti-rat AlexaFluor488. For vascular staining goat anti-CD31 and anti-goat AlexaFluor594 antibodies were used. IL2-KSF-TNF$^{mut}$ (specific for an irrelevant antigen) was used as negative control. Slides were mounted with fluorescent mounting medium and analysed with Axioskop2 mot plus microscope.

For ex vivo immunofluorescence analysis, mice were injected with 60 µg hIL2-XE114-hTNF$^{mut}$ or IL2-KSF-TNF$^{mut}$ conjugates and sacrificed 24 hours after injection. Organs were excised and embedded in cryoembedding medium and cryostat section (10 µm) were stained using the following antibodies: rat anti-IL2 and anti-rat AlexaFluor488. For vascular staining goat anti-CD31 and anti-goat AlexaFluor594 antibodies were used. Slides were mounted with fluorescent mounting medium and analysed with Axioskop2 mot plus microscope.

Results

Protein Characterization

Figure 10:
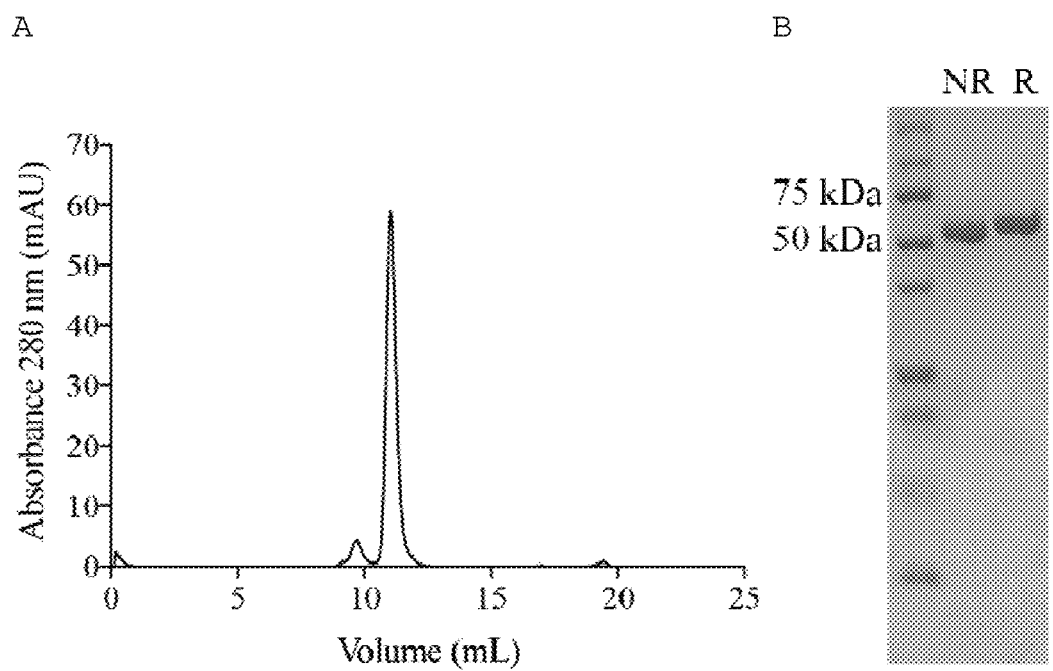
FIG. 10 shows (A) the size exclusion chromatography profile and (B) the SDS-Page analysis of the hIL2-XE114- hTNF$^{mut}$ conjugate (without the glycosylation motif) under reducing conditions (R) and non-reducing conditions (NR).

The hIL2-XE114-hTNF$^{mut}$ conjugate was expressed in CHO-S cells and purified to homogeneity exploiting the binding properties of the VH domain of the XE114 antibody to Protein A resin as described above. The conjugate was produced with excellent quality as evidenced by a single peak in gel filtration (FIG. 10(A)), and a single band in SDS-Page (FIG. 10(B)).

Affinity Measurements

BIAcore analysis confirmed the ability of the XE114 antibody without glycosylation motif in the hIL2-XE114-hTNF$^{mut}$ conjugate to recognize CAIX (FIG. 11).

Biological Activities

Analysis of the in vitro activity of the hIL2-XE114-hTNF$^{mut}$ conjugate indicated that hIL2-XE114-hTNF$^{mut}$ conjugate and the IL2-KSF-TNF$^{mut}$ a reference IL2-based fusion protein displayed a comparable IL2 activity based on a cell line proliferation assay (FIG. 12(A)), while TNF activity was decreased in the mutant TNF present in the hIL2-XE114-hTNF$^{mut}$ conjugate (FIG. 12(B)).

Flow Cytometry

Binding of hIL2-XE114-hTNF$^{mut}$ conjugate to its cognate antigen (CAIX) was assessed and confirmed by flow cytometry on SKRC52 (CAIX+) cells (FIG. 13).

Immunofluorescence Studies

A microscopic fluorescence analysis of SKRC52 xenograft tumor sections confirmed CAIX expression in vivo, by staining with the hIL2-XE114-hTNF$^{mut}$ conjugate (FIG. 14).

Ex Vivo Immunofluorescence Analysis

A microscopic fluorescence analysis of tumor sections, obtained from animals injected with IL2-KSF-TNF$^{mut}$ (KSF antibody specific to an irrelevant antigen) or with the hIL2-XE114-hTNF$^{mut}$ conjugate 24 hours after administration confirmed that hIL2-XE114-hTNF$^{mut}$ conjugate could localize to its cognate CAIX antigen within the tumor mass in proximity to the tumor blood vessels in vivo (FIG. 15).

```
                             Sequence listing

Amino acid sequences of the VH and VL domain CDRs of antibody XE114
VH domain CDR1: SSYAMS (SEQ ID NO: 1)
VH domain CDR2: AIDGSGGSTYYADSVKG (SEQ ID NO: 2)
VH domain CDR3: GPPVFDY (SEQ ID NO: 3)
VL domain CDR1: QGDSLRSYYAS (SEQ ID NO: 4)
VL domain CDR2: GKNNRPS (SEQ ID NO: 5)
VL domain CDR3: NSSKWSWDPVV (SEQ ID NO: 6)

SEQ ID NO: 7 (XE114 antibody VH domain amino acid sequence)
EVQLLESGGGLVQPGGSLRLSCAASGFTFSSYAMSWVRQAPGKGLEWVSAIDGSGGSTYYADSVKGRF
TISRDNSKNTLYLQMNSLRAEDTAVYYCVKGPPVFDYWGQGTLVTVSS SEQ ID NO: 8 (XE114 antibody VL domain amino acid sequence)
SSELTQDPAVSVALGQTVRITCQGDSLRSYYASWYQQKPGQAPVLVIYGKNNRPSGIPDRFSGSSSGN
TASLTITGAQAEDEADYYCNSSKWSWDPVVFGGGTKLTVLG SEQ ID NO: 9 (linker between VH domain and VL domain of XE114 antibody in scFv format)
GGGGSGGGGSGGGG SEQ ID NO: 10 (XE114 antibody amino acid sequence in scFv format)
EVQLLESGGGLVQPGGSLRLSCAASGFTFSSYAMSWVRQAPGKGLEWVSAIDGSGGSTYYADSVKGRF
TISRDNSKNTLYLQMNSLRAEDTAVYYCVKGPPVFDYWGQGTLVTVSSGGGGSGGGGSGGGGSSELTQ
DPAVSVALGQTVRITCQGDSLRSYYASWYQQKPGQAPVLVIYGKNNRPSGIPDRFSGSSSGNTASLTI
TGAQAEDEADYYCNSSKWSWDPVVFGGGTKLTVLG SEQ ID NO: 11 (XE114 antibody VH domain nucleic acid sequence)
GAGGTGCAGCTGTTGGAGTCTGGGGGAGGCTTGGTACAGCCTGGGGGGTCCCTGAGACTCTCCTGTGC
AGCCTCTGGATTCACCTTTAGCAGCTATGCCATGAGCTGGGTCCGCCAGGCTCCAGGGAAGGGGCTGG
AGTGGGTCTCAGCTATTGACGGTAGTGGTGGTAGCACATACTACGCAGACTCCGTGAAGGGCCGGTTC
ACCATCTCCAGAGACAATTCCAAGAACACGCTGTATCTGCAAATGAACAGCCTGAGAGCCGAAGACAC
GGCCGTATATTACTGTGTGAAAGGTCCGCCGGTGTTTGACTACTGGGGCCAGGGAACCCTGGTCACCG
TCTCGAGT SEQ ID NO: 12 (XE114 antibody VL domain nucleic acid sequence)
TCGTCTGAGCTGACTCAGGACCCTGCTGTGTCTGTGGCCTTGGGACAGACAGTCAGGATCACATGCCA
AGGAGACAGTCTCAGAAGCTATTATGCAAGCTGGTACCAGCAGAAGCCAGGACAGGCCCCTGTACTTG
TCATCTATGGTAAAAACAACCGGCCCTCAGGGATCCCAGACCGATTCTCTGGCTCCAGCTCAGGAAAC
ACAGCTTCCTTGACCATCACTGGGGCTCAGGCGGAAGATGAGGCTGACTATTACTGTAATTCCTCTAA
GTGGTCTTGGGATCCCGTGGTATTCGGCGGAGGGACCAAGCTGACCGTCCTAGGC SEQ ID NO: 13 (linker between VH domain and VL domain of XE114 antibody
nucleic acid sequence)
GGTGGAGGCGGTTCAGGCGGAGGTGGCTCTGGCGGTGGCGGA SEQ ID NO: 14 (XE114 scFv antibody nucleic acid sequence)
GAGGTGCAGCTGTTGGAGTCTGGGGGAGGCTTGGTACAGCCTGGGGGGTCCCTGAGACTCTCCTGTGC
AGCCTCTGGATTCACCTTTAGCAGCTATGCCATGAGCTGGGTCCGCCAGGCTCCAGGGAAGGGGCTGG
AGTGGGTCTCAGCTATTGACGGTAGTGGTGGTAGCACATACTACGCAGACTCCGTGAAGGGCCGGTTC
ACCATCTCCAGAGACAATTCCAAGAACACGCTGTATCTGCAAATGAACAGCCTGAGAGCCGAAGACAC
GGCCGTATATTACTGTGTGAAAGGTCCGCCGGTGTTTGACTACTGGGGCCAGGGAACCCTGGTCACCG
TCTCGAGTGGTGGAGGCGGTTCAGGCGGAGGTGGCTCTGGCGGTGGCGGATCGTCTGAGCTGACTCAG
GACCCTGCTGTGTCTGTGGCCTTGGGACAGACAGTCAGGATCACATGCCAAGGAGACAGTCTCAGAAG
CTATTATGCAAGCTGGTACCAGCAGAAGCCAGGACAGGCCCCTGTACTTGTCATCTATGGTAAAAACA
ACCGGCCCTCAGGGATCCCAGACCGATTCTCTGGCTCCAGCTCAGGAAACACAGCTTCCTTGACCATC
ACTGGGGCTCAGGCGGAAGATGAGGCTGACTATTACTGTAATTCCTCTAAGTGGTCTTGGGATCCCGT
GGTATTCGGCGGAGGGACCAAGCTGACCGTCCTAGGC
```

-continued

```
Sequence listing
```

SEQ ID NO: 15 (Sequence of Carbonic Anhydrase IX extracellular domain with
C-terminal His-tag (shown in bold)
GDPQEPQNNAHRDKEGDDQSHWRYGGDPPWPRVSPACAGRFQSPVDIRPQLAAFCPALRPLELLGFQL
PPLPELRLRNNGHSVQLTLPPGLEMALGPGREYRALQLHLHWGAAGRPGSEHTVEGHRFPAEIHVVHL
STAFARVDEALGRPGGLAVLAAFLEEGPEENSAYEQLLSRLEEIAEEGSETQVPGLDISALLPSDFSR
YFQYEGSLTTPPCAQGVIWTVFNQTVMLSAKQLHTLSDTLWGPDSRLQLNFRATQPLNGRVIEASFP
AGVDSSHHHHHH

SEQ ID NO: 16 (Sequence of Carbonic Anhydrase IX extracellular domain)
GDPQEPQNNAHRDKEGDDQSHWRYGGDPPWPRVSPACAGRFQSPVDIRPQLAAFCPALRPLELLGFQL
PPLPELRLRNNGHSVQLTLPPGLEMALGPGREYRALQLHLHWGAAGRPGSEHTVEGHRFPAEIHVVHL
STAFARVDEALGRPGGLAVLAAFLEEGPEENSAYEQLLSRLEEIAEEGSETQVPGLDISALLPSDFSR
YFQYEGSLTTPPCAQGVIWTVFNQTVMLSAKQLHTLSDTLWGPDSRLQLNFRATQPLNGRVIEASFP
AGVDSS SEQ ID NO: 17 (Sequence of Carbonic Anhydrase IX)
MAPLCPSPWL PLLIPAPAPG LTVQLLLSLL LLVPVHPQRL PRMQEDSPLG GGSSGEDDPL
GEEDLPSEED SPREEDPPGE EDLPGEEDLP GEEDLPEVKP KSEEEGSLKL EDLPTVEAPG
DPQEPQNNAH RDKEGDDQSH WRYGGDPPWP RVSPACAGRF QSPVDIRPQL AAFCPALRPL
ELLGFQLPPL PELRLRNNGH SVQLTLPPGL EMALGPGREY RALQLHLHWG AAGRPGSEHT
VEGHRFPAEI HVVHLSTAFA RVDEALGRPG GLAVLAAFLE EGPEENSAYE QLLSRLEEIA
EEGSETQVPG LDISALLPSD FSRYFQYEGS LTTPPCAQGV IWTVFNQTVM LSAKQLHTLS
DTLWGPDSR LQLNFRATQP LNGRVIEASF PAGVDSSPRA AEPVQLNSCL AAGDILALVF
GLLFAVTSVA FLVQMRRQHR RGTKGGVSYR PAEVAETGA SEQ ID NO: 18 (linker between VH domain and VL domain of XE114 antibody
in diabody format)
GGSGG SEQ ID NO: 19 (alternative XE114 antibody LCDR3 without glycosylation motif,
comprising a substitution N -> Q)
The mutation is shown in bold and underlined.
VL domain CDR3: QSSKWSWDPVV SEQ ID NO: 20 (XE114 antibody VL domain amino acid sequence without
glycosylation motif, comprising a substitution N -> Q at position 88)
The mutation is shown in bold and underlined.
SSELTQDPAVSVALGQTVRITCQGDSLRSYYASWYQQKPGQAPVLVIYGKNNRPSGIPDRFSGSSSGN
TASLTITGAQAEDEADYYCQSSKWSWDPVVFGGGTKLTVLG SEQ ID NO: 21 (XE114 antibody Heavy Chain amino acid sequence)
EVQLLESGGGLVQPGGSLRLSCAASGFTFSSYAMSWVRQAPGKGLEWVSAIDGSGG
STYYADSVKGRFTISRDNSKNTLYLQMNSLRAEDTAVYYCVKGPPVFDYWGQGTLVT
VSSASTKGPSVFPLAPSSKSTSGGTAALGCLVKDYFPEPVTVSWNSGALTSGVHTFPA
VLQSSGLYSLSSVVTVPSSSLGTQTYICNVNHKPSNTKVDKKVEPKSSDKTHTSPPSPA
PELLGGPSVFLFPPKPKDTLMISRTPEVTCVVVDVSHEDPEVKFNWYVDGVEVHNAK
TKPREEQYNSTYRVVSVLTVLHQDWLNGKEYKCKVSNKALPAPIEKTISKAKGQPREP
QVYTLPPSRDELTKNQVSLTCLVKGFYPSDIAVEWESNGQPENNYKTTPPVLDSDGSF
FLYSKLTVDKSRWQQGNVFSCSVMHEALHNHYTQKSLSLSPGK SEQ ID NO: 22 (XE114 antibody Light Chain amino acid sequence)
SSELTQDPAVSVALGQTVRITCQGDSLRSYYASWYQQKPGQAPVLVIYGKNNRPSGIPDRFSGSSSGN
TASLTITGAQAEDEADYYCNSSKWSWDPVVFGGGTKLTVLGQPKAAPSVTLFPPSSEELQANKATLVC
LISDFYPGAVTVAWKADSSPVKAGVETTTPSKQSNNKYAASSYLSLTPEQWKSHKSYSCQVTHEGSTV
EKTVAPTECS SEQ ID NO: 23 (XE114 antibody Light Chain amino acid sequence with a
substitution N -> Q at position 88)
The mutation is shown in bold and underlined.
SSELTQDPAVSVALGQTVRITCQGDSLRSYYASWYQQKPGQAPVLVIYGKNNRPSGIPDRFSGSSSGN
TASLTITGAQAEDEADYYCQSSKWSWDPVVFGGGTKLTVLGQPKAAPSVTLFPPSSEELQANKATLVC
LISDFYPGAVTVAWKADSSPVKAGVETTTPSKQSNNKYAASSYLSLTPEQWKSHKSYSCQVTHEGSTV
EKTVAPTECS SEQ ID NO: 24 (hIL2-XE114-hTNF$^{mut}$)
The amino acid sequence of the hIL2-XE114-hTNF$^{mut}$ conjugate (human
IL2-linker-XE114 VH-linker-XE114 VL-linker-human mutant
TNF) is shown below. The linker sequences are underlined. The
substitution N -> Q at position 88 in the XE114 antibody Light Chain
is underlined and in bold. The substitution R -> A at position 32 in
the TNF domain is shown in bold.
APTSSSTKKTQLQLEHLLLDLQMILNGINNYKNPKLTRMLTFKFYMPKKATELKHLQCLEEELKPLEE
VLNLAQSKNFHLRPRDLISNINVIVLELKGSETTFMCEYADETATIVEFLNRWITFCQSIISTLTGDG
```

SSGGSGGASEVQLLESGGGLVQPGGSLRLSCAASGFTFSSYAMSWVRQAPGKGLEWVSAIDGSGGSTY
YADSVKGRFTISRDNSKNTLYLQMNSLRAEDTAVYYCVKGPPVFDYWGQGTLVTVSSGGGGSGGGGSG

GGGSSELTQDPAVSVALGQTVRITCQGDSLRSYYASWYQQKPGQAPVLVIYGKNNRPSGIPDRFSGSS

SGNTASLTITGAQAEDEADYYCQSSKWSWDPVVFGGGTKLTVLGSSSSGSSSSGSSSSGVRSSSRTPS

DKPVAHVVANPQAEGQLQWLNRAANALLANGVELRDNQLVVPSEGLYLIYSQVLFKGQGCPSTHVLLT
HTISRIAVSYQTKVNLLSAIKSPCQRETPEGAEAKPWYEPIYLGGVFQLEKGDRLSAEINRPDYLDFA
ESGQVYFGIIAL

SEQ ID NO: 25 (hIL2-KSF-hTNFmut)
The

```
<400> SEQUENCE: 1

Ser Ser Tyr Ala Met Ser
1               5

<210> SEQ ID NO 2
<211> LENGTH: 17
<212> TYPE: PRT
<213> ORGANISM: Artificial Sequence
<220> FEATURE:
<223> OTHER INFORMATION: XE114 antibody VH domain CDR2

<400> SEQUENCE: 2

Ala Ile Asp Gly Ser Gly Gly Ser Thr Tyr Tyr Ala Asp Ser Val Lys
1               5                   10                  15

Gly

<210> SEQ ID NO 3
<211> LENGTH: 7
<212> TYPE: PRT
<213> ORGANISM: Artificial Sequence
<220> FEATURE:
<223> OTHER INFORMATION: XE114 antibody VH domain CDR3

<400> SEQUENCE: 3

Gly Pro Pro Val Phe Asp Tyr
1               5

<210> SEQ ID NO 4
<211> LENGTH: 11
<212> TYPE: PRT
<213> ORGANISM: Artificial Sequence
<220> FEATURE:
<223> OTHER INFORMATION: XE114 antibody VL domain CDR1

<400> SEQUENCE: 4

Gln Gly Asp Ser Leu Arg Ser Tyr Tyr Ala Ser
1               5                   10

<210> SEQ ID NO 5
<211> LENGTH: 7
<212> TYPE: PRT
<213> ORGANISM: Artificial Sequence
<220> FEATURE:
<223> OTHER INFORMATION: XE114 antibody VL domain CDR2

<400> SEQUENCE: 5

Gly Lys Asn Asn Arg Pro Ser
1               5

<210> SEQ ID NO 6
<211> LENGTH: 11
<212> TYPE: PRT
<213> ORGANISM: Artificial Sequence
<220> FEATURE:
<223> OTHER INFORMATION: XE114 antibody VL domain CDR3

<400> SEQUENCE: 6

Asn Ser Ser Lys Trp Ser Trp Asp Pro Val Val
1               5                   10

<210> SEQ ID NO 7
<211> LENGTH: 116
<212> TYPE: PRT
<213> ORGANISM: Artificial Sequence
<220> FEATURE:
<223> OTHER INFORMATION: XE114 antibody VH domain
```

<400> SEQUENCE: 7

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Asp Gly Ser Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Val Lys Gly Pro Pro Val Phe Asp Tyr Trp Gly Gln Gly Thr Leu Val
            100                 105                 110

Thr Val Ser Ser
        115

<210> SEQ ID NO 8
<211> LENGTH: 109
<212> TYPE: PRT
<213> ORGANISM: Artificial Sequence
<220> FEATURE:
<223> OTHER INFORMATION: XE114 antibody VL domain

<400> SEQUENCE: 8

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Ser Lys Trp Ser Trp Asp Pro
                85                  90                  95

Val Val Phe Gly Gly Gly Thr Lys Leu Thr Val Leu Gly
            100                 105

<210> SEQ ID NO 9
<211> LENGTH: 14
<212> TYPE: PRT
<213> ORGANISM: Artificial Sequence
<220> FEATURE:
<223> OTHER INFORMATION: linker between VH domain and VL domain of XE114
      antibody in scFv format

<400> SEQUENCE: 9

Gly Gly Gly Gly Ser Gly Gly Gly Gly Ser Gly Gly Gly Gly
1               5                   10

<210> SEQ ID NO 10
<211> LENGTH: 239
<212> TYPE: PRT
<213> ORGANISM: Artificial Sequence
<220> FEATURE:
<223> OTHER INFORMATION: XE114 antibody

<400> SEQUENCE: 10

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Asp Gly Ser Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Val Lys Gly Pro Pro Val Phe Asp Tyr Trp Gly Gln Gly Thr Leu Val
            100                 105                 110

Thr Val Ser Ser Gly Gly Gly Gly Ser Gly Gly Gly Gly Ser Gly Gly
        115                 120                 125

Gly Gly Ser Ser Glu Leu Thr Gln Asp Pro Ala Val Ser Val Ala Leu
130                 135                 140

Gly Gln Thr Val Arg Ile Thr Cys Gln Gly Asp Ser Leu Arg Ser Tyr
145                 150                 155                 160

Tyr Ala Ser Trp Tyr Gln Gln Lys Pro Gly Gln Ala Pro Val Leu Val
                165                 170                 175

Ile Tyr Gly Lys Asn Asn Arg Pro Ser Gly Ile Pro Asp Arg Phe Ser
            180                 185                 190

Gly Ser Ser Ser Gly Asn Thr Ala Ser Leu Thr Ile Thr Gly Ala Gln
        195                 200                 205

Ala Glu Asp Glu Ala Asp Tyr Tyr Cys Asn Ser Ser Lys Trp Ser Trp
    210                 215                 220

Asp Pro Val Val Phe Gly Gly Gly Thr Lys Leu Thr Val Leu Gly
225                 230                 235

<210> SEQ ID NO 11
<211> LENGTH: 348
<212> TYPE: DNA
<213> ORGANISM: Artificial Sequence
<220> FEATURE:
<223> OTHER INFORMATION: XE114 antibody VH domain

<400> SEQUENCE: 11

```
gaggtgcagc tgttggagtc tgggggaggc ttggtacagc ctggggggtc cctgagactc      60
tcctgtgcag cctctggatt cacctttagc agctatgcca tgagctgggt ccgccaggct     120
ccagggaagg ggctggagtg ggtctcagct attgacggta gtggtggtag cacatactac     180
gcagactccg tgaagggccg gttcaccatc tccagagaca attccaagaa cacgctgtat     240
ctgcaaatga acagcctgag agccgaagac acggccgtat attactgtgt gaaaggtccg     300
ccggtgtttg actactgggg ccagggaacc ctggtcaccg tctcgagt                  348
```

<210> SEQ ID NO 12
<211> LENGTH: 327
<212> TYPE: DNA
<213> ORGANISM: Artificial Sequence
<220> FEATURE:
<223> OTHER INFORMATION: XE114 antibody VL domain

<400> SEQUENCE: 12

```
tcgtctgagc tgactcagga ccctgctgtg tctgtggcct tgggacagac agtcaggatc    60
acatgccaag agacagtctc agaagctat tatgcaagct ggtaccagca gaagccagga   120
caggcccctg tacttgtcat ctatggtaaa acaaccggc cctcagggat cccagaccga   180
ttctctggct ccagctcagg aaacacagct tccttgacca tcactggggc tcaggcggaa   240
gatgaggctg actattactg taattcctct aagtggtctt gggatcccgt ggtattcggc   300
ggagggacca agctgaccgt cctaggc                                       327
```

<210> SEQ ID NO 13
<211> LENGTH: 42
<212> TYPE: DNA
<213> ORGANISM: Artificial Sequence
<220> FEATURE:
<223> OTHER INFORMATION: linker between VH domain and VL domain of XE114 antib

<400> SEQUENCE: 13

```
ggtggaggcg gttcaggcgg aggtggctct ggcggtggcg ga                       42
```

<210> SEQ ID NO 14
<211> LENGTH: 717
<212> TYPE: DNA
<213> ORGANISM: Artificial Sequence
<220> FEATURE:
<223> OTHER INFORMATION: XE114 scFv antibody

<400> SEQUENCE: 14

```
gaggtgcagc tgttggagtc tgggggaggc ttggtacagc ctgggggtc cctgagactc     60
tcctgtgcag cctctggatt cacctttagc agctatgcca tgagctgggt ccgccaggct   120
ccagggaagg gctggagtg gtctcagct attgacggta gtggtggtag cacatactac    180
gcagactccg tgaagggccg gttcaccatc tccagagaca attccaagaa cacgctgtat   240
ctgcaaatga acagcctgag agccgaagac acggccgtat attactgtgt gaaaggtccg   300
ccggtgtttg actactgggg ccagggaacc ctggtcaccg tctcgagtgg tggaggcggt   360
tcaggcggag gtggctctgg cggtggcgga tcgtctgagc tgactcagga ccctgctgtg   420
tctgtggcct tgggacagac agtcaggatc acatgccaag agacagtctc agaagctat   480
tatgcaagct ggtaccagca gaagccagga caggcccctg tacttgtcat ctatggtaaa   540
acaaccggc cctcagggat cccagaccga ttctctggct ccagctcagg aaacacagct   600
tccttgacca tcactggggc tcaggcggaa gatgaggctg actattactg taattcctct   660
aagtggtctt gggatcccgt ggtattcggc ggagggacca agctgaccgt cctaggc      717
```

<210> SEQ ID NO 15
<211> LENGTH: 284
<212> TYPE: PRT
<213> ORGANISM: Artificial Sequence
<220> FEATURE:
<223> OTHER INFORMATION: Sequence of Carbonic Anhydrase IX extracellular domain with C-terminal His-tag

<400> SEQUENCE: 15

```
Gly Asp Pro Gln Glu Pro Gln Asn Asn Ala His Arg Asp Lys Glu Gly
 1               5                  10                  15
Asp Asp Gln Ser His Trp Arg Tyr Gly Gly Asp Pro Pro Trp Pro Arg
            20                  25                  30
```

Val Ser Pro Ala Cys Ala Gly Arg Phe Gln Ser Pro Val Asp Ile Arg
         35                  40                  45

Pro Gln Leu Ala Ala Phe Cys Pro Ala Leu Arg Pro Leu Glu Leu Leu
 50                  55                  60

Gly Phe Gln Leu Pro Pro Leu Pro Glu Leu Arg Leu Arg Asn Asn Gly
65                  70                  75                  80

His Ser Val Gln Leu Thr Leu Pro Pro Gly Leu Glu Met Ala Leu Gly
                 85                  90                  95

Pro Gly Arg Glu Tyr Arg Ala Leu Gln Leu His Leu His Trp Gly Ala
             100                 105                 110

Ala Gly Arg Pro Gly Ser Glu His Thr Val Glu Gly His Arg Phe Pro
         115                 120                 125

Ala Glu Ile His Val Val His Leu Ser Thr Ala Phe Ala Arg Val Asp
    130                 135                 140

Glu Ala Leu Gly Arg Pro Gly Gly Leu Ala Val Leu Ala Ala Phe Leu
145                 150                 155                 160

Glu Glu Gly Pro Glu Glu Asn Ser Ala Tyr Glu Gln Leu Leu Ser Arg
                165                 170                 175

Leu Glu Glu Ile Ala Glu Glu Gly Ser Glu Thr Gln Val Pro Gly Leu
            180                 185                 190

Asp Ile Ser Ala Leu Leu Pro Ser Asp Phe Ser Arg Tyr Phe Gln Tyr
        195                 200                 205

Glu Gly Ser Leu Thr Thr Pro Pro Cys Ala Gln Gly Val Ile Trp Thr
    210                 215                 220

Val Phe Asn Gln Thr Val Met Leu Ser Ala Lys Gln Leu His Thr Leu
225                 230                 235                 240

Ser Asp Thr Leu Trp Gly Pro Gly Asp Ser Arg Leu Gln Leu Asn Phe
                245                 250                 255

Arg Ala Thr Gln Pro Leu Asn Gly Arg Val Ile Glu Ala Ser Phe Pro
            260                 265                 270

Ala Gly Val Asp Ser Ser His His His His His
        275                 280

<210> SEQ ID NO 16
<211> LENGTH: 278
<212> TYPE: PRT
<213> ORGANISM: Artificial Sequence
<220> FEATURE:
<223> OTHER INFORMATION: Sequence of Carbonic Anhydrase IX extracellular
      domain

<400> SEQUENCE: 16

Gly Asp Pro Gln Glu Pro Gln Asn Asn Ala His Arg Asp Lys Glu Gly
1               5                   10                  15

Asp Asp Gln Ser His Trp Arg Tyr Gly Gly Asp Pro Pro Trp Pro Arg
            20                  25                  30

Val Ser Pro Ala Cys Ala Gly Arg Phe Gln Ser Pro Val Asp Ile Arg
         35                  40                  45

Pro Gln Leu Ala Ala Phe Cys Pro Ala Leu Arg Pro Leu Glu Leu Leu
 50                  55                  60

Gly Phe Gln Leu Pro Pro Leu Pro Glu Leu Arg Leu Arg Asn Asn Gly
65                  70                  75                  80

His Ser Val Gln Leu Thr Leu Pro Pro Gly Leu Glu Met Ala Leu Gly
                 85                  90                  95

Pro Gly Arg Glu Tyr Arg Ala Leu Gln Leu His Leu His Trp Gly Ala
             100                 105                 110

```
Ala Gly Arg Pro Gly Ser Glu His Thr Val Glu Gly His Arg Phe Pro
            115                 120                 125

Ala Glu Ile His Val Val His Leu Ser Thr Ala Phe Ala Arg Val Asp
        130                 135                 140

Glu Ala Leu Gly Arg Pro Gly Gly Leu Ala Val Leu Ala Ala Phe Leu
145                 150                 155                 160

Glu Glu Gly Pro Glu Glu Asn Ser Ala Tyr Glu Gln Leu Leu Ser Arg
                165                 170                 175

Leu Glu Glu Ile Ala Glu Glu Gly Ser Glu Thr Gln Val Pro Gly Leu
            180                 185                 190

Asp Ile Ser Ala Leu Leu Pro Ser Asp Phe Ser Arg Tyr Phe Gln Tyr
        195                 200                 205

Glu Gly Ser Leu Thr Thr Pro Pro Cys Ala Gln Gly Val Ile Trp Thr
    210                 215                 220

Val Phe Asn Gln Thr Val Met Leu Ser Ala Lys Gln Leu His Thr Leu
225                 230                 235                 240

Ser Asp Thr Leu Trp Gly Pro Gly Asp Ser Arg Leu Gln Leu Asn Phe
                245                 250                 255

Arg Ala Thr Gln Pro Leu Asn Gly Arg Val Ile Glu Ala Ser Phe Pro
            260                 265                 270

Ala Gly Val Asp Ser Ser
        275

<210> SEQ ID NO 17
<211> LENGTH: 459
<212> TYPE: PRT
<213> ORGANISM: Artificial Sequence
<220> FEATURE:
<223> OTHER INFORMATION: Sequence of Carbonic Anhydrase IX

<400> SEQUENCE: 17

Met Ala Pro Leu Cys Pro Ser Pro Trp Leu Pro Leu Leu Ile Pro Ala
1               5                   10                  15

Pro Ala Pro Gly Leu Thr Val Gln Leu Leu Ser Leu Leu Leu Leu
            20                  25                  30

Val Pro Val His Pro Gln Arg Leu Pro Arg Met Gln Glu Asp Ser Pro
        35                  40                  45

Leu Gly Gly Gly Ser Ser Gly Glu Asp Asp Pro Leu Gly Glu Glu Asp
    50                  55                  60

Leu Pro Ser Glu Glu Asp Ser Pro Arg Glu Glu Asp Pro Pro Gly Glu
65                  70                  75                  80

Glu Asp Leu Pro Gly Glu Glu Asp Leu Pro Gly Glu Glu Asp Leu Pro
                85                  90                  95

Glu Val Lys Pro Lys Ser Glu Glu Gly Ser Leu Lys Leu Glu Asp
            100                 105                 110

Leu Pro Thr Val Glu Ala Pro Gly Asp Pro Gln Glu Pro Gln Asn Asn
        115                 120                 125

Ala His Arg Asp Lys Glu Gly Asp Asp Gln Ser His Trp Arg Tyr Gly
    130                 135                 140

Gly Asp Pro Pro Trp Pro Arg Val Ser Pro Ala Cys Ala Gly Arg Phe
145                 150                 155                 160

Gln Ser Pro Val Asp Ile Arg Pro Gln Leu Ala Ala Phe Cys Pro Ala
                165                 170                 175

Leu Arg Pro Leu Glu Leu Leu Gly Phe Gln Leu Pro Pro Leu Pro Glu
            180                 185                 190
```

```
Leu Arg Leu Arg Asn Asn Gly His Ser Val Gln Leu Thr Leu Pro Pro
            195                 200                 205

Gly Leu Glu Met Ala Leu Gly Pro Gly Arg Glu Tyr Arg Ala Leu Gln
    210                 215                 220

Leu His Leu His Trp Gly Ala Ala Gly Arg Pro Gly Ser Glu His Thr
225                 230                 235                 240

Val Glu Gly His Arg Phe Pro Ala Glu Ile His Val Val His Leu Ser
                245                 250                 255

Thr Ala Phe Ala Arg Val Asp Glu Ala Leu Gly Arg Pro Gly Gly Leu
            260                 265                 270

Ala Val Leu Ala Ala Phe Leu Glu Glu Gly Pro Glu Glu Asn Ser Ala
        275                 280                 285

Tyr Glu Gln Leu Leu Ser Arg Leu Glu Glu Ile Ala Glu Glu Gly Ser
    290                 295                 300

Glu Thr Gln Val Pro Gly Leu Asp Ile Ser Ala Leu Leu Pro Ser Asp
305                 310                 315                 320

Phe Ser Arg Tyr Phe Gln Tyr Glu Gly Ser Leu Thr Thr Pro Pro Cys
                325                 330                 335

Ala Gln Gly Val Ile Trp Thr Val Phe Asn Gln Thr Val Met Leu Ser
            340                 345                 350

Ala Lys Gln Leu His Thr Leu Ser Asp Thr Leu Trp Gly Pro Gly Asp
        355                 360                 365

Ser Arg Leu Gln Leu Asn Phe Arg Ala Thr Gln Pro Leu Asn Gly Arg
    370                 375                 380

Val Ile Glu Ala Ser Phe Pro Ala Gly Val Asp Ser Ser Pro Arg Ala
385                 390                 395                 400

Ala Glu Pro Val Gln Leu Asn Ser Cys Leu Ala Ala Gly Asp Ile Leu
                405                 410                 415

Ala Leu Val Phe Gly Leu Leu Phe Ala Val Thr Ser Val Ala Phe Leu
            420                 425                 430

Val Gln Met Arg Arg Gln His Arg Arg Gly Thr Lys Gly Gly Val Ser
        435                 440                 445

Tyr Arg Pro Ala Glu Val Ala Glu Thr Gly Ala
    450                 455

<210> SEQ ID NO 18
<211> LENGTH: 5
<212> TYPE: PRT
<213> ORGANISM: Artificial Sequence
<220> FEATURE:
<223> OTHER INFORMATION: linker between VH domain and VL domain of XE114
      antibody in diabody format

<400> SEQUENCE: 18

Gly Gly Ser Gly Gly
1               5

<210> SEQ ID NO 19
<211> LENGTH: 11
<212> TYPE: PRT
<213> ORGANISM: Artificial Sequence
<220> FEATURE:
<223> OTHER INFORMATION: alternative XE114 antibody LCDR3 without
      glycosylation motif, comprising a substitution N -> Q

<400> SEQUENCE: 19

Gln Ser Ser Lys Trp Ser Trp Asp Pro Val Val
1               5                   10
```

<210> SEQ ID NO 20
<211> LENGTH: 109
<212> TYPE: PRT
<213> ORGANISM: Artificial Sequence
<220> FEATURE:
<223> OTHER INFORMATION: XE114 antibody VL domain amino acid sequence
      without without glycosylation motif, comprising a substitution
      N -> Q at position 88

<400> SEQUENCE: 20

```
Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Gln Ser Ser Lys Trp Ser Trp Asp Pro
                85                  90                  95

Val Val Phe Gly Gly Gly Thr Lys Leu Thr Val Leu Gly
            100                 105
```

<210> SEQ ID NO 21
<211> LENGTH: 446
<212> TYPE: PRT
<213> ORGANISM: Artificial Sequence
<220> FEATURE:
<223> OTHER INFORMATION: XE114 antibody Heavy Chain

<400> SEQUENCE: 21

```
Glu Val Gln Leu Leu Glu Ser Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Asp Gly Ser Gly Gly Ser Thr Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Val Lys Gly Pro Pro Val Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190
```

Gly Thr Gln Thr Tyr Ile Cys Asn Val Asn His Lys Pro Ser Asn Thr
            195                 200                 205

Lys Val Asp Lys Lys Val Glu Pro Lys Ser Ser Asp Lys Thr His Thr
210                 215                 220

Ser Pro Pro Ser Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
            245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
            325                 330                 335

Lys Ala Lys Gly Gln Pro Arg Glu Pro Gln Val Tyr Thr Leu Pro Pro
        340                 345                 350

Ser Arg Asp Glu Leu Thr Lys Asn Gln Val Ser Leu Thr Cys Leu Val
    355                 360                 365

Lys Gly Phe Tyr Pro Ser Asp Ile Ala Val Glu Trp Glu Ser Asn Gly
        370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
            405                 410                 415

Gln Gln Gly Asn Val Phe Ser Cys Ser Val Met His Glu Ala Leu His
        420                 425                 430

Asn His Tyr Thr Gln Lys Ser Leu Ser Leu Ser Pro Gly Lys
    435                 440                 445

<210> SEQ ID NO 22
<211> LENGTH: 214
<212> TYPE: PRT
<213> ORGANISM: Artificial Sequence
<220> FEATURE:
<223> OTHER INFORMATION: XE114 antibody Light Chain

<400> SEQUENCE: 22

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Ser Lys Trp Ser Trp Asp Pro
                85                  90                  95

Val Val Phe Gly Gly Gly Thr Lys Leu Thr Val Leu Gly Gln Pro Lys
            100                 105                 110

```
Ala Ala Pro Ser Val Thr Leu Phe Pro Pro Ser Ser Glu Glu Leu Gln
            115                 120                 125

Ala Asn Lys Ala Thr Leu Val Cys Leu Ile Ser Asp Phe Tyr Pro Gly
        130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Lys Ser
            180                 185                 190

Tyr Ser Cys Gln Val Thr His Glu Gly Ser Thr Val Glu Lys Thr Val
        195                 200                 205

Ala Pro Thr Glu Cys Ser
    210

<210> SEQ ID NO 23
<211> LENGTH: 214
<212> TYPE: PRT
<213> ORGANISM: Artificial Sequence
<220> FEATURE:
<223> OTHER INFORMATION: XE114 antibody Light Chain amino acid sequence
      with a substitution N -> Q at position 88

<400> SEQUENCE: 23

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Gln Ser Ser Lys Trp Ser Trp Asp Pro
                85                  90                  95

Val Val Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
            115                 120                 125

Ala Asn Lys Ala Thr Leu Val Cys Leu Ile Ser Asp Phe Tyr Pro Gly
        130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Lys Ser
            180                 185                 190

Tyr Ser Cys Gln Val Thr His Glu Gly Ser Thr Val Glu Lys Thr Val
        195                 200                 205

Ala Pro Thr Glu Cys Ser
    210
```

```
<210> SEQ ID NO 24
<211> LENGTH: 556
<212> TYPE: PRT
<213> ORGANISM: Artificial Sequence
<220> FEATURE:
<223> OTHER INFORMATION: hIL2-XE114-hTNFmut

<400> SEQUENCE: 24
```

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr Gly Asp Gly Ser Ser Gly Ser Gly Gly Ala
    130                 135                 140

Ser Glu Val Gln Leu Leu Glu Ser Gly Gly Gly Leu Val Gln Pro Gly
145                 150                 155                 160

Gly Ser Leu Arg Leu Ser Cys Ala Ala Ser Gly Phe Thr Phe Ser Ser
                165                 170                 175

Tyr Ala Met Ser Trp Val Arg Gln Ala Pro Gly Lys Gly Leu Glu Trp
            180                 185                 190

Val Ser Ala Ile Asp Gly Ser Gly Gly Ser Thr Tyr Tyr Ala Asp Ser
        195                 200                 205

Val Lys Gly Arg Phe Thr Ile Ser Arg Asp Asn Ser Lys Asn Thr Leu
    210                 215                 220

Tyr Leu Gln Met Asn Ser Leu Arg Ala Glu Asp Thr Ala Val Tyr Tyr
225                 230                 235                 240

Cys Val Lys Gly Pro Pro Val Phe Asp Tyr Trp Gly Gln Gly Thr Leu
                245                 250                 255

Val Thr Val Ser Ser Gly Gly Gly Gly Ser Gly Gly Gly Gly Ser Gly
            260                 265                 270

Gly Gly Gly Ser Ser Glu Leu Thr Gln Asp Pro Ala Val Ser Val Ala
        275                 280                 285

Leu Gly Gln Thr Val Arg Ile Thr Cys Gln Gly Asp Ser Leu Arg Ser
    290                 295                 300

Tyr Tyr Ala Ser Trp Tyr Gln Gln Lys Pro Gly Gln Ala Pro Val Leu
305                 310                 315                 320

Val Ile Tyr Gly Lys Asn Asn Arg Pro Ser Gly Ile Pro Asp Arg Phe
                325                 330                 335

Ser Gly Ser Ser Ser Gly Asn Thr Ala Ser Leu Thr Ile Thr Gly Ala
            340                 345                 350

Gln Ala Glu Asp Glu Ala Asp Tyr Tyr Cys Gln Ser Ser Lys Trp Ser
        355                 360                 365

```
Trp Asp Pro Val Val Phe Gly Gly Thr Lys Leu Thr Val Leu Gly
370                 375                 380

Ser Ser Ser Ser Gly Ser Ser Ser Gly Ser Ser Ser Ser Gly Val
385                 390                 395                 400

Arg Ser Ser Arg Thr Pro Ser Asp Lys Pro Val Ala His Val Val
            405                 410                 415

Ala Asn Pro Gln Ala Glu Gly Gln Leu Gln Trp Leu Asn Arg Ala Ala
        420                 425                 430

Asn Ala Leu Leu Ala Asn Gly Val Glu Leu Arg Asp Asn Gln Leu Val
        435                 440                 445

Val Pro Ser Glu Gly Leu Tyr Leu Ile Tyr Ser Gln Val Leu Phe Lys
450                 455                 460

Gly Gln Gly Cys Pro Ser Thr His Val Leu Leu Thr His Thr Ile Ser
465                 470                 475                 480

Arg Ile Ala Val Ser Tyr Gln Thr Lys Val Asn Leu Leu Ser Ala Ile
                485                 490                 495

Lys Ser Pro Cys Gln Arg Glu Thr Pro Glu Gly Ala Glu Ala Lys Pro
            500                 505                 510

Trp Tyr Glu Pro Ile Tyr Leu Gly Gly Val Phe Gln Leu Glu Lys Gly
        515                 520                 525

Asp Arg Leu Ser Ala Glu Ile Asn Arg Pro Asp Tyr Leu Asp Phe Ala
530                 535                 540

Glu Ser Gly Gln Val Tyr Phe Gly Ile Ile Ala Leu
545                 550                 555

<210> SEQ ID NO 25
<211> LENGTH: 558
<212> TYPE: PRT
<213> ORGANISM: Artificial Sequence
<220> FEATURE:
<223> OTHER INFORMATION: hIL2-KSF-hTNFmut

<400> SEQUENCE: 25

Ala Pro Thr Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr Gly Asp Gly Ser Ser Gly Ser Gly Gly Ala
        130                 135                 140

Ser Glu Val Gln Leu Leu Glu Ser Gly Gly Gly Leu Val Gln Pro Gly
145                 150                 155                 160

Gly Ser Leu Arg Leu Ser Cys Ala Ala Ser Gly Phe Thr Phe Ser Ser
                165                 170                 175
```

-continued

```
Tyr Ala Met Ser Trp Val Arg Gln Ala Pro Gly Lys Gly Leu Glu Trp
            180                 185                 190

Val Ser Ala Ile Ser Gly Ser Gly Gly Ser Thr Tyr Tyr Ala Asp Ser
        195                 200                 205

Val Lys Gly Arg Phe Thr Ile Ser Arg Asp Asn Ser Lys Asn Thr Leu
    210                 215                 220

Tyr Leu Gln Met Asn Ser Leu Arg Ala Glu Asp Thr Ala Val Tyr Tyr
225                 230                 235                 240

Cys Ala Lys Ser Pro Lys Val Ser Leu Phe Asp Tyr Trp Gly Gln Gly
                245                 250                 255

Thr Leu Val Thr Val Ser Ser Gly Gly Gly Gly Ser Gly Gly Gly Gly
            260                 265                 270

Ser Gly Gly Gly Gly Ser Ser Glu Leu Thr Gln Asp Pro Ala Val Ser
        275                 280                 285

Val Ala Leu Gly Gln Thr Val Arg Ile Thr Cys Gln Gly Asp Ser Leu
    290                 295                 300

Arg Ser Tyr Tyr Ala Ser Trp Tyr Gln Gln Lys Pro Gly Gln Ala Pro
305                 310                 315                 320

Val Leu Val Ile Tyr Gly Lys Asn Asn Arg Pro Ser Gly Ile Pro Asp
                325                 330                 335

Arg Phe Ser Gly Ser Ser Ser Gly Asn Thr Ala Ser Leu Thr Ile Thr
            340                 345                 350

Gly Ala Gln Ala Glu Asp Glu Ala Asp Tyr Tyr Cys Asn Ser Ser Pro
        355                 360                 365

Leu Asn Arg Leu Ala Val Val Phe Gly Gly Gly Thr Lys Leu Thr Val
    370                 375                 380

Leu Gly Ser Ser Ser Gly Ser Ser Ser Gly Ser Ser Ser Ser
385                 390                 395                 400

Gly Val Arg Ser Ser Arg Thr Pro Ser Asp Lys Pro Val Ala His
                405                 410                 415

Val Val Ala Asn Pro Gln Ala Glu Gly Gln Leu Gln Trp Leu Asn Arg
            420                 425                 430

Ala Ala Asn Ala Leu Leu Ala Asn Gly Val Glu Leu Arg Asp Asn Gln
        435                 440                 445

Leu Val Val Pro Ser Glu Gly Leu Tyr Leu Ile Tyr Ser Gln Val Leu
    450                 455                 460

Phe Lys Gly Gln Gly Cys Pro Ser Thr His Val Leu Leu Thr His Thr
465                 470                 475                 480

Ile Ser Arg Ile Ala Val Ser Tyr Gln Thr Lys Val Asn Leu Leu Ser
                485                 490                 495

Ala Ile Lys Ser Pro Cys Gln Arg Glu Thr Pro Glu Gly Ala Glu Ala
            500                 505                 510

Lys Pro Trp Tyr Glu Pro Ile Tyr Leu Gly Gly Val Phe Gln Leu Glu
        515                 520                 525

Lys Gly Asp Arg Leu Ser Ala Glu Ile Asn Arg Pro Asp Tyr Leu Asp
    530                 535                 540

Phe Ala Glu Ser Gly Gln Val Tyr Phe Gly Ile Ile Ala Leu
545                 550                 555
```

<210> SEQ ID NO 26
<211> LENGTH: 65
<212> TYPE: DNA
<213> ORGANISM: Artificial Sequence
<220> FEATURE:
<223> OTHER INFORMATION: primer "Leader Seq DP47 Fo>"

-continued

<400> SEQUENCE: 26
tcctcctgtt cctcgtcgct gtggctacag gtgtgcactc ggaggtgcag ctgttggagt    60
ctggg    65

<210> SEQ ID NO 27
<211> LENGTH: 44
<212> TYPE: DNA
<213> ORGANISM: Artificial Sequence
<220> FEATURE:
<223> OTHER INFORMATION: primer "Not STOP DPL16 Ba<"

<400> SEQUENCE: 27 ttttccttttt gcggccgctt agcctaggac ggtcagcttg gtcc    44

<210> SEQ ID NO 28
<211> LENGTH: 57
<212> TYPE: DNA
<213> ORGANISM: Artificial Sequence
<220> FEATURE:
<223> OTHER INFORMATION: primer "NheI leader>"

<400> SEQUENCE: 28
ctagctagcg tcgaccatgg gctggagcct gatcctcctg ttcctcgtcg ctgtggc    57

<210> SEQ ID NO 29
<211> LENGTH: 44
<212> TYPE: DNA
<213> ORGANISM: Artificial Sequence
<220> FEATURE:
<223> OTHER INFORMATION: primer "Not STOP DPL16 Ba<"

<400> SEQUENCE: 29 ttttccttttt gcggccgctt agcctaggac ggtcagcttg gtcc    44

<210> SEQ ID NO 30
<211> LENGTH: 48
<212> TYPE: DNA
<213> ORGANISM: Artificial Sequence
<220> FEATURE:
<223> OTHER INFORMATION: primer "Link-F8VH>"

<400> SEQUENCE: 30
gctcttcagg cggctctggc ggagcttccg aggtgcagct gttggagt    48

<210> SEQ ID NO 31
<211> LENGTH: 49
<212> TYPE: DNA
<213> ORGANISM: Artificial Sequence
<220> FEATURE:
<223> OTHER INFORMATION: primer "VL-link(15aa)-lamda ba"

<400> SEQUENCE: 31
ccggaagagc tactacccga tgaggaagag cctaggacgg tcagcttgg    49

<210> SEQ ID NO 32
<211> LENGTH: 47
<212> TYPE: DNA
<213> ORGANISM: Artificial Sequence
<220> FEATURE:
<223> OTHER INFORMATION: primer "hIL2-Li12aa<"

<400> SEQUENCE: 32
gccagagccg cctgaagagc cgtcaccagt cagtgttgag atgatgc    47

```
<210> SEQ ID NO 33
<211> LENGTH: 55
<212> TYPE: DNA
<213> ORGANISM: Artificial Sequence
<220> FEATURE:
<223> OTHER INFORMATION: primer "link-hsTNF>"

<400> SEQUENCE: 33
cgggtagtag ctcttccggc tcatcgtcca gcggcgtcag atcatcttct cgaac      55

<210> SEQ ID NO 34
<211> LENGTH: 50
<212> TYPE: DNA
<213> ORGANISM: Artificial Sequence
<220> FEATURE:
<223> OTHER INFORMATION: primer "NotISTOP-hsTNF<"

<400> SEQUENCE: 34
tttccttttg cggccgctca ttaagctatc acagggcaat gatcccaaag            50

<210> SEQ ID NO 35
<211> LENGTH: 239
<212> TYPE: PRT
<213> ORGANISM: Artificial Sequence
<220> FEATURE:
<223> OTHER INFORMATION: XE114 antibody amino acid sequence in scFv
      format without glycosylation motif, comprising a substitution
      N -> Q at position 88 of the VL domain

<400> SEQUENCE: 35
```

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Asp Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Val Lys Gly Pro Pro Val Phe Asp Tyr Trp Gly Gln Gly Thr Leu Val
            100                 105                 110

Thr Val Ser Ser Gly Gly Gly Gly Ser Gly Gly Gly Gly Ser Gly Gly
        115                 120                 125

Gly Gly Ser Ser Glu Leu Thr Gln Asp Pro Ala Val Ser Val Ala Leu
    130                 135                 140

Gly Gln Thr Val Arg Ile Thr Cys Gln Gly Asp Ser Leu Arg Ser Tyr
145                 150                 155                 160

Tyr Ala Ser Trp Tyr Gln Gln Lys Pro Gly Gln Ala Pro Val Leu Val
                165                 170                 175

Ile Tyr Gly Lys Asn Asn Arg Pro Ser Gly Ile Pro Asp Arg Phe Ser
            180                 185                 190

Gly Ser Ser Ser Gly Asn Thr Ala Ser Leu Thr Ile Thr Gly Ala Gln
        195                 200                 205

```
Ala Glu Asp Glu Ala Asp Tyr Tyr Cys Gln Ser Ser Lys Trp Ser Trp
    210                 215                 220

Asp Pro Val Val Phe Gly Gly Gly Thr Lys Leu Thr Val Leu Gly
225                 230                 235
```

The invention claimed is:

1. A specific binding member that binds carbonic anhydrase IX (CAIX), wherein the specific binding member comprises a VH domain comprising a framework and a set of complementarity determining regions HCDR1, HCDR2 and HCDR3, and a VL domain comprising a framework and a set of complementarity determining regions LCDR1, LCDR2 and LCDR3, wherein: HCDR1 has the amino acid sequence of SEQ ID NO: 1, HCDR2 has the amino acid sequence of SEQ ID NO: 2, HCDR3 has the amino acid sequence of SEQ ID NO: 3, LCDR1 has the amino acid sequence of SEQ ID NO: 4, LCDR2 has the amino acid sequence of SEQ ID NO: 5, and LCDR3 has the amino acid sequence of SEQ ID NO: 19 or 6.

2. The specific binding member according to claim 1, wherein the specific binding member binds to the extracellular domain of CAIX.

3. The specific binding member according to claim 2, wherein the extracellular domain of CAIX has the sequence of SEQ ID NO: 16.

4. The specific binding member according to claim 1, wherein the VH domain framework and/or the VL domain framework is a human germline framework.

5. The specific binding member according to claim 1, wherein the VH domain has the amino acid sequence of SEQ ID NO: 7 and/or the VL domain has the amino acid sequence of SEQ ID NO: 20 or 8.

6. The specific binding member according to claim 1, wherein the specific binding member is an antibody molecule.

7. The specific binding member according to claim 1, wherein the binding member is or comprises a single chain Fv (scFv), or is an immunoglobulin G (IgG).

8. The specific binding member according to claim 7, wherein the binding member is a small immunoprotein (SIP), or a diabody.

9. The specific binding member according to claim 1, wherein the binding member is conjugated to a detectable label.

10. The specific binding member according to claim 1, wherein the binding member is conjugated to a biocidal molecule, a cytotoxic molecule, or a radioisotope.

11. The specific binding member according to claim 1, wherein the binding member is conjugated to interleukin-2 (IL2), and a tumour necrosis factor (TNF) mutant, wherein the TNF mutant has reduced activity relative to the wild type TNF.

12. A method of treating cancer in a patient, wherein the method comprises administering to the patient a therapeutically effective amount of a specific binding member according to claim 1.

13. A method of imaging, detecting, or diagnosing cancer expressing CAIX in a human or animal, comprising the steps of: (i) administering to the human or animal a specific binding member according to claim 1; (ii) determining the presence or absence of the specific binding member in the human or animal body; wherein the detection of the specific binding member in the human or animal body indicates the presence of a cancer expressing CAIX.

14. A method of delivering a molecule to sites of cancer in a patient, the method comprising administering a specific binding member according to claim 1 to the patient, wherein the molecule is conjugated to the binding member.

* * * * *